(12) United States Patent
Stephens et al.

(10) Patent No.: US 12,384,838 B2
(45) Date of Patent: Aug. 12, 2025

(54) CXCL10 BINDING PROTEINS AND USES THEREOF

(71) Applicant: Hudson Institute of Medical Research, Clayton (AU)

(72) Inventors: Andrew N. Stephens, Knoxfield (AU); Adam Rainczuk, Belgrave (AU); Sung-Woog Kang, Malvern East (AU)

(73) Assignee: Hudson Institute of Medical Research (AU)

( * ) Notice: Subject to any disclaimer, the term of this patent is extended or adjusted under 35 U.S.C. 154(b) by 0 days.

(21) Appl. No.: 18/341,278

(22) Filed: Jun. 26, 2023

(65) Prior Publication Data

US 2024/0076366 A1 Mar. 7, 2024

Related U.S. Application Data

(63) Continuation of application No. 17/783,528, filed as application No. PCT/AU2020/051403 on Dec. 18, 2020, now Pat. No. 11,725,048.

(30) Foreign Application Priority Data

Dec. 20, 2019 (AU) .............................. 2019904859

(51) Int. Cl.
*C07K 16/24* (2006.01)
*G01N 33/574* (2006.01)

(52) U.S. Cl.
CPC ....... *C07K 16/24* (2013.01); *G01N 33/57449* (2013.01); *C07K 2317/34* (2013.01); *C07K 2317/92* (2013.01); *G01N 2333/521* (2013.01)

(58) Field of Classification Search
None
See application file for complete search history.

(56) References Cited

U.S. PATENT DOCUMENTS

| | | | |
|---|---|---|---|
| 7,964,194 B2 | 6/2011 | Lillard, Jr | |
| 8,563,476 B2 | 10/2013 | Lillard, Jr. | |
| 2010/0040577 A1 | 2/2010 | Albert et al. | |
| 2015/0266951 A1 | 9/2015 | Song | |
| 2021/0347847 A1 | 11/2021 | Regev | |
| 2022/0162705 A1 | 5/2022 | Denkert | |

FOREIGN PATENT DOCUMENTS

| | | |
|---|---|---|
| EP | 0569141 A2 | 11/1993 |
| EP | 1641818 B1 | 12/2008 |
| EP | 3887548 A1 | 10/2021 |
| WO | 1994/04678 A1 | 3/1994 |
| WO | 1994/07921 A1 | 4/1994 |
| WO | 1997/049805 A2 | 12/1997 |
| WO | 1998/044001 A1 | 10/1998 |
| WO | 1999/045110 A1 | 9/1999 |
| WO | 1999/057134 A1 | 11/1999 |
| WO | 1999/058661 A1 | 11/1999 |
| WO | 2000/34317 A2 | 6/2000 |
| WO | 2002/066630 A1 | 8/2002 |
| WO | 2002/088171 A2 | 11/2002 |
| WO | 2004/108158 A1 | 12/2004 |
| WO | 2005/056764 A2 | 6/2005 |
| WO | 2006/033386 A1 | 3/2006 |
| WO | 2007/019620 A1 | 2/2007 |
| WO | 2007045996 A1 | 4/2007 |
| WO | 2007073220 A1 | 6/2007 |
| WO | 2008/123866 A2 | 10/2008 |
| WO | 2009037572 A2 | 3/2009 |
| WO | 2009/132401 A2 | 11/2009 |
| WO | 2010/080538 A1 | 7/2010 |
| WO | 2011/107595 A1 | 9/2011 |
| WO | 2012/040793 A1 | 4/2012 |
| WO | 2012082494 A2 | 6/2012 |
| WO | 2012082742 A2 | 6/2012 |
| WO | 2012/115820 A2 | 8/2012 |
| WO | 2013064908 A1 | 5/2013 |
| WO | 2014068124 A1 | 5/2014 |
| WO | 2016156128 A1 | 6/2016 |
| WO | 2017095875 A1 | 6/2017 |
| WO | 2020124083 A1 | 6/2020 |
| WO | 2021064327 A1 | 4/2021 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Barreira Da Silva et al., "Dipeptidylpeptidase 4 inhibition enhances lymphocyte trafficking, improving both naturally occurring tumor immunity and immunotherapy," Nature Immunology, 16(8):850-860 (2015).
Llibre et al., "Immune response biomarkers in human and veterinary research," Comparative Immunology, Microbiology and Infectious Diseases, 59:57-62 (2018).
Nishina et al., "Dipeptidyl peptidase 4 (DPP4) inhibitor enhances natural killer cell chemotaxis, improving tumor immunity against hepatocellular carcinoma," Hepatology, 64(1), Suppl., Abstract 467 (Oct. 2016).
Casrouge, A. et al., 'Discrimination of agonist and antagonist forms of CXCL10 in biological samples', Clinical and Experimental Immunology. 2011, vol. 167, pp. 137-148.
Rainczuk, A. et al., 'Evidence for the antagonistic form of CXC-motif chemokine CXCL10 in serous epithelial ovarian tumours', International Journal of Cancer. (published online Jul. 20, 2013) 2014, vol. 134, pp. 530-541.
Loos, T. et al., 'Citrullination of CXCL10 and CXCL11 by peptidylarginine deiminase: a naturally occurring posttranslational modification of chemokines and new dimension of immunoregulation', Blood. 2008, vol. 112, No. 7, pp. 2648-2656.

(Continued)

Primary Examiner — Christine J Saoud
Assistant Examiner — Jon M Lockard
(74) Attorney, Agent, or Firm — Fox Rothschild LLP

(57) ABSTRACT

The present invention relates to C-X-C motif chemokine ligand 10 (CXCL10) binding proteins and uses thereof. The present invention also relates to methods of detecting and/or diagnosing a condition in a subject, comprising determining a level of CXCL10 in the subject.

5 Claims, 15 Drawing Sheets

Specification includes a Sequence Listing.

(56) References Cited

OTHER PUBLICATIONS

Moelants, E.A.V. et al., 'Detection and Quantification of Citrullinated Chemokines', PLoS ONE. 2011, vol. 6, No. 12, e28976, 8 pages.
Meissner, E.G. et al., 'Dynamic Changes of Post-Translationally Modified Forms of CXCL10 and Soluble DPP4 in HCV Subjects Receiving Interferon-Free Therapy', PLoS One. 2015, vol. 10, No. 7, e0133236, 9 pages.
Riva, A. et al., 'Truncated CXCL10 Is Associated With Failure to Achieve Spontaneous Clearance of Acute Hepatitis C Infection', Hepatology. 2014, vol. 60, No. 2, pp. 487-496.
International Search Report for PCT/AU2020/051403 (mailed Jan. 29, 2021), 7 pages.
Al-Lazikani et al., "Standard Conformations for the Canonical Structures of Immunoglobulins", J. Mol. Biol., (1997) 273;927-948.
Armour et al., "Recombinant human IgG molecules lacking Fcg receptor I binding and monocyte triggering activities", Eur. J. Immunol. 1999. 29:2613-2624.
Australian Examination Report mailed Jul. 25, 2022 for Australian Patent Application No. 2020404453, 4 pp.
Australian Examination Report mailed Oct. 11, 2022 for Australian Patent Application No. 2020404453, 7 pp.
Badley et al., "Optical Biosensors for Immunoassays: The Fluorescence Capillary-Fill Device [and Discussion]", Philosophical Transactions of the Royal Society of London. Series B, Biological Sciences, 316(1176):143-160 (Aug. 28, 1987).
Brown et al., "Tolerance of single, but not multiple, amino acid replacements in antibody VH CDR 2: a means of minimizing B cell wastage from somatic hypermutation?", J ImmunolÂ 1996; 156:3285-3291.
Casrouge et al., "Evidence for an antagonist form of the chemokine CXCL10 in patients chronically infected with Hcv", J Clin Invest. 2011; 121(1):308-317.
Chothia et al., "Canonical Structures for the Hypervariable Regions of Immunoglobulins", J. Mol. Biol. (1987) 196:901-917.
Chothia et al., "Conformations of immunoglobulin hypervariable regions", Nature, vol. 342(21/28):877-883 (Dec. 1989).
Dall'acqua et al., "Modulation of the Effector Functions of a Human IgG1 through Engineering of Its Hinge Region", J Immunol 2006; 177:1129-1138.
Edelman et al., "Pillars Article: The Covalent Structure of an Entire gG Immunoglobulin Molecule", Proc. Natl. Acad. Sci. USA, 1969, 63:78-85.
Englebienne et al., "Use of colloidal gold surface plasmon resonance peak shift to infer affinity constants from the interactions between protein antigens and antibodies specific for single or multiple epitopes", Analyst, Jul. 1998, 123:1599-1603.
Gisslén et al., "Plasma Concentration of the Neurofilament Light Protein (NFL) is a Biomarker of CNS Injury in HIV Infection: A Cross-Sectional Study", EBioMedicine 3, 2016, pp. 135-140.
Giudicelli et al., "IMGT, the international ImMunoGene Tics database", Nuclei Acids Research, 1997, vol. 25, No. 1, pp. 206-211.
Hezareh et al., "Effector Function Activities of a Panel of Mutants of a Broadly Neutralizing Antibody against Human Immunodeficiency Virus Type 1", Journal of Virology, Dec. 2001, pp. 12161-12168.
Honegger et al., "The Influence of the Buried Glutamine or Glutamate Residue in Position 6 on the Structure of Immunoglobulin Variable Domains", J. Mol. Biol. (2001) 309:687-699.
International Preliminary Report on Patentability mailed May 17, 2022 in International Application No. PCT/AU2020/051403, 7 pp.
Jones, et al., "A method for rapid, ligation-independent reformatting of recombinant monoclonal antibodies", Journal of Immunological Methods 354 (2010), pp. 85-90.
Jostock et al., "Rapid generation of functional human IgG antibodies derived from Fab-on-phage display libraries", Journal of Immunological Methods 289 (2004), pp. 65-80.
Kopsidas et al., "In vitro improvement of a shark IgNAR antibody by Qß replicase mutation and ribosome display mimics in vivo affinity maturation", Immunology Letters 107 (2006), pp. 163-168.
Kopsidas et al., "RNA mutagenesis yields highly diverse mRNA libraries for in vitro protein evolution", BMC Biotechnology Apr. 11, 2007, 7:18, 12 pp.
Kuhle et al., "Comparison of three analytical platforms for quantification of the neurofilament light chain in blood samples: ELISA, electrochemiluminescence immunoassay and Simoa", Clin Chem Lab Med 2016; 54(10): 1655-1661.
Kyte et al., "A Simple Method for Displaying the Hydropathic Character of a Protein", J. Mol. Biol. (1982) 157, pp. 105-132.
Largaespada et al., "The ABL-MYC retrovirus generates antigen-specific plasmacytomas by in vitro infection of activated B lymphocytes from spleen and other murine lymphoid organs", Journal of Immunological Methods 197 (1996), pp. 85-95.
Mendoza et al., "High-Throughput Microarray-Based Enzyme-Linked Immunosorbent Assay (ELISA)", BioTechniques, 27(4):778-788 (Oct. 1999).
Mortier et al., "Effect of posttranslational processing on the in vitro and in vivo activity of chemokines", Experimental Cell Research. Mar. 10, 2011; 317(5):642-654.
Needleman et al., "A General Method Applicable to the Search for Similarities in the Amino Acid Sequence of Two Proteins", J. Mol. Biol. (1970) 48:443-453.
Novotny et al., "A soluble, single-chain T-cell receptor fragment endowed with antigen-combining properties", Proc Natl Acad Sci USA, vol. 88, Oct. 1991, pp. 8648-8650.
Padlan et al., "Identification of specificity-determining residues in antibodies", FASEB J. Jan. 1995;9(1):133-139.
Raincżuk et al., "The emerging role of CXC chemokines in epithelial ovarian cancer", Reproduction (2012) 144:303-317.
Rich et al., "Advances in surface plasmon resonance biosensor analysis", Current Opinion in Biotechnology 2000, 11:54-61.
Rudikoff et al., "Single amino acid substitution altering antigen-binding specificity", Proc Natl Acad Sci USA, vol. 79, Mar. 1982, pp. 1979-1983.
Scholler et al., "CA125 in Ovarian Cancer", Biomark Med. Dec. 2007; 1(4): 513-523.
Shao et al., "Diagnostic and prognostic significance of serum CD26 level in Asian women with high-grade serous ovarian carcinoma", Future Oncol. (2019) 15(16):1863-1871.
Shields et al., High Resolution Mapping of the Binding Site on Human IgG1 for FcgRI, FcgRII, FcgRIII, and FcRn and Design of IgG1 Variants with Improved Binding to the FcgR, The Journal of Biological Chemistry, vol. 276, No. 9, Issue of March 2, pp. 6591-6604, 2001.
Sinnathurai et al., "Circulating Fibroblast Activation Protein and Dipeptidyl Peptidase 4 in Rheumatoid Arthritis and Systemic Sclerosis", Int J Rheum Dis. Nov. 2018; 21(11):1915-1923.
Stemmer, "Rapid evolution of a protein in vitro by DNA shuffling", Letters To Nature, 370:389-391 (Aug. 1994).
Thie et al., "Affinity Maturation by Phage Display", Therapeutic Antibodies: Methods and Protocols, vol. 525, Chapter 16, Methods Mol Biol. 2009, pp. 309-322.
Vuento et al., "Significance of a Single CA 125 Assay Combined with Ultrasound in the Early Detection of Ovarian and Endometrial Cancer", Gynecologic Oncology 64, 1997, pp. 141-146.
Windmüller et al., "CXCR3 mediates ascites-directed tumor cell migration and predicts poor outcome in ovarian cancer patients", Oncogenesis (2017) 6, 9 pp.
Winkler et al., "Changing the Antigen Binding Specificity by Single Point Mutations of an Anti-p24 (HIV-1) Antibody", J. Immunol 2000; 165:4505-4514.
Zhang et al., "Expression levels of seprase/FAPa and DPPIV/CD26 in epithelial ovarian carcinoma", Oncology Letters 10: 2015; pp. 34-42.
Vanheule et al., "How post-translational modifications influence the biological activity of chemokines," Cytokine, 109:29-54 (2018).
Ragab et al., "CXCL10 antagonism and plasma sDPPIV correlate with increasing liver disease in chronic HCV genotype 4 infected patients," Cytokine, 63:105-112 (2013).
Proost et al., "Chemokine isoforms and processing in inflammation and immunity," Journal of Autoimmunity, 85:45-57 (2017).

* cited by examiner

CXCL10 BINDING PROTEINS AND USES THEREOF

RELATED APPLICATION DATA

The present application is a continuation of U.S. patent application Ser. No. 17/783,528 filed Jun. 8, 2022 (now U.S. Pat. No. 11,725,048), which is a U.S. national stage application under 35 U.S.C. §371 of International Application No. PCT/AU2020/051403 filed Dec. 18, 2020, which claims priority to Australian Patent Application No. 2019904859 entitled "CXCL10 binding proteins and uses thereof" filed on Dec. 20, 2019, the entire contents of all of which are hereby incorporated by reference.

SEQUENCE LISTING

The sequence listing of the present application is submitted electronically as a computer readable sequence listing in XML format with a file name of "180037.00711.xml", a creation date of Jun. 26, 2023, and a size of 33,501 bytes. This submitted sequence listing is part of the specification and hereby incorporated by reference in its entirety.

FIELD OF THE INVENTION

The present disclosure relates to CXCL10 binding proteins and uses thereof.

BACKGROUND OF THE INVENTION

The chemokine interferon-γ inducible protein (also known as C-X-C motif chemokine ligand 10; CXCL10; interferon-induced protein-10 or IP-10) is a member of the CXC chemokine family and plays a significant role in leukocyte trafficking by producing chemotactic activity in cells expressing corresponding chemokine receptors.

CXCL10 has both agonistic and antagonistic activities and is involved in chemotaxis, induction of apoptosis, and regulation of cell growth and mediation of angiostatic effects. CXCL10 exerts its biological effects by specifically activating a receptor, CXCR3, which is a seven transmembrane-spanning G protein-coupled receptor predominantly expressed on activated T lymphocytes (Th1), natural killer (NK) cells, inflammatory dendritic cells, macrophages and B cells. The proliferative or anti-proliferative action of CXCL10 appears to be cell-type-dependent and/or dependent on the subtype of its receptor CXCR3. Furthermore, posttranslational modifications such as deamination or citrullination of CXCL10 by peptidylarginine deiminases (PAD) or $NH_2$-terminal truncation by proteases such as dipeptidylpeptidase IV (DPP4), contribute to its biological effects by generating dominant negative forms which are capable of binding CXCR3 but do not induce signalling.

CXCL10 has been associated with a variety of human diseases including infectious diseases, central nervous system disorders, chronic inflammation, immune dysfunction and cancer.

Given its widespread association with numerous human disorders, CXCL10 has been an attractive biomarker and candidate for targeted therapy. However, the application of commercially available diagnostics has been limited due to their inability to discriminate between different biologically relevant forms of the protein.

It will be clear to the skilled artisan based on the foregoing that there is a need in the art for compounds (e.g., antibodies and antibody-derived proteins) that can accurately target all forms of CXCL10 as a potential biomarker.

SUMMARY OF THE INVENTION

In producing the present invention, the inventors sought to produce reagents that bind to biologically relevant forms of CXCL10. The inventors produced an antibody that binds full-length (i.e., biologically active) CXCL10 as well as an antibody that binds full-length CXCL10 in addition to N-terminally truncated and citrullinated (i.e., inactive) forms. Surprisingly, the inventors found that detecting the different forms of CXCL10, and in particular the ratio of the different forms of CXCL10, was able to discriminate between benign and malignant conditions. The inventors also found that the ratio of the different forms of CXCL10 was able to distinguish the presence of disease (either benign or malignant) from an absence of disease (i.e., healthy individuals). The inventors also surprisingly found that detecting the ratio of the different forms of CXCL10 in combination with other biological markers (e.g., DPP4, CA-125, GM-CSF, IL-6, TNF-RII, HE4 and/or IL-8) was able to discriminate between stage I (i.e., early stage) cancers or pre-cancerous lesions and benign conditions.

In one example, the present disclosure provides a CXCL10 binding protein, wherein the binding protein binds to full-length human CXCL10, N-terminally truncated CXCL10 and citrullinated CXCL10.

In an embodiment of the above example, the CXCL10 binding protein binds the epitope NH2-LSRTVRCTCISIS-NQPVNPRSLE-COOH (SEQ ID NO: 26) of full-length human CXCL10, N-terminally truncated CXCL10 and citrullinated CXCL10.

In one example, the CXCL10 binding protein (i) binds to full-length human CXCL10 with a $K_D$ of 50 nM or less; and/or (ii) binds to N-terminally truncated human CXCL10 with a $K_D$ of 5 nM or less.

In one example, the CXCL10 binding protein binds to or specifically binds to full-length human CXCL10 with a $K_D$ of 50 nM or less. For example, the CXCL10 binding protein binds to or specifically binds to full-length human CXCL10 with a $K_D$ of about 50 nM, or about 40 nM, or about 30 nM, or about 20 nM, or about 10 nM. In one example, the CXCL10 binding protein binds to or specifically binds to full-length human CXCL10 with a $K_D$ of about 49 nM.

In an embodiment of the above example, the CXCL10 binding protein requires the N-terminal valine and/or proline of the epitope NH2-VPLSRTVRCTCISISNQPVNPRSLE-COOH (SEQ ID NO: 25) to bind to full-length human CXCL10.

In one example, the CXCL10 binding protein binds to or specifically binds to N-terminally truncated human CXCL10 with a $K_D$ of 5 nM or less. For example, the CXCL10 binding protein binds to or specifically binds to N-terminally truncated human CXCL10 with a $K_D$ of about 5 nM, or about 4 nM, or about 3 nM, or about 2 nM, or about 1 nM. In one example, the CXCL10 binding protein binds to or specifically binds to N-terminally truncated CXCL10 with a $K_D$ of about 3 nM.

The present disclosure also provides a CXCL10 binding protein, wherein the binding protein binds to full-length human CXCL10 with a $K_D$ of 50 nM or less, but does not bind N-terminally truncated CXCL10 and citrullinated CXCL10.

In one example, the CXCL10 binding protein does not detectably bind or does not significantly bind N-terminally truncated CXCL10 and citrullinated CXCL10.

Methods for determining binding of a CXCL10 binding protein to a polypeptide will be apparent to the skilled artisan. For example, the polypeptide is immobilized on a solid or semi-solid surface and the CXCL10 binding protein is contacted to the immobilized polypeptide. Binding is then determined, e.g., by surface plasmon resonance (SPR) imaging.

In one example, the level of binding (e.g., as determined by $K_D$) is measured by surface plasmon resonance (SPR) imaging.

In one example, the CXCL10 binding protein of the present disclosure comprises a variable region or an antigen binding domain.

In one example, the binding protein is selected from the group consisting of:
(i) a Fv;
(ii) a single chain Fv fragment (scFv);
(iii) a dimeric scFv (di-scFv);
(iv) a single-domain antibody;
(v) a minibody;
(vi) a diabody;
(vii) a triabody;
(viii) a tetrabody;
(ix) a Fab;
(x) a F(ab')2;
(xi) an antibody;
(xii) an antibody mimetic;
(xiii) a heavy chain only immunoglobulin;
(xiv) a T-cell receptor;
(xv) an adnectin;
(xvi) an anticalin;
(xvii) an affibody;
(xviii) an avimer;
(xix) a designed ankyrin-repeat protein (DARPin); and
(xx) one of (i) to (xix) linked to a constant region of an antibody, Fc or a heavy chain constant domain (CH) 2 and/or CH3.

In one example, the binding protein comprises an antigen binding domain of an antibody. For example, the binding protein comprises at least a $V_H$ and a $V_L$, wherein the $V_H$ and $V_L$ bind to form a Fv comprising an antigen binding domain.

In one example, the binding protein is an antibody or antigen binding fragment thereof (e.g., a scFv comprising the variable regions of the antibody). Exemplary antibodies are full-length and/or naked (e.g., unconjugated) antibodies. In one example, an antibody of the present disclosure is a full length antibody.

In one example, the antibody is an IgG or an IgE or an IgM or an IgD or an IgA or an IgY antibody. For example, the antibody is an IgG antibody.

In one example, the IgG antibody is an $IgG_1$ or an $IgG_2$ or an $IgG_3$ or an $IgG_4$. For example, the antibody is an $IgG_1$ antibody. In another example, the antibody is an $IgG_4$ antibody. In one example, the antibody is a stabilized $IgG_4$ antibody.

In one example, the binding protein is recombinant, chimeric, CDR grafted, humanized, synhumanized, primatized, deimmunized or human.

In one example, the antigen binding fragment of the present disclosure is a half antibody.

For example, the CXCL10 binding protein is a half antibody comprising a single heavy chain and a single light chain.

In one example, the antigen binding fragment of the present disclosure comprises an $IgG_4$ constant region or a stabilised $IgG_4$ constant region.

In one example, the binding protein is an antibody mimetic. For example, the binding protein comprises an antigen binding domain of an immunoglobulin, e.g., an IgNAR, a camelid antibody or a T cell receptor.

In one example, the binding protein is a domain antibody (e.g., comprising only a heavy chain variable region or only a light chain variable region) or a heavy chain only antibody (e.g., a camelid antibody or IgNAR) or variable region thereof.

In one example, the binding protein competitively inhibits the binding of an antibody or antigen binding fragment thereof to CXCL10 comprising:
(i) a heavy chain variable region ($V_H$) comprising an amino acid sequence set forth in SEQ ID NO: 3 and a light chain variable region ($V_L$) comprising an amino acid sequence set forth in SEQ ID NO: 4; and/or
(ii) a $V_H$ comprising an amino acid sequence set forth in SEQ ID NO: 11 and a $V_L$ Comprising an amino acid sequence set forth in SEQ ID NO: 12.

In one example, the binding protein competitively inhibits the binding of an antibody or antigen binding fragment thereof to CXCL10 comprising a $V_H$ comprising an amino acid sequence set forth in SEQ ID NO: 3 and a $V_L$ comprising an amino acid sequence set forth in SEQ ID NO: 4.

In another example, the binding protein competitively inhibits the binding of an antibody or antigen binding fragment thereof to CXCL10 comprising a $V_H$ comprising an amino acid sequence set forth in SEQ ID NO: 11 and a $V_L$ comprising an amino acid sequence set forth in SEQ ID NO: 12.

In one example, the binding protein comprises:
(i) a $V_H$ comprising a sequence which is at least 90% identical to a sequence set forth in SEQ ID NO: 3 and a $V_L$ comprising a sequence which is at least 90% identical to a sequence set forth in SEQ ID NO: 4; or
(ii) a $V_H$ comprising a sequence which is at least 90% identical to a sequence set forth in SEQ ID NO: 11 and a $V_L$ comprising a sequence which is at least 90% identical to a sequence set forth in SEQ ID NO: 12.

In one example, the binding protein comprises a $V_H$ comprising a sequence which is at least 90% identical to a sequence set forth in SEQ ID NO: 3 and a $V_L$ comprising a sequence which is at least 90% identical to a sequence set forth in SEQ ID NO: 4. For example, the binding protein comprises a $V_H$ and/or a $V_L$ which is at least 90% or 95% or 97% or 98% or 99% identical to a sequence disclosed herein.

In one example, the binding protein comprises a $V_H$ comprising a sequence which is at least 90% identical to a sequence set forth in SEQ ID NO: 11 and a $V_L$ Comprising a sequence which is at least 90% identical to a sequence set forth in SEQ ID NO: 12. For example, the binding protein comprises a $V_H$ and/or a $V_L$ which is at least 90% or 95% or 97% or 98% or 99% identical to a sequence disclosed herein.

In one example, the binding protein of the present disclosure optionally comprises one or more amino acid substitutions, deletions or insertions of any sequence disclosed herein. Amino acid substitutions suitable for use in the present disclosure will be apparent to the skilled person and include naturally-occurring substitutions and engineered substitutions.

In one example, the CXCL10 binding protein of the present disclosure is an antibody or antigen binding fragment thereof comprising:
(i) a $V_H$ comprising an amino acid sequence set forth in SEQ ID NO: 3 and a $V_L$ comprising an amino acid sequence set forth in SEQ ID NO: 4; or (ii) a $V_H$ comprising an amino acid sequence set forth in SEQ ID NO: 11 and a $V_L$ comprising an amino acid sequence set forth in SEQ ID NO: 12.

In one example, the CXCL10 binding protein of the present disclosure is an antibody or antigen binding fragment thereof comprising a $V_H$ comprising an amino acid sequence set forth in SEQ ID NO: 3 and a $V_L$ comprising an amino acid sequence set forth in SEQ ID NO: 4.

In another example, the CXCL10 binding protein of the present disclosure is an antibody or antigen binding fragment thereof comprising a $V_H$ comprising an amino acid sequence set forth in SEQ ID NO: 11 and a $V_L$ comprising an amino acid sequence set forth in SEQ ID NO: 12.

In one example, the CXCL10 binding protein of the present disclosure is an antibody or antigen binding fragment thereof comprising:
(i) a $V_H$ comprising:
  a) a CDR1 comprising a sequence set forth in amino acids 25-34 of SEQ ID NO: 3; and
  b) a CDR2 comprising a sequence set forth in amino acids 49-65 of SEQ ID NO: 3; and
  c) a CDR3 comprising a sequence set forth in amino acids 98-108 of SEQ ID NO: 3; and
  a $V_L$ comprising:
  a) a CDR1 comprising a sequence set forth in amino acids 23-33 of SEQ ID NO: 4; and
  b) a CDR2 comprising a sequence set forth in amino acids 49-55 of SEQ ID NO: 4; and
  c) a CDR3 comprising a sequence set forth in amino acids 88-96 of SEQ ID NO: 4; or
(ii) a $V_H$ comprising:
  a) a CDR1 comprising a sequence set forth in amino acids 25-34 of SEQ ID NO: 11; and
  b) a CDR2 comprising a sequence set forth in amino acids 49-65 of SEQ ID NO: 11; and
  c) a CDR3 comprising a sequence set forth in amino acids 98-108 of SEQ ID NO: 11; and
  a $V_L$ comprising:
  a) a CDR1 comprising a sequence set forth in amino acids 23-33 of SEQ ID NO: 12; and
  b) a CDR2 comprising a sequence set forth in amino acids 49-55 of SEQ ID NO: 12; and
  c) a CDR3 comprising a sequence set forth in amino acids 88-96 of SEQ ID NO: 12.

In one example, the CXCL10 binding protein of the present disclosure is an antibody or antigen binding fragment thereof comprising:
(i) a $V_H$ comprising:
  a) a CDR1 comprising a sequence set forth in amino acids 25-34 of SEQ ID NO: 3; and
  b) a CDR2 comprising a sequence set forth in amino acids 49-65 of SEQ ID NO: 3; and
  c) a CDR3 comprising a sequence set forth in amino acids 98-108 of SEQ ID NO: 3; and
(ii) a $V_L$ comprising:
  a) a CDR1 comprising a sequence set forth in amino acids 23-33 of SEQ ID NO: 4; and
  b) a CDR2 comprising a sequence set forth in amino acids 49-55 of SEQ ID NO: 4; and
  c) a CDR3 comprising a sequence set forth in amino acids 88-96 of SEQ ID NO: 4.

In one example, the CXCL10 binding protein of the present disclosure is an antibody or antigen binding fragment thereof comprising:
(i) a $V_H$ comprising:
  a) a CDR1 comprising a sequence set forth in amino acids 25-34 of SEQ ID NO: 11; and
  b) a CDR2 comprising a sequence set forth in amino acids 49-65 of SEQ ID NO: 11; and
  c) a CDR3 comprising a sequence set forth in amino acids 98-108 of SEQ ID NO: 11; and
(ii) a $V_L$ comprising:
  a) a CDR1 comprising a sequence set forth in amino acids 23-33 of SEQ ID NO: 12; and
  b) a CDR2 comprising a sequence set forth in amino acids 49-55 of SEQ ID NO: 12; and
  c) a CDR3 comprising a sequence set forth in amino acids 88-96 of SEQ ID NO: 12.

In one example, the CXCL10 binding protein of the present disclosure is an antibody or antigen binding fragment thereof comprising:
(i) a $V_H$ comprising
  a) a CDR1 comprising a sequence set forth in SEQ ID NO: 5; and
  b) a CDR2 comprising a sequence set forth in SEQ ID NO: 6; and
  c) a CDR3 comprising a sequence set forth in SEQ ID NO: 7; and
  a $V_L$ comprising:
  a) a CDR1 comprising a sequence set forth in SEQ ID NO: 8; and
  b) a CDR2 comprising a sequence of DTS; and
  c) a CDR3 comprising a sequence set forth in SEQ ID NO: 10; or
(ii) a $V_H$ comprising
  a) a CDR1 comprising a sequence set forth in SEQ ID NO: 13; and
  b) a CDR2 comprising a sequence set forth in SEQ ID NO: 14; and
  c) a CDR3 comprising a sequence set forth in SEQ ID NO: 15; and
  a $V_L$ comprising:
  a) a CDR1 comprising a sequence set forth in SEQ ID NO: 16; and
  b) a CDR2 comprising a sequence of LAS; and
  c) a CDR3 comprising a sequence set forth in SEQ ID NO: 18.

In one example, the CXCL10 binding protein of the present disclosure is an antibody or antigen binding fragment thereof comprising:
(i) a $V_H$ comprising
  a) a CDR1 comprising a sequence set forth in SEQ ID NO: 5; and
  b) a CDR2 comprising a sequence set forth in SEQ ID NO: 6; and
  c) a CDR3 comprising a sequence set forth in SEQ ID NO: 7; and
(ii) a $V_L$ comprising:
  a) a CDR1 comprising a sequence set forth in SEQ ID NO: 8; and
  b) a CDR2 comprising a sequence of DTS; and
  c) a CDR3 comprising a sequence set forth in SEQ ID NO: 10.

In one example, the CXCL10 binding protein of the present disclosure is an antibody or antigen binding fragment thereof comprising:
(i) a $V_H$ comprising
  a) a CDR1 comprising a sequence set forth in SEQ ID NO: 13; and
  b) a CDR2 comprising a sequence set forth in SEQ ID NO: 14; and
  c) a CDR3 comprising a sequence set forth in SEQ ID NO: 15; and (ii) a $V_L$ comprising:
  a) a CDR1 comprising a sequence set forth in SEQ ID NO: 16; and
  b) a CDR2 comprising a sequence of LAS; and
  c) a CDR3 comprising a sequence set forth in SEQ ID NO: 18.

In one example, the protein, antibody or antigen binding fragment thereof is any form of the protein, antibody or functional fragment thereof encoded by a nucleic acid encoding any of the foregoing proteins, antibodies or functional fragments.

In one example, the CXCL10 binding protein is conjugated to a detectable label. Detectable labels suitable for use in the present disclosure will be apparent to the skilled person and/or are described herein. For example, the detectable label is selected from the group consisting of a radiolabel, an enzyme, a fluorescent label, a luminescent label, a bioluminescent label, a magnetic label, a prosthetic group and a contrast agent.

In one example, the detectable label is a radiolabel. For example, the radiolabel can be, but is not limited to, radioiodine (125I, 131I); technetium; yttrium; 35S or 3H.

In one example, the detectable label is an enzyme. For example, the enzyme can be, but is not limited to, horseradish peroxidase, alkaline phosphatase, β-galactosidase, or acetylcholinesterase.

In one example, the detectable label is a fluorescent label. For example, the fluorescent label can be, but is not limited to, umbelliferone, fluorescein, fluorescein isothiocyanate, rhodamine, dichlorotriazinylamine fluorescein, dansyl chloride or phycoerythrin.

In one example, the detectable label is a luminescent label. For example, the luminescent label can be, but is not limited to, luminol.

In one example, the detectable label is a bioluminescent label. For example, the bioluminescent label can be, but is not limited to, luciferase, luciferin or aequorin.

In one example, the detectable label is a magnetic label. For example, the magnetic label can be, but is not limited to, gadolinium or iron-oxide chelate.

In one example, the detectable label is a prosthetic group. For example, the prosthetic group can be, but is not limited to, streptavidin/biotin or avidin/biotin.

In one example, the detectable label is a contrast agent.

The present disclosure also provides a composition comprising the binding protein of the present disclosure and a carrier. Carriers suitable for use in the present disclosure will be apparent to the skilled person and/or are described herein.

The present disclosure also provides a polynucleotide encoding the CXCL10 binding protein according to the present disclosure.

The present disclosure further provides an expression vector comprising the polynucleotide encoding the CXCL10 binding protein of the present disclosure. Exemplary vectors suitable for use in the present disclosure will be apparent to the skilled person and/or are described herein.

The present disclosure further provides a cell comprising the expression vector of the present disclosure in vitro. Exemplary cells suitable for use in the present disclosure will be apparent to the skilled person and/or are described herein. In one example, the present disclosure provides use of the cell for preparing a CXCL10 binding protein of the present disclosure. For example, the use comprises culturing the cell of the disclosure and producing the CXCL10 binding protein therefrom; and isolating and purifying the produced binding protein. Methods of isolating and purifying the produced binding protein will be apparent to the skilled person and/or are described herein.

The present disclosure provides a method of detecting and/or diagnosing a malignant condition in a subject, the method comprising:
  a) determining a level of active CXCL10 in the subject and a level of total CXCL10 in the subject; and
  b) determining a CXCL10 ratio of active CXCL10 to total CXCL10 in the subject.

In one example, determining the level of active CXCL10 and total CXCL10 comprises determining the amount of active CXCL10 protein and the amount of total CXCL10 protein in the subject.

In one example, the method further comprises comparing the CXCL10 ratio in the subject to a CXCL10 ratio in at least one reference. Methods of determining a reference will be apparent to the skilled person and/or are described herein.

In one example, the method comprises determining (a) if the CXCL10 ratio in the subject is higher than the CXCL10 ratio in the reference, or (b) if the CXCL10 ratio in the subject is lower than the CXCL10 ratio in the reference.

In one example, (i) a lower CXCL10 ratio in the subject compared to the CXCL10 ratio in the reference is indicative of the malignant condition; or (ii) a higher CXCL10 ratio in the subject compared to the CXCL10 ratio in the reference is indicative of a benign condition.

In one example, the method comprises using:
  (i) a CXCL10 binding protein that specifically binds full-length human CXCL10 and N-terminally truncated CXCL10 and citrullinated CXCL10 to determine the level of total CXCL10 in the subject; and
  (ii) a CXCL10 binding protein that specifically binds full-length human CXCL10, but does not bind N-terminally truncated CXCL10 and citrullinated CXCL10 to determine the level of active CXCL10 in the subject.

In one example of any method described herein, the method comprises using at least one CXCL10 binding protein according to the present disclosure.

In one example,
  (i) the level of total CXCL10 in the subject is determined using an antibody or antigen binding fragment thereof comprising a $V_H$ comprising an amino acid sequence set forth in SEQ ID NO: 11 and a $V_L$ comprising an amino acid sequence set forth in SEQ ID NO: 12; and/or
  (ii) the level of active CXCL10 in the subject is determined using an antibody or antigen binding fragment thereof comprising a $V_H$ comprising an amino acid sequence set forth in SEQ ID NO: 3 and a $V_L$ comprising an amino acid sequence set forth in SEQ ID NO: 4.

In one example, the level of total CXCL10 in the subject is determined using an antibody or antigen binding fragment thereof comprising a $V_H$ comprising an amino acid sequence set forth in SEQ ID NO: 11 and a $V_L$ comprising an amino acid sequence set forth in SEQ ID NO: 12.

In another example, the level of active CXCL10 in the subject is determined using an antibody or antigen binding fragment thereof comprising a $V_H$ comprising an amino acid sequence set forth in SEQ ID NO: 3 and a $V_L$ comprising an amino acid sequence set forth in SEQ ID NO: 4.

In one example, one or more of the CXCL10 binding proteins is conjugated to a detectable label. Detectable labels suitable for use in the present disclosure will be apparent to the skilled person and/or are described herein. For example, the detectable label is selected from the group consisting of a radiolabel, an enzyme, a fluorescent label, a luminescent label, a bioluminescent label, a magnetic label, a prosthetic group and a contrast agent.

In one example, the detectable label is a radiolabel. For example, the radiolabel can be, but is not limited to, radioiodine (125I, 131I); technetium; yttrium; 35S or 3H.

In one example, the detectable label is an enzyme. For example, the enzyme can be, but is not limited to, horseradish peroxidase, alkaline phosphatase, 0-galactosidase, or acetylcholinesterase.

In one example, the detectable label is a fluorescent label. For example, the fluorescent label can be, but is not limited to, umbelliferone, fluorescein, fluorescein isothiocyanate, rhodamine, dichlorotriazinylamine fluorescein, dansyl chloride or phycoerythrin.

In one example, the detectable label is a luminescent label. For example, the luminescent label can be, but is not limited to, luminol.

In one example, the detectable label is a bioluminescent label. For example, the bioluminescent label can be, but is not limited to, luciferase, luciferin or aequorin.

In one example, the detectable label is a magnetic label. For example, the magnetic label can be, but is not limited to, gadolinium or iron-oxide chelate.

In one example, the detectable label is a prosthetic group. For example, the prosthetic group can be, but is not limited to, streptavidin/biotin or avidin/biotin.

In one example, the detectable label is a contrast agent.

Methods of detecting the level of CXCL10 will be apparent to the skilled person and/or described herein. For example, the method comprises performing flow cytometry, an enzyme-linked immunosorbent assay or western blot.

In one example, the method comprises performing flow cytometry.

In one example, the method comprises performing an enzyme-linked immunosorbent assay.

In one example, the method comprises performing western blot.

In one example, the method is performed on the subject in vitro or ex vivo. For example, the method is performed on the subject in vitro. In another example, the method is performed on the subject ex vivo.

In one example, the method is performed on at least one biological sample obtained from the subject. Suitable biological samples for use in the present disclosure will be apparent to the skilled person and/or are described herein. For example, the biological sample is selected from the group consisting of a biopsy, a fluid sample, a plasma sample or cellular swab.

In one example, the biological sample is a biopsy.

In one example, the biological sample is a fluid sample. For example, the fluid sample is cervical fluid, vaginal fluid or ascites. In one example, the biological sample is ascites fluid.

In one example, the biological sample is a plasma sample.

In one example, the biological sample is a cellular swab. For example, the cellular swab is a cervical swab. In one example, the cellular swab is a cervicovaginal swab (CVS).

In one example, the method is performed on a plasma sample and a cervicovaginal swab (CVS).

In one example of any method described herein, the invention provides a method of detecting and/or diagnosing a malignant condition in a subject. For example, the malignant condition is a reproductive cancer. In one example, the reproductive cancer is ovarian cancer. In one example, the ovarian cancer is a stage I cancer. In another example, the ovarian cancer is a pre-cancerous lesion, for example a lesion with a p53 gene mutation.

In one example, the method comprises detecting and/or diagnosing a malignant condition from a benign condition.

In one example of any method described herein, the method further comprises determining the level of dipeptidyl peptidase-4 (DPP4) and/or cancer antigen 125 (CA-125) in the subject. In one example, the method further comprises determining the level of dipeptidyl peptidase-4 (DPP4) and cancer antigen 125 (CA-125) in the subject. In another example, the method further comprises determining the level of dipeptidyl peptidase-4 (DPP4) in the subject. In a further example, the method further comprises determining the level of cancer antigen 125 (CA-125) in the subject.

In one example of any method described herein, the method further comprises determining the level of one or more or all of granulocyte-macrophage colony-stimulating factor (GM-CSF), interleukin 6 (IL-6), tumor necrosis factor receptor II (TNF-RII), human epididymis protein 4 (HE4) and interleukin 8 (IL-8). For example, the method further comprises determining the level of GM-CSF, IL-6, TNF-RII, HE4 and IL-8.

In one example of any method described herein, the method further comprises determining the level of DPP4, GM-CSF, IL-6, TNF-RII, HE4 and IL-8.

In one example of any method described herein, the method further comprises determining the level of CA-125, GM-CSF, IL-6, TNF-RII, HE4 and IL-8.

In one example of any method described herein, the method further comprises determining the level of DPP4, CA-125, GM-CSF, IL-6, TNF-RII, HE4 and IL-8.

Also provided is a method of detecting and/or diagnosing a condition in a subject, the method comprising determining a level of CXCL10 in the subject using at least one CXCL10 binding protein of the invention.

In this example the condition is one that is characterized by the level, and/or relative ratio, of one or more of full-length (i.e., biologically active) CXCL10, N-terminally truncated CXCL10 and citrullinated CXCL10. In one example, the condition is an inflammatory condition. For example, the inflammatory condition is arthritis, such as rheumatoid arthritis and/or psoriatic arthritis. In one example, the condition is rheumatoid arthritis. In another example, the condition is psoriatic arthritis. In one example, the condition is hepatitis C. In another example, the condition is heart failure.

The present disclosure also provides a method of monitoring tumour burden in a subject suffering from a malignant condition, the method comprising determining a CXCL10 ratio of active CXCL10 to total CXCL10 in the subject at one or more time points.

The present disclosure further provides a method of monitoring progression of a malignant condition in a subject, the method comprising determining a CXCL10 ratio of active CXCL10 to total CXCL10 in the subject at one or more time points.

The present disclosure also provides a method of determining tumour regression in a subject suffering from a malignant condition, the method comprising determining a CXCL10 ratio of active CXCL10 to total CXCL10 in the subject at one or more time points.

The present disclosure also provides a method of determining tumour recurrence in a subject suffering from a malignant condition, the method comprising determining a CXCL10 ratio of active CXCL10 to total CXCL10 in the subject at one or more time points.

The present disclosure also provides a method of determining efficacy of a treatment for a malignant condition in a subject suffering from the malignant condition, the method comprising determining a CXCL10 ratio of active CXCL10 to total CXCL10 in the subject at one or more time points.

In one example, the subject has been diagnosed as having a malignant condition. For example, the subject is suffering from a malignant condition. For example, the malignant condition is a reproductive cancer, such as ovarian cancer.

In one example, the subject is asymptomatic.

In one example, the subject has not received treatment for the malignant condition. For example, the subject is treatment naive. In one example, the subject is receiving treatment for the malignant condition. In another example, the subject has received treatment for the malignant condition. Suitable therapies for the treatment of the malignant condition will be apparent to the skilled person and/or described herein. For example, the treatment comprises surgery, chemotherapy, radiation therapy, targeted drug therapy, immunotherapy or a combination thereof.

In one example, the treatment comprises surgery.

In one example, the treatment comprises chemotherapy.

In one example, the treatment comprises radiation therapy.

In one example, the treatment comprises targeted drug therapy.

In one example, the treatment comprises immunotherapy.

In one example, the method comprises determining:
(a) if the CXCL10 ratio in the subject at the subsequent time point is lower than the CXCL10 ratio in the subject at the first time point; or
(b) if the CXCL10 ratio in the subject at the subsequent time point is higher than the CXCL10 ratio in the subject at the first time point.

In one example, a lower CXCL10 ratio in the subject at the subsequent time point compared to the first time point is indicative of increased tumour burden and/or tumour progression and/or tumour recurrence in the subject. For example, a CXCL10 ratio in the subject after treatment (i.e., at the subsequent time point) compared to before treatment (i.e., the first time point) is indicative of increased tumour burden and/or tumour progression and/or tumour recurrence in the subject.

In one example, a higher CXCL10 ratio in the subject at the subsequent time point compared to the first time point is indicative of reduced tumour burden and/or tumour regression and/or tumour recurrence in the subject. For example, a higher CXCL10 ratio in the subject after treatment (i.e., at the subsequent time point) compared to before treatment (i.e., the first time point) is indicative of reduced tumour burden and/or tumour regression and/or tumour recurrence in the subject.

In one example of any method described herein, the method further comprises administering a treatment to reduce the tumour burden and/or tumour progression in the subject.

The present disclosure further provides a method of treating a malignant condition in a subject, the method comprising detecting and/or diagnosing a malignant condition in the subject according to the disclosure, and administering a treatment to the subject.

Suitable therapies for the treatment of a malignant condition will be apparent to the skilled person and/or described herein. For example, the treatment comprises surgery, chemotherapy, radiation therapy, targeted drug therapy, immunotherapy or a combination thereof.

The present disclosure also provides a panel or kit for detecting and/or diagnosing the malignant condition in a subject, the panel or kit comprising one or more CXCL10 binding proteins of the present disclosure.

The present disclosure further provides a panel or kit for monitoring tumour burden, monitoring progression, determining tumour regression, determining tumour recurrence and/or determining efficacy of a treatment of a malignant condition in a subject, the panel or kit comprising one or more CXCL10 binding proteins of the present disclosure.

Any embodiment herein shall be taken to apply mutatis mutandis to any other embodiment unless specifically stated otherwise. For instance, as the skilled person would understand, examples outlined above for one example of the invention equally apply to other examples the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

BRIEF DESCRIPTION OF FIGURES

FIG. 4A shows active CXCL10 concentrations in benign (n=51) and malignant ascites (n=208): 240.4±410.5 pg/mL and 818.6±1098.0 pg/mL, respectively; and FIG. 4B shows total CXCL10 concentrations in benign (n=51) and malignant ascites (n=212): 160.8±362.0 pg/mL and 1126.1±2158.6 pg/mL, respectively. FIG. 4C shows significant difference in active ratios between benign (n=51) and malignant ascites (n=226): 2.59±1.18 and 1.43±1.04, respectively. FIG. 4D shows active ratios based on the stages of ovarian cancer in comparison with benign. Benign: 2.59±1.18; stage 1: 1.07±0.44; and stage 3: 1.55+1.23. ****P<0.0001.

FIG. 5A shows measurement of DPP4 concentrations in benign (n=48) and malignant ascites (n=148) by anti-DPP4 ELISA; 184.8±177.6 ng/mL and 203.5±154.3 ng/mL, respectively. P=0.1031. FIG. 5B shows measurement of DPP4 specific activities (U/ng) in benign (n=49) and malignant (n=50) ascites; 2.49±3.83 and 1.65±2.13, respectively. P=0.4229. FIG. 5C shows measurement of plasma CA125 in the matching patients: 200.8±368.7 U/mL and 1697.0±3409.0 U/mL for benign (n=30) and malignant (n=188) patient samples, respectively. ****P≤0.0001.

FIG. 6A shows no significant correlations between active ratio and plasma CA125 in either benign or malignant samples. FIG. 6B shows moderate, negative correlation between active ratio and DPP4 (ng/mL) in malignant ascites samples (P=0.0002) while no significant correlation in benign samples. FIG. 6C shows moderate, negative correlation between active ratio and DPP4 specific activity (U/ng) in benign samples (P=0.0895) while no correlation in malignant samples.

FIG. 7A shows zctive ratio achieving higher AUC (0.8617) than AUC of quantitation of total CXCL10 and active CXCL10 (AUC 0.8122 and 0.7872, respectively); FIG. 7B shows active ratio achieving higher AUC than AUC of DPP4 and plasma CA125 (AUC 0.5598 and AUC 0.8262, respectively). Demonstration of highest AUC by combining active ratio, DPP4 (ng/mL), and plasma CA125 (U/mL).

FIG. 8A shows significant difference in active ratio in CVS between benign (n=50) and malignant (n=50) samples: active ratios in benign and malignant CVS; 4.39±4.52 and 1.14±0.62, respectively. FIG. 8B shows significant difference in active ratio in plasma between benign (n=30) and malignant (n=30) plasma samples: active ratios in benign and malignant plasma; 3.18±1.79 and 2.02±1.05 respectively. **P<0.0001, P<0.01.

FIG. 9A shows active and total CXCL10 concentrations measured in plasma samples. FIG. 9B shows active and total CXCL10 concentrations across the three patient groups. FIG. 9C shows calculated active ratio between cancer-free (healthy) samples and benign and malignant samples detected in plasma. FIG. 9D shows calculated active ratio between cancer-free (healthy) samples and benign and malignant samples detected in CVS. * p<0.05; ****p<0.0001.

FIG. 11A shows the overall concentration of active CXCL10 was significantly higher than total CXCL10. FIG. 11B shows calculated active ratio between cancer-free (healthy) samples and benign and malignant samples. * p<0.05; ****p<0.0001.

KEY TO SEQUENCE LISTING

Figure 1:
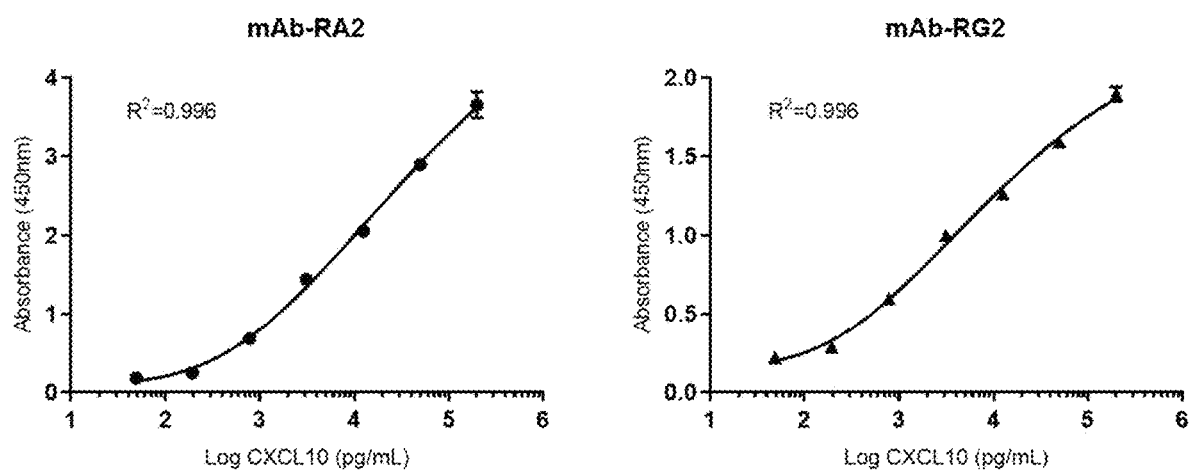
FIG. 1—Graphical representation showing differentiation between active and total CXCL10. Representative standard curves using RA2 and RG2 for the detection of CXCL10, respectively with $R^2 > 0.99$.

SEQ ID NO: 1 amino acid sequence of human CXCL10 including pre-sequence
SEQ ID NO: 2 amino acid sequence of mature human CXCL10
SEQ ID NO: 3 heavy chain $V_H$ amino acid sequence of anti-CXCL10 antibody RA2
SEQ ID NO: 4 light chain $V_L$ amino acid sequence of anti-CXCL10 antibody RA2
SEQ ID NO: 5 heavy chain $V_H$ CDR1 amino acid sequence of anti-CXCL10 antibody RA2
SEQ ID NO: 6 heavy chain $V_H$ CDR2 amino acid sequence of anti-CXCL10 antibody RA2
SEQ ID NO: 7 heavy chain $V_H$ CDR3 amino acid sequence of anti-CXCL10 antibody RA2
SEQ ID NO: 8 light chain $V_L$ CDR1 amino acid sequence of anti-CXCL10 antibody RA2
DTS (Asp Thr Ser) light chain $V_L$ CDR2 amino acid sequence of anti-CXCL10 antibody RA2
SEQ ID NO: 10 light chain $V_L$ CDR3 amino acid sequence of anti-CXCL10 antibody RA2
SEQ ID NO: 11 heavy chain $V_H$ amino acid sequence of anti-CXCL10 antibody RG2
SEQ ID NO: 12 light chain $V_L$ amino acid sequence of anti-CXCL10 antibody RG2
SEQ ID NO: 13 heavy chain $V_H$ CDR1 amino acid sequence of anti-CXCL10 antibody RG2
SEQ ID NO: 14 heavy chain $V_H$ CDR2 amino acid sequence of anti-CXCL10 antibody RG2
SEQ ID NO: 15 heavy chain $V_H$ CDR3 amino acid sequence of anti-CXCL10 antibody RG2

SEQ ID NO: 16 light chain $V_L$ CDR1 amino acid sequence of anti-CXCL10 antibody RG2 LAS (Leu Ala Ser) light chain $V_L$ CDR2 amino acid sequence of anti-CXCL10 antibody RG2

SEQ ID NO: 18 light chain $V_L$ CDR3 amino acid sequence of anti-CXCL10 antibody RG2

SEQ ID NO: 19 heavy chain $V_H$ nucleotide sequence of anti-CXCL10 antibody RA2

SEQ ID NO: 20 light chain $V_L$ nucleotide acid sequence of anti-CXCL10 antibody RA2

SEQ ID NO: 21 heavy chain $V_H$ nucleotide sequence of anti-CXCL10 antibody RG2

SEQ ID NO: 22 light chain $V_L$ nucleotide acid sequence of anti-CXCL10 antibody RG2

SEQ ID NO: 23 peptide sequence comprising the intact N-terminus of human CXCL10

SEQ ID NO: 24 peptide sequence comprising the truncated N-terminus of human CXCL10

SEQ ID NO: 25 Intact N-terminus epitope of human CXCL10

SEQ ID NO: 26 Truncated N-terminus epitope of human CXCL10

DETAILED DESCRIPTION OF THE INVENTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

The present disclosure is not to be limited in scope by the specific examples described herein, which are intended for the purpose of exemplification only. Functionally-equivalent products, compositions and methods are clearly within the scope of the present disclosure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Any example of the present disclosure herein shall be taken to apply mutatis mutandis to any other example of the disclosure unless specifically stated otherwise. Stated another way, any specific example of the present disclosure may be combined with any other specific example of the disclosure (except where mutually exclusive).

Any example of the present disclosure disclosing a specific feature or group of features or method or method steps will be taken to provide explicit support for disclaiming the specific feature or group of features or method or method steps.

Unless specifically defined otherwise, all technical and scientific terms used herein shall be taken to have the same meaning as commonly understood by one of ordinary skill in the art (for example, in cell culture, molecular genetics, molecular biology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, Perbal, 1984; Sambrook et al., 1989; Brown, 1991; Glover et al., 1995 and 1996; Ausubel et al., 1988; Harlow et al., 1988; Coligan et al., 1991.

The description and definitions of variable regions and parts thereof, immunoglobulins, antibodies and fragments thereof herein may be further clarified by the discussion in Kabat et al., 1987 and 1991; Bork et al., 1994; Chothia and Lesk, 1987; Chothia et al., 1989 and/or Al-Lazikani et al., 1997.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

The term "and/of", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "subject" shall be taken to mean any animal including humans, for example a mammal. Exemplary subjects include but are not limited to humans and non-human primates. For example, the subject is a human.

Selected Definitions

Human CXCL10 is expressed as a pre-sequence (SEQ ID NO: 1), with the N-terminal 22 amino acids cleaved to produce mature "full length" human CXCL10 (SEQ ID NO: 2). Thus, as used herein, the term "full-length CXCL10" refers to CXCL10 which has not been modified post-translationally other than the post-translational cleavage to remove the 22 N-terminal amino acids to produce "mature" full-length CXCL10.

As used herein, the term "N-terminally truncated CXCL10" refers to "mature" full-length CXCL10 which has been truncated by dipeptidylpeptidase IV (DPP4) and consists of e.g., amino acids 3 to 77 of SEQ ID NO: 2.

As used herein, the term "citrullinated CXCL10" refers to CXCL10 which has been post-translationally modified by deamination or citrullination at an arginine residue at e.g., amino acid position 5 of SEQ ID NO: 2, by peptidylarginine deiminases (PAD).

The sequence of CXCL10 from other species can be determined using sequences provided herein and/or in publicly available databases and/or determined using standard techniques (e.g., as described in Ausubel et al., 1988 (including all updates until present) or Sambrook et al., 1989).

The term "recombinant" shall be understood to mean the product of artificial genetic recombination. Accordingly, in the context of a recombinant protein comprising a variable region or an antigen binding domain (e.g., an antibody antigen binding domain), this term does not encompass naturally-occurring protein within a subject's body that is the product of natural recombination that occurs during B cell maturation. However, if such a protein is isolated, it is to be considered an isolated protein comprising a variable region or an antigen binding domain. Similarly, if nucleic acid encoding the protein is isolated and expressed using recombinant means, the resulting protein is a recombinant protein comprising a variable region or an antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "binding protein" shall be understood to refer to a protein or part thereof or other region of the protein that is capable of interacting with or specifically binding to an antigen (e.g., a cell component or molecule, such as a protein).

As used herein, the term "antigen binding domain" shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., CXCL10) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kDa) covalently linked and two light chains (~23 kDa each). A light chain generally comprises a variable region (if present) and a constant domain and in mammals is either a x light chain or a k light chain. A heavy chain generally comprises a variable region and one or two constant domain(s) linked by a hinge region to additional constant domain(s). Heavy chains of mammals are of one of the following types: α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies.

Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulphide-bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity-determining regions (CDRs); i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain ($V_H$ or $V_L$) typically has three CDRs identified as CDR1, CDR2 and CDR3. In one example, the amino acid positions assigned to CDRs and FRs are defined according to Kabat et al., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FR1), 24 to 34 (CDR1), 35 to 49 (FR2), 50 to 56 (CDR2), 57 to 88 (FR3), 89 to 97 (CDR3) and 98 to 107 (FR4). The present disclosure is not limited to FRs and CDRs as defined by the Kabat numbering system, but includes all numbering systems, including the canonical numbering system or of Chothia and Lesk, 1987; Chothia et al., 1989; and/or Al-Lazikani et al., 1997; the numbering system of Honnegher and Pliikthun, 2001; or the IMGT system discussed in Giudicelli et al., 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In this regard, Padlan et al., 1995 established that the five C-terminal amino acids of heavy chain CDR2 are not generally involved in antigen binding.

"Framework regions" (FRs) are those variable region residues other than the CDR residues.

As used herein, the term "Fv" (or variable fragment) shall be taken to mean any protein, whether comprised of multiple polypeptides or a single polypeptide, in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. An "antigen binding fragment" or "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a CXCL10 binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a CXCL10 binding protein of the disclosure reacts or associates more frequently, more rapidly, with greater duration and/or with greater affinity with a particular antigen or cell expressing same than it does with alternative antigens or cells. For example, a CXCL10 binding protein binds to CXCL10 with materially greater affinity (e.g., 1.5 fold or 2 fold or 5 fold or 10 fold or 20 fold or fold or 60 fold or 80 fold to 100 fold or 150 fold or 200 fold) than it does to other chemokine receptors or to antigens commonly recognized by polyreactive natural antibodies (i.e., by naturally occurring antibodies known to bind a variety of antigens naturally found in humans). Reference to "binding" provides explicit support for the term "specific binding" and vice versa.

As used herein, the term "does not bind" shall be understood to mean that a CXCL10 binding protein of the present disclosure does not bind to a particular antigen or cell expressing same.

As used herein, the term "does not detectably bind" shall be understood to mean that a CXCL10 binding protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. In one example, the level of binding is detected using biosensor analysis (e.g. Biacore) in which the antigen (e.g., a polypeptide) is immobilized and contacted with a CXCL10 binding protein.

As used herein, the term "does not significantly bind" shall be understood to mean that the level of binding of a CXCL10 binding protein of the disclosure to a polypeptide is not statistically significantly higher than background, e.g., the level of binding signal detected in the absence of the CXCL10 binding protein and/or in the presence of a negative control protein (e.g., an isotype control antibody) and/or the level of binding detected in the presence of a negative control polypeptide. In one example, the level of binding is detected using biosensor analysis (e.g. Biacore) in which the antigen (e.g., a polypeptide) is immobilized and contacted with a CXCL10 binding protein.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

As used herein, the term "epitope" (syn. "antigenic determinant") shall be understood to mean a region to which a CXCL10 binding protein binds. This term is not necessarily limited to the specific residues or structure to which the CXCL10 binding protein makes contact. For example, this term includes a region spanning amino acids contacted by the CXCL10 binding protein and 5-10 (or more) or 2-5 or 1-3 amino acids outside of this region. In some examples, the epitope comprises a series of discontinuous amino acids that are positioned close to one another when a CXCL10 polypeptide is folded and, for example, associated with another CXCL10 polypeptide, i.e., a "conformational epitope".

The term "competitively inhibits" shall be understood to mean that a CXCL10 binding protein of the disclosure (or an antigen binding domain thereof) reduces or prevents binding of a recited antibody or CXCL10 binding protein to CXCL10. This maybe due to the CXCL10 binding protein (or antigen binding domain) and antibody binding to the same or an overlapping epitope. It will be apparent from the foregoing that the CXCL10 binding protein need not completely inhibit binding of the antibody, rather it need only reduce binding by a statistically significant amount, for example, by at least about 10% or 20% or 30% or 40% or 50% or 60% or 70% or 80% or 90% or 95%. For example, the CXCL10 binding protein reduces binding of the antibody by at least about 30%, for example by at least about 50%, such as, by at least about 70%, for example by at least about 75%, even more preferably, by at least about 80% or 85% e.g., by at least about 90%. Methods for determining competitive inhibition of binding are known in the art and/or described herein. For example, the antibody is exposed to CXCL10 either in the presence or absence of the CXCL10 binding protein. If less antibody binds in the presence of the CXCL10 binding protein than in the absence of the CXCL10 binding protein, the protein is considered to competitively inhibit binding of the antibody. In one example, the competitive inhibition is not due to steric hindrance.

CXCL10 Binding Proteins

As discussed herein, binding proteins of the present disclosure can take various forms and bind to full-length human CXCL10, N-terminally truncated CXCL10 and/or citrullinated CXCL10.

In one example, the present disclosure provides a CXCL10 binding protein, wherein the binding protein binds to full-length human CXCL10, N-terminally truncated CXCL10 and citrullinated CXCL10.

In another example, the present disclosure provides a CXCL10 binding protein, wherein the binding protein binds to full-length human CXCL10, but does not bind N-terminally truncated CXCL10 and citrullinated CXCL10.

Antibodies

In one example, a CXCL10 binding protein of the present disclosure comprises an antibody or antigen binding fragment thereof.

Immunization-Based Methods

Methods for generating antibodies are known in the art and/or described in Harlow et al., 1988. Generally, in such methods a protein or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow et al., 1988.

For example, a suitable animal is immunized with an immunogen under conditions sufficient to stimulate antibody producing cells. Rabbits and rodents such as mice and rats are exemplary animals. Mice genetically-engineered to express human immunoglobulin proteins and, for example, do not express murine immunoglobulin proteins, can also be used to generate an antibody of the present disclosure (e.g., as described in WO2002066630).

Following immunization, somatic cells with the potential for producing antibodies, e.g., B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison WI 53713, USA) is used to produce cell lines secreting mAbs (e.g., as described in Largaespada et al., 1996).

Library-Based Methods

The present disclosure also encompasses screening of libraries of antibodies or antigen binding fragments thereof (e.g., comprising variable regions thereof).

Examples of libraries contemplated by this disclosure include naive libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook et al., 2001) and used to encode and display proteins using a method known in the art. Other techniques for producing libraries of proteins are described in, for example in U.S. Pat. No. 6,300,064 (e.g., a HuCAL library of Morphosys AG); U.S. Pat. Nos. 5,885,793; 6,204,023; 6,291,158; or U.S. Pat. No. 6,248,516.

The antigen binding fragments according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding fragments of antibodies are expressed on phage, e.g., as described in U.S. Pat. Nos. 6,300,064; 5,885,793; 6,204,023; 6,291,158; or U.S. Pat. No. 6,248,516. Other phage display methods are known in the art and are contemplated by the present disclosure. Similarly, methods of cell display are contemplated by the disclosure, e.g., bacterial display libraries, e.g., as described in U.S. Pat. No. 5,516,637; yeast display libraries, e.g., as described in U.S. Pat. No. 6,423,538 or a mammalian display library.

Methods for screening display libraries are known in the art. In one example, a display library of the present disclosure is screened using affinity purification, e.g., as described in Scopes, 1994. Methods of affinity purification typically involve contacting proteins comprising antigen binding fragments displayed by the library with a target antigen and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., 2010; or Jostock et al., 2004; or WO2012040793. Alternatively, or additionally, standard cloning methods are used, e.g., as described in Ausubel et al., 1987, and/or Sambrook et al., 2001.

Deimmunized, Chimeric, Humanized, Synhumanized, Primatized and Human Antibodies or Antigen Binding Fragments The antibodies or antigen binding fragments of the present disclosure may be may be humanized.

The term "humanized antibody" shall be understood to refer to a protein comprising a human-like variable region, which includes CDRs from an antibody from a non-human species (e.g., mouse or rat or non-human primate) grafted onto or inserted into FRs from a human antibody (this type of antibody is also referred to a "CDR-grafted antibody"). Humanized antibodies also include antibodies in which one or more residues of the human protein are modified by one or more amino acid substitutions and/or one or more FR residues of the human antibody are replaced by corresponding non-human residues. Humanized antibodies may also comprise residues which are found in neither the human antibody or in the non-human antibody. Any additional regions of the antibody (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized antibody" also encompasses a super-humanized antibody, e.g., as described in U.S. Pat. No. 7,732,578. A similar meaning will be taken to apply to the term "humanized antigen binding fragment".

The antibodies or antigen binding fragments thereof of the present disclosure may be human antibodies or antigen binding fragments thereof. The term "human antibody" as used herein refers to antibodies having variable and, optionally, constant antibody regions found in humans, e.g. in the human germline or somatic cells or from libraries produced using such regions. The "human" antibodies can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. For the purposes of the present disclosure, a human antibody will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516. A similar meaning will be taken to apply to the term "human antigen binding fragment".

The antibodies or antigen binding fragments thereof of the present disclosure may be synhumanized antibodies or antigen binding fragments thereof. The term "synhumanized antibody" refers to an antibody prepared by a method described in WO2007019620. A synhumanized antibody includes a variable region of an antibody, wherein the variable region comprises FRs from a New World primate antibody variable region and CDRs from a non-New World primate antibody variable region.

The antibody or antigen binding fragment thereof of the present disclosure may be primatized. A "primatized antibody" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

In one example an antibody or antigen binding fragment thereof of the disclosure is a chimeric antibody or fragment. The term "chimeric antibody" or "chimeric antigen binding fragment" refers to an antibody or fragment in which one or more of the variable domains is from a particular species (e.g., murine, such as mouse or rat) or belonging to a particular antibody class or subclass, while the remainder of the antibody or fragment is from another species (such as, for example, human or non-human primate) or belonging to another antibody class or subclass. In one example, a chimeric antibody comprising a $V_H$ and/or a $V_L$ from a non-human antibody (e.g., a murine antibody) and the remaining regions of the antibody are from a human antibody. The production of such chimeric antibodies and antigen binding fragments thereof is known in the art, and may be achieved by standard means (as described, e.g., in U.S. Pat. Nos. 6,331,415; 5,807,715; 4,816,567 and 4,816,397).

The present disclosure also contemplates a deimmunized antibody or antigen binding fragment thereof, e.g., as described in WO2000034317 and WO2004108158. Deimmunized antibodies and fragments have one or more epitopes, e.g., B cell epitopes or T cell epitopes removed (i.e., mutated) to thereby reduce the likelihood that a subject will raise an immune response against the antibody or protein. For example, an antibody of the disclosure is analyzed to identify one or more B or T cell epitopes and one or more amino acid residues within the epitope is mutated to thereby reduce the immunogenicity of the antibody.

Antibody Binding Domain Containing Proteins

Single-Domain Antibodies

In some examples, a CXCL10 binding protein of the disclosure is or comprises a single-domain antibody (which is used interchangeably with the term "domain antibody" or "dAb"). A single-domain antibody is a single polypeptide chain comprising all or a portion of the heavy chain variable domain of an antibody.

Diabodies, Triabodies, Tetrabodies

In some examples, a CXCL10 binding protein of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv) Fragments

The CXCL10 binding protein of the disclosure can be a scFv. The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Half-Antibodies

In some examples, the antigen binding fragment of the present disclosure is a half-antibody or a half-molecule. The skilled artisan will be aware that a half-antibody refers to a protein comprising a single heavy chain and a single light chain. The term "half-antibody" also encompasses a protein comprising an antibody light chain and an antibody heavy chain, wherein the antibody heavy chain has been mutated to prevent association with another antibody heavy chain. In one example, a half-antibody forms when an antibody dissociates to form two molecules each containing a single heavy chain and a single light chain.

Methods for generating half-antibodies are known in the art and exemplary methods are described herein.

In one example, the half-antibody can be secreted by introducing into cells genes of the single heavy chain and single light chain that constitute the IgG of interest for expression. In one example, a constant region (e.g., an $IgG_4$ constant region) comprises a "key or hole" (or "knob or hole") mutation to prevent heterodimer formation. In one example, a constant region (e.g., an $IgG_4$ constant region) comprises a T366W mutation (or knob). In another example, a constant region (e.g., an $IgG_4$ constant region) comprises a T366S, L368A and Y407V mutation (or hole). In another example, the constant region comprises T350V, T366L, K392L and T394W mutations (knob). In another example, the constant region comprises T350V, L351Y, F405A and Y407V mutations (hole). Exemplary constant region amino acid substitutions are numbered according to the EU numbering system.

Other Antibodies and Proteins Comprising Antigen Binding Domains Thereof

The present disclosure also contemplates other antibodies and proteins comprising antigen-binding domains thereof, such as:
 (i) minibodies, e.g., as described in U.S. Pat. No. 5,837,821;
 (ii) heteroconjugate proteins, e.g., as described in U.S. Pat. No. 4,676,980;
 (iii) heteroconjugate proteins produced using a chemical cross-linker, e.g., as described in U.S. Pat. No. 4,676,980; and
 (iv) $Fab_3$ (e.g., as described in EP19930302894).

Immunoglobulins and Immunoglobulin Fragments

An example of a CXCL10 binding protein of the present disclosure is a protein comprising a variable region of an immunoglobulin, such as a T cell receptor or a heavy chain immunoglobulin (e.g., an IgNAR, a camelid antibody).

Heavy Chain Immunoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble.

A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005118629.

V-Like Proteins

In one example, a CXCL10 binding protein of the present disclosure comprises a T-cell receptor. T cell receptors have two V-domains that combine into a structure similar to the Fv module of an antibody. Novotny et al., 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999045110 or WO2011107595.

Other non-antibody proteins comprising antigen binding domains include proteins with V-like domains, which are generally monomeric. Examples of proteins comprising such V-like domains include CTLA-4, CD28 and ICOS.

Further disclosure of proteins comprising such V-like domains is included in WO1999045110.

Adnectins

In one example, a CXCL10 binding protein of the present disclosure comprises an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005056764.

Anticalins

In a further example, a CXCL10 binding protein of the disclosure comprises an anticalin. Anticalins are derived from lipocalins, which are a family of extracellular proteins which transport small hydrophobic molecules such as steroids, bilins, retinoids and lipids. Lipocalins have a rigid j-sheet secondary structure with a plurality of loops at the open end of the conical structure which can be engineered to bind to an antigen. Such engineered lipocalins are known as anticalins. For further description of anticalins see U.S. Pat. No. 7,250,297 or US20070224633.

Affibodies

In a further example, a CXCL10 binding protein of the disclosure comprises an affibody. An affibody is a scaffold derived from the Z domain (antigen binding domain) of Protein A of 15 *Staphylococcus aureus* which can be engineered to bind to antigen. The Z domain consists of a three-helical bundle of approximately 58 amino acids. Libraries have been generated by randomization of surface residues. For further details see EP1641818.

Avimers

In a further example, a CXCL10 binding protein of the disclosure comprises an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO2002088171.

DARPins

In a further example, a CXCL10 binding protein of the disclosure comprises a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Mutations to Binding Proteins

The present disclosure also provides a CXCL10 binding protein or a nucleic acid encoding same having at least 90% identity to a sequence disclosed herein. In one example, a CXCL10 binding protein or nucleic acid of the disclosure comprises sequence at least about 90% or 95% or 97% or 98% or 99% identical to a sequence disclosed herein, wherein the protein specifically binds to CXCL10 as described herein according to any example.

Alternatively, or additionally, the CXCL10 binding protein comprises a CDR (e.g., three CDRs) at least about 90% or 95% or 97% or 98% or 99% identical to CDR(s) of a $V_H$ or $V_L$ as described herein according to any example, wherein the protein is capable of specifically binding to CXCL10 as described herein according to any example. Methods for determining binding of a protein to CXCL10 are described herein.

It is known in the art that the five C-terminal residues of heavy chain CDR2 can be mutated to conservative or non-conservative amino acid substitutions (31% of residues) (Padlan et al., 1995). Thus, a protein can comprise a CDR2 having at least about 35% identity to a heavy chain CDR2 sequence disclosed herein.

The present disclosure also contemplates mutant forms of a CXCL10 binding protein of the disclosure comprising one or more conservative amino acid substitutions compared to a sequence set forth herein. In some examples, the CXCL10 binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity. Exemplary conservative amino acid substitutions are provided in Table 1.

TABLE 1

Exemplary amino acid substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle, 1982 and hydrophylic indices are described in, e.g., U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the CXCL10 binding protein comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of a CXCL10 binding protein of the disclosure. In another example, the mutation(s) occur within a CDR of a CXCL10 binding protein of the disclosure.

Exemplary methods for producing mutant forms of a CXCL10 binding protein include:

mutagenesis of DNA (Thie et al., 2009) or RNA (Kopsidas et al., 2006; Kopsidas et al., 2007; and WO1999/058661);

introducing a nucleic acid encoding the polypeptide into a mutator cell, e.g., XL-1Red, XL-mutS and XL-mutS-Kanr bacterial cells (Stratagene);

DNA shuffling, e.g., as disclosed in Stemmer, 1994; and site directed mutagenesis, e.g., as described in Dieffenbach et al., 1995).

Exemplary methods for determining biological activity of the mutant CXCL10 binding proteins of the disclosure will be apparent to the skilled artisan and include, for example antigen binding, competitive inhibition of binding, affinity, association and dissociation.

In another example, a nucleic acid of the disclosure comprises a sequence at least about 90% or 95% or 97% or 98% or 99% identical to a sequence set forth herein and encoding a CXCL10 binding protein having a function as described herein according to any example. The present disclosure also encompasses nucleic acids encoding a CXCL10 binding protein of the disclosure, which differs from a sequence exemplified herein as a result of degeneracy of the genetic code.

The % identity of a nucleic acid or polypeptide is determined by GAP (Needleman and Wunsch, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

Constant Regions

The present disclosure encompasses CXCL10 binding proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region. In an embodiment, the constant region is an IgG kappa constant region.

In one example, the Fc region of the constant region has a reduced ability to induce effector function, e.g., compared to a native or wild-type human IgG1 or IgG3 Fc region. In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity (CDC); antibody-dependent-cell-mediated cytotoxicity (ADCC); antibody-dependent-cell-phagocytosis (ADCP); and B-cell activation. In one example, the effector function is ADCC and/or ADCP and/or CDC. Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., 1987 and/or 1991). This position corresponds to position 228 of the hinge region according to the EU numbering system (Kabat et al., 2001 and Edelman et al., 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulfide (S-S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., 1999; Shields et al., 2001).

Additional examples of non-immunostimulatory Fc regions are described, for example, in Dall'Acqua et al., 2006; and/or Hezareh, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Protein Production

In one example, a CXCL10 binding protein described herein according to any example is produced by culturing a cell of the invention under conditions sufficient to produce the protein, e.g., as described herein and/or as is known in the art.

Recombinant Expression

In another example, a CXCL10 binding protein described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., 1988 (including all updates until present) or Sambrook et al., 1989. A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *Schizosaccharomyces pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMl-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a CXCL10 binding protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The CXCL10 binding protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Harlow et al., 1988.

The skilled artisan will also be aware that a protein can be modified to include a tag to facilitate purification or detection, e.g., a poly-histidine tag, e.g., a hexa-histidine tag, or an influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

In one example, a CXCL10 binding protein of the present disclosure is conjugated to a detectable label.

As used herein, the term "conjugate" or "conjugated" shall be understood to encompass both indirect and direct binding. For example, direct conjugation includes chemical conjugation, which can be non-covalent or covalent or genetic conjugation (also referred to as "fusion"). In one example, the conjugation is covalent, e.g., a disulphide bond.

As used herein, a "detectable label" is a molecular or atomic tag or marker that generates or can be induced to generate an optical or other signal or product that can be detected visually or by using a suitable detector. Detectable labels are well known in the art and include, for example, a radiolabel, an enzyme, a fluorescent label, a luminescent label, a bioluminescent label, a magnetic label, a prosthetic group, a contrast agent and an ultrasound agent.

Fluorescent labels commonly used include Alexa, cyanine such as Cy5 and Cy5.5, and indocyanine, and fluorescein isothiocyanate (FITC), but they are not so limited. Fluorescent labels useful in the practice of the present disclosure can include, also without limitation, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6C; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange+DNA; Acridine Orange+RNA; Acridine Orange, both DNA & RNA; Acridine Red; Acridine Yellow; Acriflavin; Acriflavin Feulgen SITSA; Aequorin (Photoprotein); Alexa Fluor 350; Alexa Fluor 430; Alexa Fluor 488; Alexa Fluor 532; Alexa Fluor 546; Alexa Fluor 568; Alexa Fluor 594; Alexa Fluor 633; Alexa Fluor 647; Alexa Fluor 660; Alexa Fluor 680; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC=Ratio Dye, $Zn^{2+}$; APTS; Astrazon Brilliant Red 4G; Astrazon Orange R; Astrazon Red 6B; Astrazon Yellow 7 GLL; Atabrine; ATTO-TAG CBQCA; ATTO-TAG FQ; Auramine; Aurophosphine G; Aurophosphine; BAO 9 (Bisamninophenyloxadiazole); BCECF (high pH); BCECF (low pH); Berberine Sulphate; Beta Lactamase; BFP blue shifted GFP (Y66H); Blue Fluorescent Protein; BFP/GFP FRET Bimane; Bisbenzamnide; Bisbenzimide (Hoechst); bis-BTC=Ratio Dye, $Zn^{2+}$; Blancophor FFG; Blancophor SV; BOBO-1; BOBO-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO-1; BO-PRO-3; Brilliant Sulphoflavin FF; BTC-Ratio Dye $Ca^{2+}$; BTC-5Natio Dye, $Zn^{2+}$; Calcein; Calcein Blue; Calcium Crimson; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue; Cascade Yellow 399; Catecholamine; CCF2 (GeneBlazer); CFDA; CFP-Cyan Fluorescent Protein; CFP/YFP; FRET; Chlorophyll; Chromomycin A; Chromomycin A; CL-NERF (Ratio Dye, pH); CMFDA; Coelenterazine; Coelenterazine cp ($Ca^{2+}$ Dye); Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2; Cy3.18; Cy3.5; Cy3; Cy5.18; Cy5.5; Cy5; Cy7; Cyan GFP; cyclic AMP Fluorosensor (FiCRhR); CyQuant Cell Proliferation Assay; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrohodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; Red fluorescent protein; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; FITC Antibody; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43; FM 4-46; Fura Red (high pH); Fura Red/Fluo-3; Fura-2, high calcium; Fura-2, low calcium; Fura-2/BCECF; Genacryl Brilliant Red B; Genacryl Brilliant Yellow I0GF; Genacryl Pink 3G; Genacryl Yellow 5GF; GeneBlazer (CCF2); GFP (S65T); GFP red shifted (rsGFP), GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; LIVE/DEAD Kit Animal Cells, Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue, LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green; Oregon Green 488; Oregon Green 500; Oregon Greene 514; Pacific Blue; Pararosaniline (Feulgen); PBFI; PE-Cy5; PE-Cy7; PerCP; PerCP-Cy5.5; PE-Texas-Red [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodide (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP; sgBFP (super glow BFP); sgGFP; sgGFP (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYT; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (Tetramethyl-Rodamine-IsoThioCyanate); True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3.

In one example, a detectable label is an enzyme. The enzyme can act on an appropriate substrate to result in production of a detectable dye. Examples of enzymes useful in the disclosure include, without limitation, alkaline phosphatase and horseradish peroxidase. Alternatively or in addition, the enzyme can be, for example, luciferase. The enzyme can be linked to the antibody by conventional chemical methods, or it can be expressed together with the antibody as a fusion protein.

Radioisotopes useful as detectable labels in the disclosure are well known in the art and can include $^3$H, $^{11}$C, $^{18}$F, 35S, $^{64}$Cu, $^{67}$Ga, $^{68}$Ga, $^{99}$mTc, $^{111}$In, $^{123}$I, $^{124}$I, $^{125}$I, and $^{131}$I. Attachment of any gamma emitting radioactive materials, e.g., $^{99}$mTc and $^{111}$In, which can react with carboxyl, amino, or sulfhydryl groups of a compound that binds calcitonin receptor is suitable for use in detection methods using gamma scintigraphy. Attachment of radioactive $^{11}$C, $^{18}$F, $^{64}$Cu, $^{67}$Ga, $^{68}$Ga, $^{124}$I, and $^{131}$I compounds which can react with carboxyl, amino, or sulfhydryl groups of a compound is suitable for use in detection methods using PET/SPECT imaging.

Assaying CXCL10 Binding Proteins

Binding to CXCL10 and Modified Forms Thereof

It will be apparent to the skilled artisan from the disclosure herein that some CXCL10 binding proteins of the present disclosure bind to full-length CXCL10 and/or to specific post-translationally modified forms of CXCL10 (e.g., N-terminally truncated CXCL10 and/or citrullinated CXCL10). Methods for assessing binding to a protein are known in the art, e.g., as described in Scopes, 1994. Such a method generally involves immobilizing the CXCL10 binding protein and contacting it with labeled antigen. Following washing to remove non-specific bound protein, the amount of label and, as a consequence, bound antigen is detected. Of course, the CXCL10 binding protein can be labeled and the antigen immobilized. Panning-type assays can also be used. Alternatively, or additionally, surface plasmon resonance assays can be used.

Determining Affinity

Optionally, the dissociation constant (Kd) or association constant (Ka) or equilibrium constant ($K_D$) of a binding protein is determined. These constants for a binding region (e.g., an antibody or antigen binding fragment) are, in one example, measured by biosensor analysis using surface plasmon resonance assays. Exemplary SPR methods are described in U.S. Pat. No. 7,229,619.

Affinity measurements can be determined by standard methodology for antibody reactions, for example, immunoassays, surface plasmon resonance (SPR) (Rich and Myszka, 2000; Englebienne, 1998), isothermal titration calorimetry (ITC) or other kinetic interaction assays known in the art.

Determining Competitive Binding

Assays for determining an antibody or antigen binding fragment thereof that competitively inhibits binding of a CXCL10 binding protein described herein will be apparent to the skilled artisan and/or described herein.

For example, the antibody or antigen binding fragment thereof is conjugated to a detectable label, e.g., a fluorescent label or a radioactive label. The labeled antibody and the test CXCL10 binding protein are then mixed and contacted with CXCL10 or a region thereof or a cell expressing same. The level of labeled antibody is then determined and compared to the level determined when the labeled antibody is contacted with the CXCL10, region or cells in the absence of the CXCL10 binding protein. If the level of labeled antibody is reduced in the presence of the test CXCL10 binding protein compared to the absence of the CXCL10 binding protein, the CXCL10 binding protein is considered to competitively inhibit binding of the antibody to CXCL10.

Optionally, the test CXCL10 binding protein is conjugated to different label to the antibody. This alternate labeling permits detection of the level of binding of the test CXCL10 binding protein to CXCL10 or the region thereof or the cell.

In another example, the CXCL10 binding protein is permitted to bind to CXCL10 or a region thereof or a cell expressing same prior to contacting the CXCL10, region or cell with the antibody. A reduction in the amount of bound antibody in the presence of the CXCL10 binding protein compared to in the absence of the CXCL10 binding protein indicates that the protein competitively inhibits binding of the antibody to CXCL10. A reciprocal assay can also be performed using labeled CXCL10 binding protein and first allowing the antibody to bind to CXCL10. In this case, a reduced amount of labeled CXCL10 binding protein bound to CXCL10 in the presence of the antibody compared to in the absence of the antibody indicates that the CXCL10 binding protein competitively inhibits binding of the antibody to CXCL10.

Determining the Level of CXCL10

As discussed above, CXCL10 has been associated with a variety of human diseases including infectious diseases, central nervous system disorders, chronic inflammation, immune dysfunction and cancer.

The present inventors have developed CXCL10 binding proteins to detect different forms of the protein, i.e., full-length or mature CXCL10, N-terminally truncated CXCL10 and/or citrullinated CXCL10.

The present inventors have found that different forms of the protein are present at different levels in benign and malignant conditions.

Accordingly, the methods of any disclosure described herein comprise determining a level of CXCL10 in a subject.

As used herein, the term "level" in reference to CXCL10 shall be understood to refer to the level of functionality of the protein (i.e., the functional level). For example, the level (or "level of expression") refers to a measure of encoded protein.

In particular, the inventors have found that determining the level of active CXCL10 protein and total CXCL10 protein in a subject can distinguish benign and malignant conditions. This procedure is referred to herein as the active ratio test (ART).

As used herein, the term "active" in the context of the level of CXCL10 refers to biologically active forms of CXCL10. For example, a CXCL10 binding protein of the present disclosure that binds active CXCL10 refers to a binding protein that binds to full-length or mature (i.e., N-terminally intact) CXCL10 but does not bind to N-terminally truncated or citrullinated CXCL10.

As used herein, the term "total" in the context of the level of CXCL10 refers to all forms of CXCL10. For example, a CXCL10 binding protein of the present disclosure that binds total CXCL10 refers to a binding protein that binds to full-length or mature (i.e., N-terminally intact) CXCL10 as well as to N-terminally truncated and citrullinated CXCL10.

In one example, determining the level of active CXCL10 and total CXCL10 comprises determining the amount of active CXCL10 protein and the amount of total CXCL10 protein in the subject.

As used herein, the term "amount" with reference to the level of CXCL10 will be understood to refer to a quantity of protein (i.e., either active or total CXCL10). Various methods of assessing the quantity of protein are available to the skilled person and the skilled person will recognise that the specific value or amount will vary depending on the method of assessment used. It will also be apparent that this term encompasses both an absolute and relative value. For example, the amount may be relative to a reference or control sample. In another example, the amount may be an absolute value of the amount of protein present in the sample.

The inventors have surprisingly found that determining the CXCL10 ratio in a subject can distinguish benign and malignant conditions.

As used herein, the term "CXCL10 ratio" refers to the ratio of the level of active CXCL10 to the level of total CXCL10 in the subject.

In one example, the method further comprises comparing the CXCL10 ratio in the subject to a CXCL10 ratio in at least one reference.

In one example of any method described herein, the method comprises determining (a) if the CXCL10 ratio in the subject is higher than the CXCL10 ratio in the reference, or (b) if the CXCL10 ratio in the subject is lower than the CXCL10 ratio in the reference.

The term "higher" in reference to the CXCL10 ratio means that the ratio in the subject is greater or increased, compared to a control or reference level. It will be apparent from the foregoing that the CXCL10 ratio needs only be increased by a statistically significant amount, for example, by at least about 10%, or about 20%, or about 30%, or about 40%, or about 50%, or about 60%, or about 70%, or about 80%, or about 90%, or about 95%.

The term "lower" in reference to the CXCL10 ratio means that the ratio in the subject is reduced or decreased, compared to a control or reference level. It will be apparent from the foregoing that the CXCL10 ratio need only be decreased by a statistically significant amount, for example, by at least about 10%, or about 20%, or about 30%, or about 40%, or about 50%, or about 60%, or about 70%, or about 80%, or about 90%, or about 95%.

Methods of Determining the Level of CXCL10

Methods of determining the level of CXCL10 protein will be apparent to the skilled person and/or are described herein. For example, methods include immunohistochemistry, immunofluorescence, an immunoblot, a western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology. For example, a suitable assay is a semi-quantitative assay and/or a quantitative assay.

In one example, the method for determining the level of CXCL10 in a sample comprises contacting a biological sample from a subject with CXCL10 binding protein (as described herein) that specifically binds to the CXCL10 polypeptide or protein for a time and under conditions sufficient for a complex between the binding protein and the polypeptide or protein to form and then detecting the complex. For example, in any method described herein the level of active CXCL10 is measured and the level of total CXCL10 is measured and the ratio of active CXCL10 to total CXCL10 determined.

Enzyme Linked Immunosorbent Assay (ELISA) and Fluorescence Linked Immunosorbent Assay (FLISA)

Standard solid-phase ELISA or FLISA formats are particularly useful in determining the concentration of a protein from a variety of samples. In one form such an assay involves immobilizing a biological sample onto a solid matrix, such as, for example a polystyrene or polycarbonate microwell or dipstick, a membrane, or a glass support (e.g. a glass slide).

An antibody that specifically binds to a marker within a CXCL10 polypeptide is brought into direct contact with the immobilized biological sample, and forms a direct bond with any of its target protein present in said sample. This antibody is generally labeled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a second labeled antibody can be used that binds to the first antibody. Following washing to remove any unbound antibody the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label.

Such ELISA or FLISA based systems are suitable for quantification of the amount of a protein in a sample, by calibrating the detection system against known amounts of a protein standard to which the antibody binds, such as for example, an isolated and/or recombinant CXCL10 polypeptide or immunogenic fragment thereof or epitope thereof.

In another example, an ELISA consists of immobilizing an antibody or ligand that specifically binds a marker of a disease or disorder within a CXCL10 polypeptide on a solid matrix, such as, for example, a membrane, a polystyrene or polycarbonate microwell, a polystyrene or polycarbonate microwell dipstick or a glass support. A sample is then brought into physical relation with said antibody, and said marker within the sample is bound or 'captured'. The bound protein is then detected using a labeled antibody. Alternatively, a third labeled antibody can be used that binds the second (detecting) antibody.

In one example, the immobilized antibody is a polyclonal antibody.

It will be apparent to the skilled person that the assay formats described herein are amenable to high throughput formats, such as, for example automation of screening processes or a microarray format as described in Mendoza et al., 1999. Furthermore, variations of the above-described assay will be apparent to those skilled in the art, such as, for example, a competitive ELISA.

In one example, the assay format is a microfluidics device, for example, a microfluidic chip or a droplet-based microfluidics device. Microfluidic chips (e.g., a microelectromechanical systems (MEMS) device), typically range in size from a few square millimeters to a few square centimeters. These microfluidic chips are designed to handle or manipulate small fluid volumes in order to perform biological or medical processing or testing. The fluids may be moved, mixed, or processed in a single microfluidic chip.

In another example, the assay format is a dipstick, for example, a polycarbonate dipstick.

SIMOA Assay

Another assay that can be used in the present invention is a single-molecule array (Simoa) assay, which is described in detail in Kuhle et al. (2016) and Gisslen et al. (2016).

Western Blotting

In another example, western blotting is used to determine the level of a marker within a CXCL10 polypeptide in a sample. In such an assay protein from a sample is separated using sodium dodecyl sulphate polyacrylamide gel electrophoresis (SDS-PAGE) using techniques known in the art and described in, for example, Scopes, 1994. Separated proteins are then transferred to a solid support, such as, for example, a membrane (e.g., a PVDF membrane), using methods known in the art, for example, electrotransfer. This membrane is then blocked and probed with a labeled antibody or ligand that specifically binds to a marker within a CXCL10 polypeptide. Alternatively, a labeled secondary, or even tertiary, antibody or ligand is used to detect the binding of a specific primary antibody. The level of label is then determined using an assay appropriate for the label used.

An appropriate assay will be apparent to the skilled artisan and include, for example, densitometry. In one example, the intensity of a protein band or spot is normalized against the total amount of protein loaded on a SDS-PAGE gel using methods known in the art. Alternatively, the level of the marker detected is normalized against the level of a control/reference protein. Such control proteins are known in the art, and include, for example, actin, glyceraldehyde 3-phosphate dehydrogenase (GAPDH), β2 microglobulin, hydroxy-methylbilane synthase, hypoxanthine phosphoribosyl-transferase 1 (HPRT), ribosomal protein L13c, succinate dehydrogenase complex subunit A and TATA box binding protein (TBP).

Radioimmunoassay

Alternatively, the level of CXCL10 is detected using a radioimmunoassay (RIA). The basic principle of the assay is the use of a radiolabeled antibody or antigen to detect antibody-antigen interactions. An antibody or ligand that specifically binds to the marker within a CXCL10 polypeptide is bound to a solid support and a sample brought into direct contact with said antibody. To detect the level of bound antigen, an isolated and/or recombinant form of the antigen is radiolabeled and brought into contact with the same antibody. Following washing, the level of bound radioactivity is detected. As any antigen in the biological sample inhibits binding of the radiolabeled antigen the level of radioactivity detected is inversely proportional to the level of antigen in the sample. Such an assay may be quantitated by using a standard curve using increasing known concentrations of the isolated antigen.

As will be apparent to the skilled person, such an assay may be modified to use any reporter molecule, such as, for example, an enzyme or a fluorescent molecule, in place of a radioactive label.

Biosensor or Optical Immunosensor System

Alternatively, the level of a CXCL10 in a sample is determined using a biosensor or optical immunosensor system. In general, an optical biosensor is a device that uses optical principles to quantitatively convert the binding of a ligand or antibody to a target polypeptide into electrical signals. These systems can be grouped into four major categories: reflection techniques; surface plasmon resonance; fibre optic techniques and integrated optic devices. Reflection techniques include ellipsometry, multiple integral reflection spectroscopy, and fluorescent capillary fill devices. Fibre-optic techniques include evanescent field fluorescence, optical fibre capillary tube, and fibre optic fluorescence sensors. Integrated optic devices include planer evanescent field fluorescence, input grading coupler immunosensor, Mach-Zehnder interferometer, Hartman interferometer and difference interfermoter sensors. These examples of optical immunosensors are described in general by Robins, 1991. More specific description of these devices are found for example in U.S. Pat. Nos. 4,810,658; 4,978,503; 5,186,897; and Brady et al., 1987.

Biological Samples

As will be apparent to the skilled person, the type and size of the biological sample will depend upon the detection means used. For example, protein-based assays require sufficient cells to provide sufficient protein for an antigen based assay.

As used herein, the term "sample" or "biological sample" refers to any type of suitable material obtained from the subject. The term encompasses a clinical sample (e.g., cervical, or cervicovaginal, swab), biological fluid (e.g., cervical fluid, vaginal fluid, plasma, ascites), tissue samples, live cells and also includes cells in culture, cell supernatants, cell lysates derived therefrom. The sample can be used as obtained directly from the source or following at least one-step of (partial) purification. It will be apparent to the skilled person that the sample can be prepared in any medium which does not interfere with the method of the disclosure. Typically, the sample comprises cells or tissues and/or is an aqueous solution or biological fluid comprising cells or tissues. The skilled person will be aware of selection and pre-treatment methods. Pre-treatment may involve, for example, diluting viscous fluids. Treatment of a sample may involve filtration, distillation, separation, concentration.

In one example, the biological sample has been derived previously from the subject. Accordingly, in one example, a method as described herein according to any embodiment additionally comprises providing the biological sample.

In one example, biological samples may be collected from a subject at more than one time points to e.g. monitor progression of a malignant condition, to monitor for recurrence, and/or to assess the efficacy of a treatment protocol. In one example, the biological sample may be collected from a subject before, during and/or after treatment of a subject for a malignant condition. Samples may be collected, weekly, fortnightly, monthly, every two months, every three months, every four months, every five months or every six months to monitor progression of a malignant condition or assess the efficacy of a treatment regimen.

In one example, a method as described herein according to any embodiment is performed using an extract from a sample, such as, for example, protein.

Reference Samples

As will be apparent from the preceding description, some assays of the present disclosure may utilize a suitable reference sample or control for quantification.

Suitable reference samples for use in the methods of the present disclosure will be apparent to the skilled person and/or described herein. For example, the reference may be an internal reference (i.e., from the same subject), from a normal individual or an established data set (e.g., matched by age, sample type and/or stage of cycle).

In one example, the reference is an internal reference or sample. For example, the reference is an autologous reference. In one example, the internal reference is obtained from the subject at the same time as the sample under analysis. In another example, the internal reference is obtained from the subject at an earlier time point as the sample under analysis.

As used herein, the term "normal individual" shall be taken to mean that the subject is selected on the basis that they do not have a malignant and/or a benign condition, or that they are not suspected of having such condition. For example, the normal individual is a healthy individual.

In one example, the reference is an established data set. Established data sets suitable for use in the present disclosure will be apparent to the skilled person and include, for example:

A data set from a normal subject or a population of normal subjects matched by age and sample type;

A data set from another subject or a population of subjects matched by age, sample type and/or disease/condition;

A data set comprising cells in vitro, wherein the cells have been treated to induce CXCL10 expression; and A data set comprising endometrial epithelial cells in vitro, wherein the cells have been treated to inhibit CXCL10 expression.

In one example, a reference is not included in an assay. Instead, a suitable reference is derived from an established data set previously generated. Data derived from processing, analyzing and/or assaying a test sample is then compared to data obtained for the sample.

Detecting and/or Diagnosing a Malignant Condition

As disclosed herein, the inventors of the present disclosure have demonstrated a role of CXCL10 in detecting and/or diagnosing a malignant condition. It will be apparent to the skilled person that the methods disclosed herein will be useful in distinguishing a malignant condition from a benign condition in a subject. For example, the methods of the present disclosure are useful as a screening test for the diagnosis of a malignant condition in a subject.

Accordingly, the present disclosure provides, for example, a method of detecting and/or diagnosing a malignant condition in a subject, the method comprising:
(i) determining a level of active CXCL10 in the subject and a level of total CXCL10 in the subject; and
(ii) determining a CXCL10 ratio of active CXCL10 to total CXCL10 in the subject.

As used herein, the term "detect", "detecting", "diagnosis" or "diagnosing" refers to the identification of a malignant condition in a subject.

As used herein, the term "malignant condition" refers to a condition or disease that grows in an uncontrolled manner, invades normal tissues, and often metastasizes and grows at sites distant from the tissue of origin. In one example, a malignant disease or condition is cancer or is related to cancer. The skilled person will understand that cancers can arise from almost any tissue in the body and as used herein the term encompasses all forms of the disease, including e.g., carcinomas, sarcomas, lymphomas, and leukemias (i.e., solid and non-solid forms of cancer).

In one example, the present disclosure provides a method of distinguishing a malignant condition from a benign condition.

As used herein, the term "benign condition" refers to a mass of cells that lacks the ability to invade neighbouring tissue.

In one example, the present disclosure provides a method of distinguishing pre-cancerous lesions from a benign condition.

As used herein, the term "pre-cancerous lesion" refers to a mass of cells that have grown abnormally, causing their size, shape or appearance to look different than normal cells, however they are not yet cancerous or malignant. In one example, the pre-cancerous lesion are p53 pre-cancerous lesions. As used herein, the term p53 pre-cancerous lesions refers to cells that have p53 gene mutations.

In one example, the subject suffers from a malignant condition (i.e., cancer). For example, the cancer is a solid tumor, such as a sarcoma or carcinoma. For example, the carcinoma is a carcinoma of the prostate, ovary, breast, lung, liver, kidney, colon, pancreas or stomach. For example, the subject suffers from ovarian cancer. In one example, the cancer is a non-solid tumor, for example leukemia or lymphoma. In one example, the subject suffers from a stage 0 cancer. For example, the carcinoma is in situ. In another example, the subject suffers from a stage I, II or III cancer. For example, the carcinoma has spread beyond the organ of origin to nearby lymph nodes and/or tissues or organs adjacent to the location of the primary tumor. In one example, the subject suffers from a stage IV cancer. For example, the cancer has spread to distant tissues and/or organs.

In one example, the subject has not received treatment for the malignant condition. For example, the subject is treatment naive.

In one example, the subject is receiving treatment for the malignant condition. In one example, the subject has received treatment for the malignant condition. Suitable therapies for the treatment of the malignant condition will be apparent to the skilled person and/or described herein. For example, the treatment comprises surgery, chemotherapy, radiation therapy, targeted drug therapy, immunotherapy or a combination thereof.

Ovarian Cancer

In one example of any method described herein, the method comprises detecting and/or diagnosing ovarian cancer in a subject. For example, the subject suffers from ovarian cancer.

As used herein, the term "ovarian cancer" refers to any cancerous growth that begins in the ovary.

In one example, the method comprises a method of differentiating ovarian cancer in a subject from a benign condition.

It will be apparent to the skilled person that the methods described herein are applicable for detecting and/or diagnosing all subtypes of ovarian cancer including, for example, epithelial, endometrioid tumours, germ-cell tumours, clear cell and mucinous adenocarcinomas.

In one example, the present disclosure provides a method for detecting and/or diagnosing epithelial ovarian cancer in a subject.

The skilled person will understand that ovarian cancer is staged using the International Federation of Gynaecology and Obstetrics (FIGO) staging system, as described below in Table 2.

In one example of any method described herein, the present disclosure provides a method for detecting and/or diagnosing ovarian cancer in a subject irrespective of stage of the cancer.

In one example of any method described herein, the present disclosure provides a method for detecting and/or diagnosing stage I ovarian cancer in a subject.

The skilled person will also understand that ovarian cancer is classified based on the grade of the cancer. For example, grade 1 tumours have well differentiated cells; grade 2 tumours are moderately well-differentiated; and grade 3 tumours are poorly differentiated.

In one example of any method described herein, the present disclosure provides a method for detecting and/or diagnosing ovarian cancer in a subject irrespective of grade of the cancer.

In another example, the ovarian cancer is serous, mucinous, endometrioid, clear cell, GCT or a mixture thereof, ovarian cancer. In an example, the ovarian cancer is serous.

In one example, the subject is at risk of ovarian cancer.

As used herein, a subject "at risk" of ovarian cancer may or may not have detectable ovarian cancer or symptoms of ovarian cancer. "At risk" denotes that a subject has one or more risk factors, which are measurable parameters that correlate with development of the disease or condition, as known in the art and/or described herein. For example, the subject has a p53 gene mutation.

TABLE 2

| \multicolumn{3}{c}{FIGO stages of ovarian cancer} | | |
|---|---|---|---|---|
| Stage | | | | Description |
| I | | | | Cancer is completely limited to the ovary |
| | IA | | | involves one ovary, capsule intact, no tumor on ovarian surface, negative washings |
| | IB | | | involves both ovaries; capsule intact; no tumor on ovarian surface; negative washings |
| | IC | | | tumor involves one or both ovaries |
| | IC1 | | | surgical spill |
| | IC2 | | | capsule has ruptured or tumor on ovarian surface |
| | IC3 | | | positive ascites or washings |
| II | | | | pelvic extension of the tumor (must be confined to the pelvis) or primary peritoneal tumor, involves one or both ovaries |
| | IIA | | | tumor found on uterus or fallopian tubes |
| | IIB | | | tumor elsewhere in the pelvis |
| III | | | | cancer found outside the pelvis or in the retroperitoneal lymph nodes, involves one or both ovaries |
| | IIIA | | | metastasis in retroperitoneal lymph nodes or microscopic extrapelvic metastasis |
| | | IIIA1 | | metastasis in retroperitoneal lymph nodes |
| | | | IIIA1 (i) | the metastasis is less than 10 mm in diameter |
| | | | IIIA1 (ii) | the metastasis is greater than 10 mm in diameter |
| | | IIIA2 | | microscopic metastasis in the peritoneum, regardless of retroperitoneal lymph node status |
| | IIIB | | | metastasis in the peritoneum less than or equal to 2 cm in diameter, regardless of retroperitoneal lymph node status; or metastasis to liver or spleen capsule |
| | IIIC | | | metastasis in the peritoneum greater than 2 cm in diameter, regardless of retroperitoneal lymph node status; or metastasis to liver or spleen capsule |
| IV | | | | distant metastasis (i.e. outside of the peritoneum) |
| | IVA | | | pleural effusion containing cancer cells |
| | IVB | | | metastasis to distant organs (including the parenchyma of the spleen or liver), or metastasis to the inguinal and extra-abdominal lymph nodes |

Risk factors include, for example:

A family history of ovarian and/or breast cancer;

Reproductive history, i.e., having children after the age of 35 or never having children are associated with a higher risk;

History of breast cancer;

Hormonal therapy, e.g., hormone replacement therapy (HRT) after menopause is associated with an increased risk; and Obesity, e.g., a body mass index of greater than 30.

A subject is at risk if she has a higher risk of developing ovarian cancer than a control population. The control population may include one or more subjects selected at random from the general population (e.g., matched by age, gender, race and/or ethnicity) who have not suffered from or have a family history of ovarian cancer. A subject can be considered at risk if a "risk factor" associated with ovarian cancer is found to be associated with that subject. A risk factor can include any activity, trait, event or property associated with a given disorder, for example, through statistical or epidemiological studies on a population of subjects. A subject can thus be classified as being at risk even if studies identifying the underlying risk factors did not include the subject specifically.

In one example, the method of the present disclosure is performed before or after the onset of symptoms of ovarian cancer. Symptoms of ovarian cancer will be apparent to the skilled person and include, for example:

Abdominal enlargement or swelling;
Abdominal fullness and pain;
Pain in lower abdomen;
Feeling full after eating very little;
Tiredness;
Changes in bowel or bladder habits;
Clothes not fitting well;
Swelling of legs;
Shortness of breath;
Bleeding from vagina;
Abnormal menstrual cycles;
Weight loss or gain; and
Unexplained back pain.

The present inventors have also found that the methods of the present disclosure may be combined with the detection of other biological markers.

In one example, the methods of the present disclosure further comprise determining the level of dipeptidyl peptidase-4 (DPP4) and/or cancer antigen 125 (CA-125) in the subject. In one example, the method further comprises determining the level of DPP4. In another example, the method further comprises determining the level of CA-125. In a further example, the method further comprises determining the level of DPP4 and CA-125.

Methods of measuring DPP4 and/or CA-125 are known in the art (see, for example, U.S. Pat. No. 5,356,817, Saho et al., 2019; Scholler et al., 2007 and Vuento et al., 1997) and/or are described herein.

In one example, the methods of the present disclosure further comprise determining the level of one or more or all of granulocyte-macrophage colony-stimulating factor (GM-CSF), interleukin 6 (IL-6), tumor necrosis factor receptor II (TNF-RII), human epididymis protein 4 (HE4) and interleukin 8 (IL-8).

In one example, the methods further comprise determining the level of GM-CSF.

In one example, the methods further comprise determining the level of IL-6.

In one example, the methods further comprise determining the level of TNF-RII.

In one example, the methods further comprise determining the level of HE4.

In one example, the methods further comprise determining the level of IL-8.

In one example, the methods further comprise determining the level of GM-CSF, IL-6, TNF-RII, HE4 and IL-8.

In one example of any method described herein, the method further comprises determining the level of DPP4, GM-CSF, IL-6, TNF-RII, HE4 and IL-8.

In one example of any method described herein, the method further comprises determining the level of CA-125, GM-CSF, IL-6, TNF-RII, HE4 and IL-8.

In one example of any method described herein, the method further comprises determining the level of DPP4, CA-125, GM-CSF, IL-6, TNF-RII, HE4 and IL-8.

Methods of Treating a Malignant Condition

In one example, the present invention provides a method of treating a malignant condition in a subject, the method comprising performing the method as described herein and treating the subject for the malignant condition.

As used herein, the terms "treating", "treat" or "treatment" includes surgically removing all or part of the cancer or administering a therapeutically effective amount of a compound/molecule/radiation sufficient to reduce or eliminate at least one symptom of the malignant condition. For example, an "effective amount" for therapeutic uses is the amount of the compound required to provide a clinically significant decrease in disease symptoms without undue adverse side effects. An appropriate "effective amount" in any individual case may be determined using techniques, such as a dose escalation study. An "effective amount" of a compound is an amount effective to achieve a desired pharmacologic effect or therapeutic improvement without undue adverse side effects. It is understood that "an effective amount" or "a therapeutically effective amount" can vary from subject to subject, due to variation in metabolism of the compound of any of age, weight, general condition of the subject, the condition being treated, the severity of the condition being treated, and the judgment of the prescribing physician.

In one example, treatment comprises surgery, chemotherapy, radiation therapy, targeted drug therapy or a combination thereof.

In one example, the treatment comprises surgery. For example, the surgery is debulking surgery.

In another example, the treatment comprises chemotherapy. Exemplary chemotherapy agents include, for example, caboplatin, cytarabine, chlorambucil, cisplatin, cyclophosphamide, danorubicin, docetaxal, doxorubicin, erlotinib, etoposide, fluorouracil, fludarabine, idarubicin, irinotecan, liposomal doxorubicin, methotrexate, mitoxantrone, paclitaxel, topotecan, vincristine and vinblastine.

In one example, the treatment comprises radiation therapy. For example, the radiation therapy is selected from the group consisting of external beam radiation therapy (EBRT), three-dimensional conformal radiation therapy (3D-CRT), intensity modulated radiation therapy (IMRT), volumetric modulated arc therapy (VMAT), conformal proton beam radiation therapy, stereotactic radiosurgery (SRS)/stereotactic radiotherapy (SRT), image-guided radiation therapy (IGRT), brachytherapy (internal radiation therapy) and whole brain and spinal cord radiation therapy (craniospinal radiation).

In one example, the treatment comprises targeted drug therapy. For example, the targeted drug therapy is a therapeutic antibody. Exemplary therapeutic antibodies are known to the skilled person and include, but are not limited to, Abagovomab; Abciximab; Abituzumab; Abrilumab; Actoxumab; Adalimumab; Adecatumumab; Aducanumab; Afelimomab; Afutuzumab; Alacizumab pegol; Alemtuzumab; Alirocumab; Altumomab pentetate; Amatuximab; Anatumomab mafenatox; Anetumab ravtansine; Anifrolumab; Anrukinzumab; Apolizumab; Arcitumomab; Ascrinvacumab; Aselizumab; Atezolizumab; Atinumab; Atlizumab (tocilizumab); Atorolimumab; Bapineuzumab; Basiliximab; Bavituximab; Bectumomab; Begelomab; Belimumab; Benralizumab; Bertilimumab; Besilesomab; Bevacizumab; Bezlotoxumab; Biciromab; Bimagrumab; Bimekizumab; Bivatuzumab mertansine; Blinatumomab; Blosozumab; Bococizumab; Brentuxim abvedotin; Briakinumab; Brodalumab; Brolucizumab; Brontictuzumab; Canakinumab; Cantuzumab mertansine; Cantuzumab ravtansine; Caplacizumab; Capromab pendetide; Carlumab;

Catumaxomab; cBR96-doxorubicin immunoconjugate; Cedelizumab; Certolizumab pegol; Cetuximab; Citatuzumab bogatox; Cixutumumab; Clazakizumab; Clenoliximab; Clivatuzumab tetraxetan; Codrituzumab; Coltuximab ravtansine; Conatumumab; Concizumab; Crenezumab; Dacetuzumab; Daclizumab; Dalotuzumab; Dapirolizumab pegol; Daratumumab; Dectrekumab; Demcizumab; Denintuzumab mafodotin; Denosumab; Derlotuximab biotin; Detumomab; Dinutuximab; Diridavumab; Dorlimomab aritox; Drozitumab; Duligotumab; Dupilumab; Durvalumab; Dusigitumab; Ecromeximab; Eculizumab; Edobacomab; Edrecolomab; Efalizumab; Efungumab; Eldelumab; Elgemtumab; Elotuzumab; Elsilimomab; Emactuzumab; Emibetuzumab; Enavatuzumab; Enfortumab vedotin; Enlimomab pegol; Enoblituzumab; Enokizumab; Enoticumab; Ensituximab; Epitumomab cituxetan; Epratuzumab; Erlizumab; Ertumaxomab; Etanercept; Etaracizumab; Etrolizumab; Evinacumab; Evolocumab; Exbivirumab; Fanolesomab; Faralimomab; Farletuzumab; Fasinumab; Felvizumab; Fezakinumab; Ficlatuzumab; Figitumumab; Firivumab; Flanvotumab; Fletikumab; Fontolizumab; Foralumab; Foravirumab; Fresolimumab; Fulranumab; Futuximab; Galiximab; Ganitumab; Gantenerumab; Gavilimomab; Gemtuzumab ozogamicin; Gevokizumab; Girentuximab; Glembatumumab vedotin; Golimumab; Gomiliximab; Guselkumab; Ibalizumab; Ibritumomab tiuxetan; Ierucumab; Idarucizumab; Igovomab; Imalumab; Imciromab; Imgatuzumab; Inclacumab; Indatuximab ravtansine; Indusatumab vedotin; Infliximab; Inolimomab; Inotuzumab ozogamicin; Intetumumab; Ipilimumab; Iratumumab; Isatuximab; Itolizumab; Ixekizumab; Keliximab; Labetuzumab; Lambrolizumab; Lampalizumab; Lebrikizumab; Lemalesomab; Lenzilumab; Lerdelimumab; Lexatumumab; Libivirumab; Lifastuzumab vedotin; Ligelizumab; Lilotomab satetraxetan; Lintuzumab; Lirilumab; Lodelcizumab; Lokivetmab; Lorvotuzumab mertansine; Lucatumumab; Lulizumab pegol; Lumiliximab; Lumretuzumab; Mapatumumab; Margetuximab; Maslimomab; Matuzumab; Mavrilimumab; Mepolizumab; Metelimumab; Milatuzumab; Minretumomab; Mirvetuximab soravtansine; Mitumomab; Mogamulizumab; Morolimumab; Motavizumab; Moxetumomab pasudotox; Muromonab-CD3; Nacolomab tafenatox; Namilumab; Naptumomab estafenatox; Narnatumab; Natalizumab; Nebacumab; Necitumumab; Nemolizumab; Nerelimomab; Nesvacumab; Nimotuzumab; Nivolumab; Nofetumomab merpentan; Obiltoxaximab; Obinutuzumab; Ocaratuzumab; Ocrelizumab; Odulimomab; Ofatumumab; Olaratumab; Olokizumab; Omalizumab; Onartuzumab; Ontuxizumab; Opicinumab; Oportuzumab monatox; Oregovomab; Orticumab; Otelixizumab; Otlertuzumab; Oxelumab; Ozanezumab; Ozoralizumab; Pagibaximab; Palivizumab; Panitumumab; Pankomab; Panobacumab; Parsatuzumab; Pascolizumab; Pasotuxizumab; Pateclizumab; Patritumab; Pembrolizumab; Pemtumomab; Perakizumab; Pertuzumab; Pexelizumab; Pidilizumab; Pinatuzumab vedotin; Pintumomab; Placulumab; Polatuzumab vedotin; Ponezumab; Priliximab; Pritoxaximab; Pritumumab; Quilizumab; Racotumomab; Radretumab; Rafivirumab; Ralpancizumab; Ramucirumab; Ranibizumab; Raxibacumab; Refanezumab; Regavirumab; Reslizumab; Rilotumumab; Rinucumab; Rituximab; Robatumumab; Roledumab; Romosozumab; Rontalizumab; Rovelizumab; Ruplizumab; Sacituzumab govitecan; Samalizumab; Sarilumab; Satumomab pendetide; Secukinumab; Seribantumab; Setoxaximab; Sevirumab; Sibrotuzumab; Sifalimumab; Siltuximab; Simtuzumab; Siplizumab; Sirukumab; Sofituzumab vedotin; Solanezumab; Solitomab; Sonepcizumab; Sontuzumab; Stamulumab; Sulesomab; Suvizumab; Tabalumab; Tacatuzumab tetraxetan; Tadocizumab; Talizumab; Tanezumab; Taplitumomab paptox; Tarextumab; Tefibazumab; Telimomab aritox; Tenatumomab; Teneliximab; Teplizumab; Teprotumumab; Tesidolumab; Tetulomab; Ticilimumab; Tigatuzumab; Tildrakizumab; Tocilizumab; Toralizumab; Tosatoxumab; Tositumomab; Tovetumab; Tralokinumab; Trastuzumab; Tregalizumab; Tremelimumab; Trevogrumab; Tucotuzumab celmoleukin; Tuvirumab; Ublituximab; Ulocuplumab; Urelumab; Urtoxazumab; Ustekinumab; Vandortuzumab vedotin; Vanticumab; Vanucizumab; Vapaliximab; Varlilumab; Vatelizumab; Vedolizumab; Veltuzumab; Vepalimomab; Vesencumab; Visilizumab; Volociximab; Vorsetuzumab mafodotin; Votumumab; Zalutumumab; Zanolimumab; Zatuximab; Ziralimumab; Zolimomab aritox.

In one example, the treatment comprises immunotherapy. For example, the immunotherapy is selected from the group consisting of checkpoint inhibitors, oncolytic virus therapy, T-cell therapy and cancer vaccines.

In one example, the immunotherapy is a checkpoint inhibitor. Suitable checkpoint inhibitors include, for example, ipilimumab (Yervoy®), nivolumab (Opdivo®), pembrolizumab (Keytruda®), atezolizumab (Tecentriq®), avelumab (Bavencio®), durvalumab (Imfinzi®).

In one example, the immunotherapy is an oncolytic virus therapy. For example, the oncolytic virus therapy is talimogene laherparepvec (Imlygic®), or T-VEC.

In one example, the immunotherapy is a T-cell therapy. For example, the T-cell therapy is CAR T-cell therapy.

In one example, the immunotherapy is a cancer vaccine.

Monitoring Tumour Burden, Progression, Recurrence and Regression

It will be apparent to the skilled person that the present disclosure also provides a method of monitoring tumour burden, monitoring progression, monitoring recurrence and/or determining tumour regression in a subject suffering from a malignant condition, the method comprising (i) determining a level of active CXCL10 in the subject and a level of total CXCL10 in the subject; and (ii) determining a CXCL10 ratio of active CXCL10 to total CXCL10 in the subject.

As used herein, the term "monitoring" can include, determination of prognosis, response to drug therapy, assessment of ongoing drug therapy, prediction of outcomes, determining response to therapy (including diagnosis of a complication), following progression of tumour volume, or selecting patients most likely to benefit from a therapy.

As used herein, the term "tumour burden" refers to the volume of tumour cells and does not include other changes such as inflammation, necrosis or edema.

As used herein, the term "progression" refers to continued growth and invasiveness of the tumour.

As used herein, the term "regression" refers to a decrease in the size or volume of the tumour.

As used herein, the term "recurrence" refers to a malignant condition that has returned or come back after a period of time in which the malignant condition could not be detected.

In one example, the method of monitoring tumour burden, monitoring progression, monitoring recurrence and/or determining tumour regression in a subject suffering from a malignant condition comprises determining a CXCL10 ratio in the subject at one or more time points. For example, the level of expression of the miRNA is determined at 1, or 2, or 3, or 4, or 5, or 6, or 7, or 8, or 9, or 10 time points.

In one example, the CXCL10 ratio is determined in at least one biological sample obtained from the subject prior to treatment, during treatment and/or after treatment. For example, the CXCL10 ratio is determined at one or more time points prior to treatment. In another example, the CXCL10 ratio is determined at one or more time points during treatment. In a further example, the CXCL10 ratio is determined at one or more time points after treatment. In another example, the CXCL10 ratio is determined prior to and during treatment. In a further example, the CXCL10 ratio is determined prior to and after treatment. In another example, the CXCL10 ratio is determined during and after treatment. In a further example, the CXCL10 ratio is determined prior to, during and after treatment.

In one example, the method comprises comparing the CXCL10 ratio in the subject at a first time point to a CXCL10 ratio in the subject at a subsequent time point.

It will be apparent to the skilled person from the disclosure that reference to a first and subsequent time point is not reference to a defined or specific time point and is for the purposes of comparison only. The first, second (and any subsequent) time points may be separated by any period of time during which it is wished to monitor the subject's malignant condition. The monitoring methods of the disclosure may make use of further samples at further time points (for example a third sample at a third time point, in addition to the first and second samples).

As will be apparent to the skilled person, the ability to monitor the CXCL10 ratio of the present disclosure over the course of the disease will assist in monitoring tumour burden and disease progression.

It will be apparent to the skilled person, that methods of monitoring tumour burden and disease progression in a subject will be useful for determining tumour regression and/or recurrence in a subject.

Panels and Kits

The present disclosure provides panels or kits for detecting and/or diagnosing a malignant condition in a subject. The present disclosure also provides panels or kits for monitoring tumour burden, tumour progression and/or tumour regression. The panels or kits of the invention will preferably comprise one or more or both CXCL10 binding proteins described herein. Optionally, the panel or kit comprises instructions for use in a method described herein.

In one example, the panel or kit comprises a reference sample.

In one example, the panel or kit as described herein is for ex vivo analysis. In one example, the kit is suitable for use with whole blood, plasma, cervicovaginal (CVS) swabs and/or serum samples.

In one example, the panel or kit as described herein is suitable for high-throughput screening. The term "high-throughput screening" refers to screening methods that can be used to test or assess more than one sample at a time and that can reduce the time for testing multiple samples. In one example, the methods are suitable for testing or assessing at least 5 samples, at least 10, at least 20, at least 30, at least 50, at least 70, at least 90, at least 150, at least 200, at least 300 samples at a time. Such high-throughput screening methods can analyse more than one sample rapidly e.g. in at least 30 minutes, in at least 1 hour, in at least 2 hours, in at least 3 hours, in at least 4 hours, in at least 5 hours, in at least 6 hours, in at least 7 hours, in at least 8 hours, in at least 9 hours or in at least 10 hours. High-throughput screening may also involve the use of liquid handling devices. In one example, high-throughput analysis may be automated.

The present disclosure includes the following non-limiting examples.

EXAMPLES

Example 1: Materials and Methods

Reagents

Nunc-Immuno Microwell 96 well solid plates were purchased from SigmaAldrich (USA). TMB chromogen solution was from ThermoFisher (USA). Recombinant human CXCL10 protein (used for immunization and assay standards) was from Genscript (Hong Kong) (SEQ ID NO:2). Short peptides comprising either the active or truncated N-terminus of CXCL10 were synthesized by Mimotopes (Australia). Biotin (Type A) fast conjugation kit, anti-IP-10 antibody, streptavidin peroxidase, anti-human IP-10 ELISA kit, human Dipeptidyl peptidase IV ELISA kit, and active peptidyl arginine deiminase (PAD) cocktail were from Abcam (UK). All other reagents were of analytical grade.

Clinical Samples

Clinical samples were accessed from archival samples stored in the Ovarian Cancer Research Foundation Tissue Bank, collected prospectively from women undergoing surgery for suspected gynaecological malignancies during the period 2007-2014. All samples were obtained from anaesthetised, chemo-naive patients who had undergone no prior surgical treatment.

Histological assessment of tumour type, stage and grade, pre-surgical CA125 measurements, age, menopausal status, pre-existing conditions and any prior history of malignancy were obtained from de-identified patient medical records. Measurement of serum CA125 in the samples was performed in the diagnostic pathology laboratory at the Monash Medical Centre, Melbourne, Australia. Ethical approval was obtained from the Southern Health Human Research Ethics Committee (HREC certificates; #06032C, #02031B), with all participants providing prior informed written consent.

Patient samples are divided into two groups according to pathology; benign and malignant.

Median CA125 measurements with interquartile range (IQR) for variability measure for each group.

Both benign and malignant groups involved women with pre- and post-menopausal (i.e. mixed).

The sample types tested in this study were ascites, plasma, cervicovaginal swab (CVS) and are detailed in Table 3.

TABLE 3

Summary of patient samples (ascites, plasma, CVS) used for comparison of active CXCL10 ratios between benign and malignant samples.

| Group | Pathology | Grade | Stage | Median CA125 (IQR) | Menopausal status |
|---|---|---|---|---|---|
| Benign (n = 51) | Adenofibroma (n = 1) Cystadenoma (n = 18) Cystadenofibroma (n = 3) Cyst (n = 2) Cystadenomata (n = 1) Cyst-dermoid (n = 1) Fibroid (n = 1) Fibroma (n = 10) Fibrothecoma (n = 1) Hydrosalpinx (n = 1) Lipoid cell tumour (n = 1) Mature teratoma (n = 2) Torted (n = 1) Xanthogranulomatous | n/a | n/a | 52 (23-154) | Mixed |

TABLE 3-continued

Summary of patient samples (ascites, plasma, CVS) used for comparison of active CXCL10 ratios between benign and malignant samples.

| Group | Pathology | Grade | Stage | Median CA125 (IQR) | Meno-pausal status |
|---|---|---|---|---|---|
| | (n = 1) Unknown (n = 7) | | | | |
| Malignant (n = 226) | Adenocarcinoma (n = 32) Cystadenocarcinoma (n = 5) Endometrium (n = 2) Teratoma (n= 1) MMMT carcinosarcoma (n = 2) Papillary adenocarcinoma (n = 64) Peritoneum (n = 1) Tubal (n = 1) Pancreaticobiliary (n = 1) Unknown (n = 117) | 1, 2, 3 | 1, 3, 4 | 641 (149-1591) | Mixed |

Generation of Monoclonal Antibodies Against Human CXCL10

Monoclonal antibodies were generated in the Monash Antibody Technologies Facility against full-length, recombinant CXCL10 protein (SEQ ID NO:2). Short peptides comprising the intact (NH2-VPLSRTVRCTCISISNQPVN-PRSLE-COOH) (SEQ ID NO: 25) or truncated (NH2-LSRTVRCTCISISNQPVNPRSLE-COOH) (SEQ ID NO: 26) N-terminus of human CXCL10, were used for screening.

Mice were inoculated intraperitoneally with 16 ug of adjuvanted (Sigma adjuvant system®; S6322) full-length CXCL10, co-injected with methylated CpG, in three fortnightly doses. Serum titres were tested by ELISA and compared against naive sera collected prior to immunization. Mice displaying the highest titres were selected for hybridoma generation. Splenocytes were extracted and fused to SP2/0-Ag14 myeloma cells using polyethylene glycol. The resultant hybridoma cells were grown in azaserine-hypoxantine containing medium in 96 well tissue culture plates for 13 days. The supernatants for each individual hybridoma were screened by microarray for reactivity against both full-length protein and each peptide antigen, with positive clones re-screened by ELISA.

The highest responding clones demonstrating appropriate antigen specificity were expanded and sub-cloned, to ensure the derivation of monoclonal hybridoma lines. Monoclonal antibodies were purified from supernatants using Protein G Sepharose, and Ig isotype was determined using commercially available assay kits. The final monoclonal hybridomas lines of interest were grown to 80% confluence, snap frozen with 10% DMSO as cryoprotectant and stored in liquid $N_2$.

Surface Plasmon Resonance Imaging

Two monoclonal antibodies; namely mAb-RA2 specific for full length, N-terminally intact CXCL10, and mAb-RG2 specific for both full length and truncated CXCL10, were analysed by Surface Plasmon Resonance (SPR) for binding affinity against both forms of CXCL10. Experiments were performed using a ProteOn XPR36 SPRi biosensor (Bio-Rad), equipped with a GLC chip. The chip was conditioned with 0.5% SDS, 50 mM NaOH and 100 mM HCl, and then the lanes were activated using equal parts 1-Ethyl-3-(3-dimethylaminopropyl) carbodiimide (EDAC) and N-Hydroxysuccinimide (NHS). The antibodies were immobilised in separate lanes at a concentration of 50 g/mL in sodium acetate buffer (pH4.5), then each lane deactivated using ethanolamine. Antigens were applied to each lane, and binding was recorded as RU. All channels were regenerated using 0.85% H3PO3 between applications of antigen. Interspot and control RU were subtracted to give specific binding.

Biotinylation of RA2 and RG2 Monoclonal Antibodies mAb-RA2 and mAb-RG2 antibodies were biotinylated using a biotinylation kit (Abcam; ab201795) to use them as detection antibodies in the active ratio test (ART) of the invention, in which streptavidin-peroxidase was used as the detection reagent. Biotinylation of the two monoclonal antibodies was performed according to the manufacturer's instruction; 10 μL of biotin modifier reagent was added to 100 μL of each purified monoclonal antibody (2 mg mL-1; PBS, pH 7.4), followed by gentle mixing. The mixture was added to lyophilised biotin directly and mixed gently. They were incubated for 15 minutes at room temperature. After the incubation, 10 μL of biotin quencher reagent was added to complete biotinylation of the two antibodies.

Quantitation of Active and Total CXCL10

Ascites fluid and plasma samples were pre-cleared by centrifugation (18,400×g, 20 minutes at 4° C.) and the cleared supernatants transferred to a fresh tube. Samples were diluted (1: 5) with assay buffer (0.1% BSA/0.05% Tween 20/PBS, pH 7.4) and maintained on ice prior to assay. CVS samples were vortexed for 30 seconds, sonicated for 15 minutes in an ice bath and then vortexed for a further 30 seconds. Supernatants were centrifuged as above, and maintained on ice until assay.

For assessment by ART, anti-human IP-10 polyclonal antibody (Abcam; #ab9807) prepared in the coating buffer (15 mM $NaCO_3$ and 35 mM $NaHCO_3$, pH 9.6) was immobilised on the 96 well microplate (100 μL per well) at a coating concentration of 0.5 pg mL-1 for 2 hours at room temperature. Plates were washed once with 280 μL of wash solution (0.05% Tween 20/Milli-Q H2O), then incubated with 300 μL blocking solution (5% BSA/0.05% Tween 20/PBS, pH 7.4) for 2 hours at room temperature. Plates were washed four times in wash solution, and then standards (recombinant CXCL10 (SEQ ID NO:2), 48.8 pg mL-1 to 200,000 pg mL-1) or samples were added to respective wells (100 μL per well) in quadruplicate. Following 2 hours incubation, each well was washed four time in wash solution. Biotinylated detection antibodies mAb-RA2 and mAb-RG2 (1 pg mL-1 in assay buffer) were added (100 μL per well) as appropriate and incubated for 1 hour at room temperature. Following incubation plates were washed five times with wash buffer, then incubated with diluted (1: 1000) streptavidin peroxidase (1 pg/mL/well) for 45 minutes at room temperature. Plates were washed a further four times in wash solution, then 100 μL of TMB chromogen solution added to each well and incubated for 20 minutes in the dark at room temperature. The reaction was stopped by addition of stop solution (1M hydrochloric acid, 50 μL per well). Absorbance was measured at a wavelength of 450 nm, using a Cytation 3 multimode plate reader (Biotek, La Jolla CA) equipped with Gen5 v3.08 analysis software. Comparison between ART and standard ELISA (detecting total CXCL10 only) was performed using a colorimetric anti-human IP-10 ELISA kit (Abcam #ab100579) according to the manufacturer's instructions.

Quantitation of DPP4 and Analysis of DPP4 Specific Activity

DPP4 abundance was assessed in matched ascites samples (diluted 1: 4) using a commercial anti-human DPP4 ELISA (Abcam #ab222872), according to the manufacturer's instructions. Detection and concentration analyses were performed using the Cytation multimode plate reader (as above). Nonlinear regression curve in asymmetric sigmoidal against DPP4 concentration in log was constructed to quantitate soluble DPP4 in the samples.

DPP4 specific activity (pmol/min/ng DPP4) was measured using Gly-Pro-7-amido-4-methylcoumarin hydrobromide (H-Gly-Pro-AMC) as DPP4 substrate as previously described (Sinnathurai et al., 2018). Citrullination of full length CXCL10 was performed by incubating with human protein-arginine deiminase 2 (PAD2) at 37° C. for up to 1 hour. Aliquots were taken every 15 minutes during the incubation for time course measurements. The time course samples were then separated by SDS PAGE and probed with mAb-RA2, mAb-RG2, commercial anti-CXCL10 antibody, and anti-citrulline antibody by Western blotting as previously described (Loos et al., 2008).

dently measure intact or total CXCL10. Specific parameters including limit of detection (LOD), limit of quantitation (LOQ), linearity, inter- and intra-assay precision and dynamic range were assessed (Table 4). Each of mAb-RA2 and mAb-RG2 demonstrated good affinity for full-length CXCL10, with an R-squared of 0.996 and 5 orders of magnitude (OOM) dynamic range (FIG. 1). Limits of detection for mAb-RA2 and mAb-RG2 were 95.9 pg mL-1 and 116.3 pg mL-1, respectively (Table 4). Inter-assay precision was assessed using 10 independently prepared replicates at a single dose; and intra-assay variation was determined between 10 separate assay runs performed on different days. Coefficient of variation (CV) for both intra- and inter-assays was below 10% in each case, demonstrating good reproducibility and assay precision (Table 4).

TABLE 4

Binding affinity for mAb-RA2 and mAB-RG2 by SPR.

| | Binding Affinity (KD) for CXCL10 Proteomics | | | Assay Parameters | | | |
|---|---|---|---|---|---|---|---|
| | Full length | Intact N-term | VP-truncated N-term | Limit of detection (LOD) | Limit of quantification (LOQ) | Intra-assay precision (%) | Inter-assay precision (%) |
| mAb-RA2 | $4.90 \times 10^{-10}$ | $7.36 \times 10^{-10}$ | no binding | 95.9 pg mL$^{-1}$ | 162.2 pg mL$^{-1}$ | 2.8 | 9.9 |
| mAb-RG2 | $3.89 \times 10^{-12}$ | $3.54 \times 10^{-9}$ | $3.00 \times 10^{-9}$ | 116.3 pg mL$^{-1}$ | 272.7 pg mL$^{-1}$ | 4.0 | 8.5 |

Statistical Analyses

Statistical analyses were carried out using GraphPad PRISM (GraphPad Software, La Jolla CA), with all assay data log-transformed to approximate normality. The best-fit line was determined by nonlinear regression curve in asymmetric sigmoidal (5PL) against total CXCL10 concentration in log for mAb-RA2 and mAb-RG2 assays to quantitate active and active or truncated CXCL10, respectively. Concentrations of CXCL10 obtained from the assays are in pg mL-1. Significance was determined using one-way ANOVA and Bonferroni post hoc test, with pairwise comparisons performed using Student's t-test. For those groups with significantly different variance, Welch's correction was applied. Spearman rank test was used for correlation analyses. Results of $P<0.05$ were considered significant.

Example 2: Generation of a Functional Assay Differentiating Active from Total CXCL10

The inventors developed a monoclonal antibody that could differentiate between the N-terminally intact, chemotactically active form of CXCL10 and all other variants. Using full-length CXCL10 protein as the antigen, hybridoma clones were isolated and screened for reactivity against (i) full-length CXCL10 protein; and (ii) short synthetic peptides, representing either the intact or truncated N-terminus of CXCL10. Antibodies secreted by clone mAb-RA2 recognized both full-length and N-terminally intact CXCL10, but not the N-terminally truncated form (Table 4). Antibodies secreted by clone mAb-RG2 reacted with all proteoforms of CXCL10 tested. SPR analysis demonstrated binding affinity in the nM to pM range in each case. The open reading frames encoding the variable regions of both antibodies was sequenced.

Figure 2A:
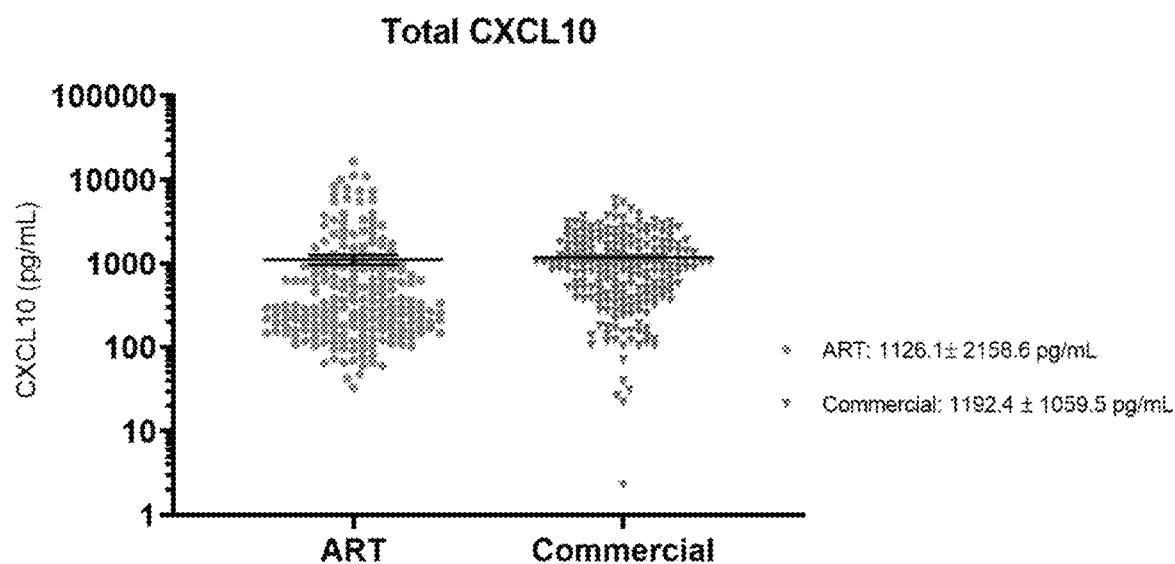
FIG. 2A shows a comparison of quantitated total CXCL10 in malignant ascites fluids from ovarian cancer patients (n=212) between ART and commercial ELISA. No significant difference in quantitated total CXCL10 in the matched ascites fluids was observed between ART and commercial ELISA. Overall averages of total CXCL10 by ART and commercial ELISA were 1126.1±2158.6 pg/mL and 1192.4±1059.5 pg/mL, respectively.
Figure 2B:
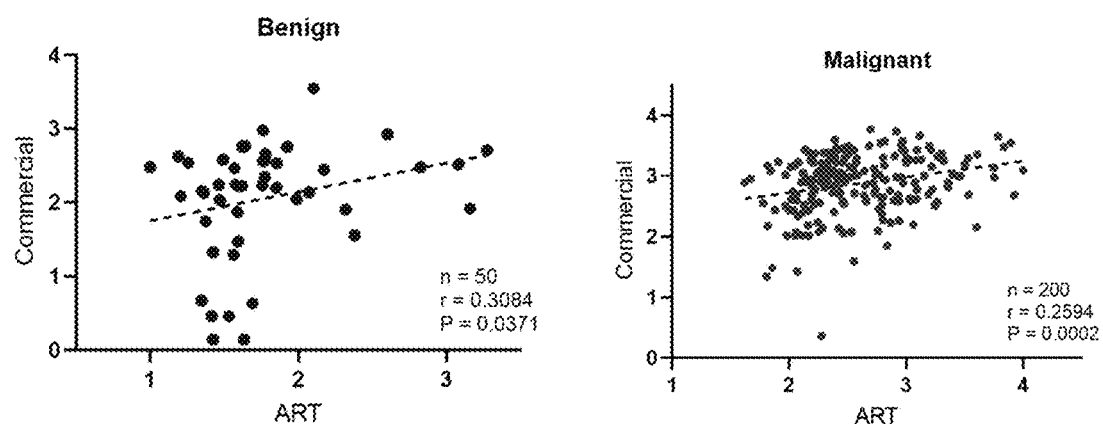
FIG. 2B shows correlations of quantitated total CXCL10 between ART and commercial ELISA; moderately positive correlations between the two tests for both benign and malignant ascites fluid with r values of 0.3084 and 0.2594, respectively. $P<0.05$.

Using biotinylated mAb-RA2 and mAb-RG2 as detection antibodies, sandwich ELISAs were constructed to indepen- The inventors next sought to validate quantitative detection of CXCL10 using ART, compared to a commercially available ELISA kit. CXCL10 is abundant in ascites fluid from ovarian cancer patients, where it is involved in the CXCR3-mediated migration of cancer cells and specific T-cell subsets (Rainczuk et al., 2012; Windmuller et al., 2017). The inventors therefore assessed CXCL10 detection in ascites fluid from ovarian cancer patients (n=212) as a representative, complex biological matrix. Whilst there was considerable deviation in concentration range within the sample group (CVs ranging from 88.4%-225.1%), there was no significant difference in quantitation of total CXCL10 between ART versus commercial ELISA (FIG. 2A). Positive correlations in quantitated total CXCL10 were observed between ART and commercial ELISA for both benign and malignant ascites fluid, resulting in r values of 0.3084 and 0.2594, respectively (FIG. 2B).

Example 3: mAb-RA2 and mAb-RG2 Differentiate Functional from Non-Functional CXCL10

In addition to proteolytic N-terminal truncation of CXCL10, other post-translational modifications can influence CXCL10 activity (Mortier et al., 2011). In particular, deamination of arginine to citrulline (R5Cit) in the N-terminal region of CXCL10 is an established functional modification occurring in vivo, and thus must be accounted for in any assay to assess CXCL10 function (Mortier et al., 2011). The inventors therefore investigated whether the R5Cit modification may influence the detection of full-length CXCL10 by either mAb-RA2 or mAb-RG2.

Figure 3A:
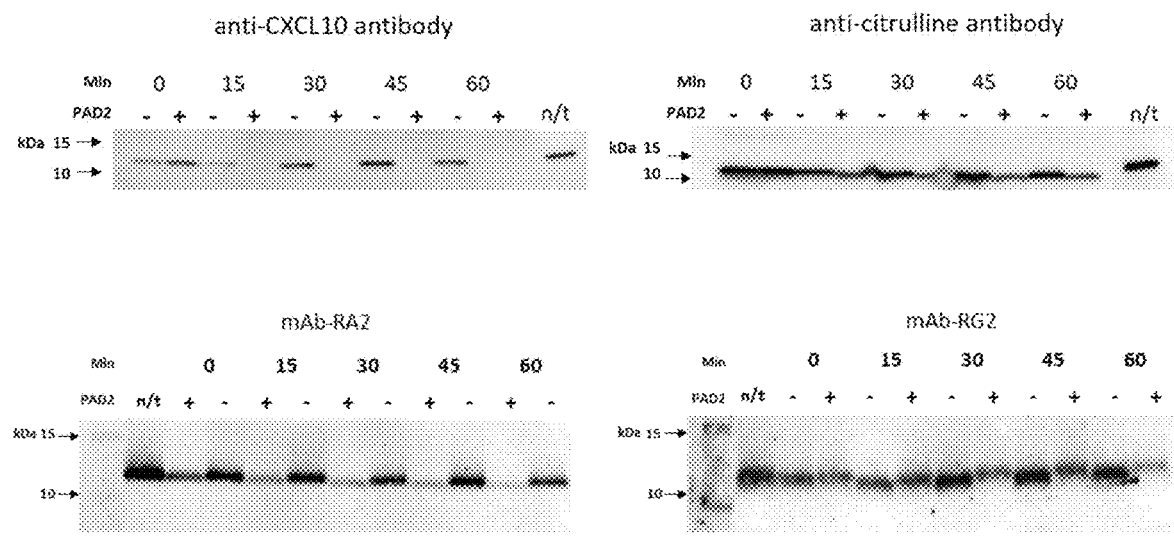
FIG. 3A shows Western blots demonstrating the detection of recombinant full length CXCL10 and citrullinated CXCL10 by mAb-RA2 and mAb-RG2. CXCL10 was treated with (+) or without (−) PAD2 to induce citrullination over 60 minutes and then separated by western blotting. Recombinant, full length CXCL10 without any treatment (n/t) was used as a positive control. Commercial anti-CXCL10 antibody (ab9807) did not detect citrullinated CXCL10 after 15 minutes into the PAD2 incubation period. Note that substantial reduction in detection by mAb-RA2 to citrullinated CXCL10 was observed after 15 minutes, and no effect of citrullination on CXCL10 detection by mAb-RG2 was observed.

Recombinant, full-length CXCL10 (SEQ ID NO:2) was incubated with protein-arginine deiminase 2 (PAD2) to induce deamination at R5, and proteins were separated by SDS PAGE and analysed by western blotting. In vitro citrullination had no effect on CXCL10 detection using mAb-RG2 (detecting total CXCL10), suggesting that mAb-RG2 bound to CXCL10 regardless of post-translational modification (FIG. 3A). By contrast, mAb-RA2 showed substantially reduced detection of R5Cit-CXCL10 (FIG. 3A) consistent with modification of the epitope following R5Cit modification at the N-terminus.

Figure 3B:
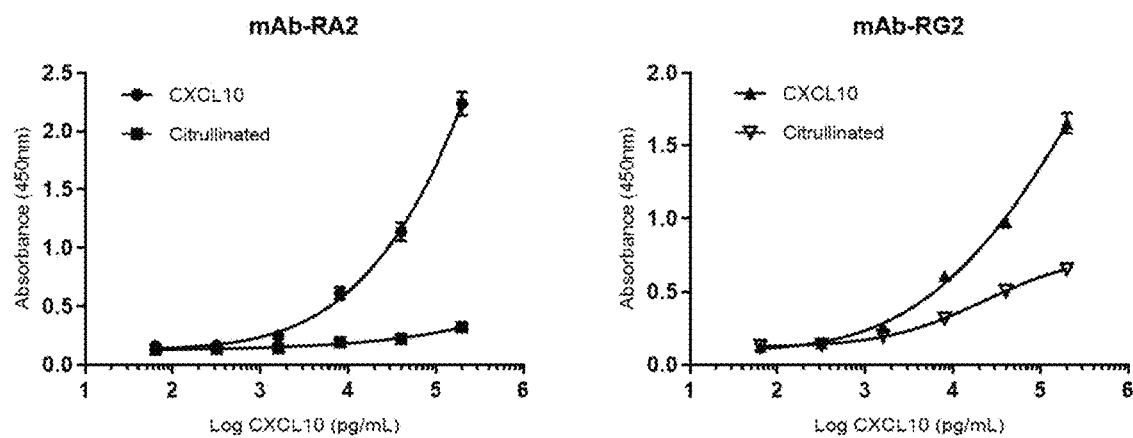
FIG. 3B shows detection of citrullinated CXCL10 by ART of mAb-RA2 and mAb-RG2. Substantial reduction in binding of citrullinated CXCL10 by mAb-RA2 was observed, whilst mAb-RG maintained a degree of binding to citrullinated CXCL10.

A similar result was obtained when R5Cit-CXCL10 was evaluated by ELISA. Citrullination substantially reduced binding of mAb-RA2, whilst mAb-RG2 remained able to detect R5Cit-CXCL10 (FIG. 3B). Together, the data demonstrate that mAb-RA2 and mAb-RG2 can be used effectively to differentiate active from total CXCL10.

Figure 4A:
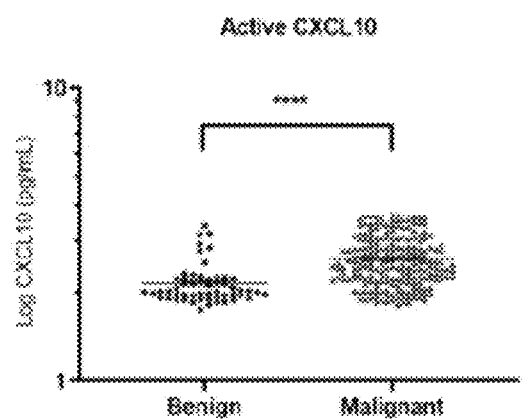
FIGS. 4A-4D show differentiation of benign from malignant ascites fluids from ovarian cancer patients through: quantitation of active and total CXCL10; and active CXCL10 ratio.
Figure 4B:
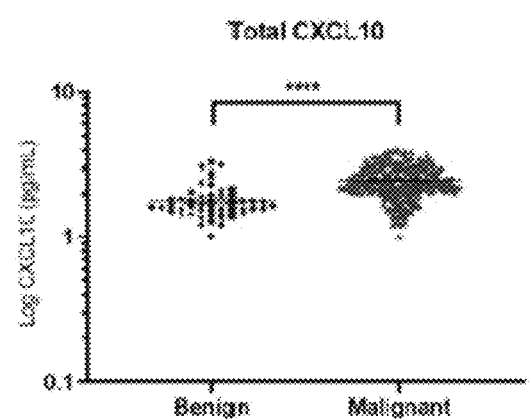

Example 4: Active Ratio Test Differentiates Benign from Malignant Ovarian Cancer Samples To establish the use of ART to discriminate between benign vs malignant disease, the inventors measured active vs total CXCL10 concentrations in ascites fluid harvested from patients with either benign or malignant ovarian tumours (Table 3). Total CXCL10 was elevated in malignant (853.1±1574.0 pg mL-1) compared to benign (160.8±362.0 pg mL-1) ascites fluid (FIG. 4B). Similarly, a broad range in active CXCL10 measurement was also observed (240.4±410.5 pg mL-1 and 818.6±1098.0 pg mL-1, respectively) (FIG. 4A). This broad deviation within the population (CV % ranging between 134.1 and 225.1%) results in low sensitivity for differentiation between benign and malignant samples (Table 5), and highlights the difficulties associated with the direct CXCL10 measurement for diagnostic or prognostic purposes.

Figure 4C:
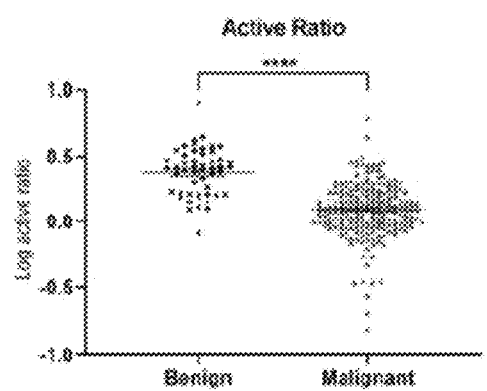
Figure 4D:
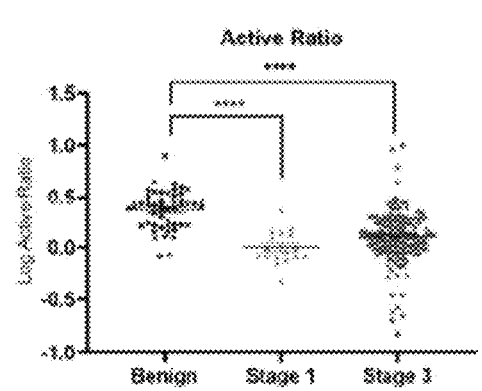
Figure 5C:
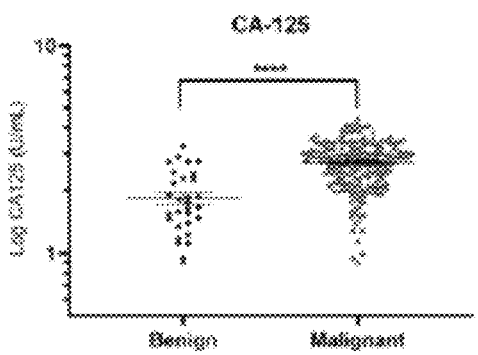
Figure 6A:
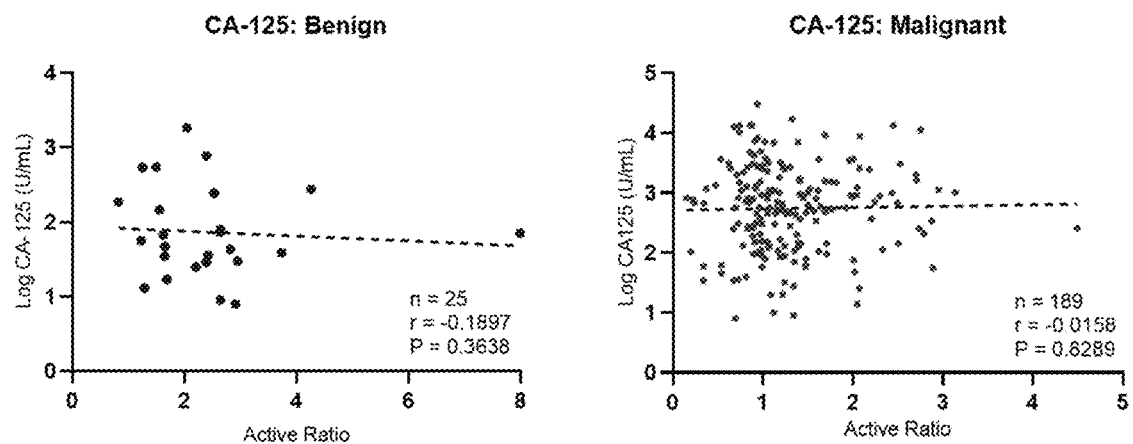
FIGS. 6A-6C show correlations between active ratio and: plasma CA125; DPP4 concentrations; and DPP4 specific activity in the benign and malignant ascites fluids.

Since proportionately greater levels of active CXCL10 were observed in benign vs malignant samples, the ratio of functional: total CXCL10 in each sample was examined, as a mechanism to normalize CXCL10 function between patients (FIG. 4C). This "active ratio" measurement significantly improved separation between the groups, resulting in differentiation between benign and malignant samples with cut-off values of <1.43 and <1.25 at 90% and 95% specificities, respectively (Table 5). This relationship also remained valid when malignant samples were separated according to disease stage (FIGO stage I vs stage III; FIG. 4D). Whilst plasma CA125 was significantly elevated in patient with malignant vs benign disease (FIG. 5C), there was no apparent correlation between active ratio measured in ascites fluid and plasma CA125 levels (FIG. 6A). Thus, active ratio provides a marker of malignancy independent of plasma CA125 concentration.

Example 5: DPP4 Abundance and Activity do not Correlate with Functional CXCL10

DPP4 catalyses the removal of a Val-Pro or Ala-Pro dipeptide form the N-terminus of CXCL10, converting it into an antagonist of T-cell recruitment. Previous work therefore sought to quantify the level of DPP4-cleaved CXCL10 in biological fluids as an indicator of disease (Casrouge et al., 2011 and 2012). However, multiple modifications to CXCL10—both proteolytic and non-proteolytic—can result in an expanded repertoire of CXCL10 variants beyond simple DPP4-catalysed N-terminal processing (Loos et al., 2008; Mortier et al., 2011). Failure to account for these multiple variants thus leads to discrepancies between the measured vs total amounts of CXCL10 in clinical samples and does not adequately capture the functional status of CXCL10 (Casrouge et al., 2012).

TABLE 5

Prognostic performance of active ratio and other biomarkers in the ascites fluid from ovarian cancer patients to distinguish between benign and malignant disease. The cutoff points of each biomarker were obtained based on the ROC analysis (at specificity 90 and 95%) to determine sensitivity, positive predictable value (PPV) and negative predictable value (NPV) accordingly.

| Biomarkers (Cutoff points) | Specificity % (95% CI) | Sensitivity % (95% CI) | AUC | PPV | NPV |
|---|---|---|---|---|---|
| Active Ratio | | | | | |
| <1.43 | 90.0 (78.6-95.7) | 63.5 (56.6-69.9) | 0.8617 | 80.4 | 79.2 |
| <1.25 | 96.0 (86.5-99.3) | 52.0 (45.1-58.8) | | 89.4 | 75.5 |
| Total CXCL10 (pg mL$^{-1}$) | | | | | |
| >241 | 90.2 (79.0-95.7) | 51.0 (44.2-57.6) | 0.8122 | 77.1 | 74.0 |
| >1204 | 94.1 (84.1-98.4) | 19.5 (14.7-25.4) | | 68.2 | 64.4 |
| Active CXCL10 (pg mL$^{-1}$) | | | | | |
| >598 | 90.1 (80.4-96.1) | 35.6 (29.4-42.3) | 0.7872 | 70.0 | 68.4 |
| >1400 | 94.6 (85.2-98.5) | 17.3 (12.8-23.0) | | 67.5 | 63.9 |
| DPP4 (ng mL$^{-1}$) | | | | | |
| >316 | 89.6 (77.8-95.5) | 12.2 (7.8-18.4) | 0.5598 | 43.2 | 61.2 |
| >389 | 95.8 (86.0-99.3) | 7.4 (4.2-12.8) | | 53.3 | 61.5 |
| Plasma CA125 (U mL$^{-1}$) | | | | | |
| >548 | 90.0 (73.5-97.9) | 52.1 (44.7-59.5) | 0.8262 | 77.1 | 74.4 |
| >757 | 93.3 (77.9-99.2) | 44.7 (37.4-52.1) | | 89.8 | 73.0 |
| Combined Biomarkers | | | | | |
| Active ratio & DPP4 (<1.43 and >316 ng mL$^{-1}$) | 91.7 (73.0-99.0) | 77.3 (68.3-84.7) | 0.9114 | 85.8 | 86.2 |
| Active ratio & DPP4 (<1.25 and >389 ng mL$^{-1}$) | 95.8 (78.9-99.9) | 67.3 (57.7-75.9) | | 91.2 | 81.9 |
| Active ratio & plasma CA125 | 91.7 (70.3-86.3) | 79.1 (70.3-86.3) | | 86.1 | 87.1 |

TABLE 5-continued

Prognostic performance of active ratio and other biomarkers in the ascites fluid from ovarian cancer patients to distinguish between benign and malignant disease. The cutoff points of each biomarker were obtained based on the ROC analysis (at specificity 90 and 95%) to determine sensitivity, positive predictable value (PPV) and negative predictable value (NPV) accordingly.

| Biomarkers (Cutoff points) | Specificity % (95% CI) | Sensitivity % (95% CI) | AUC | PPV | NPV |
|---|---|---|---|---|---|
| (<1.43 and >548 U mL$^{-1}$) | | | 0.9337 | | |
| Active ratio & plasma CA125 (<1.25 and >757 U mL$^{-1}$) | 95.8 (78.9-99.9) | 51.8 (42.1-61.5) | | 88.9 | 75.4 |
| Active ratio & DPP4 & plasma CA125 (<1.43 and >316 ng mL$^{-1}$ and >548 U mL$^{-1}$) | 91.7 (73.0-99.0) | 90.0 (82.8-94.9) | | 87.5 | 93.4 |
| Active ratio & DPP4 & plasma CA125 (<1.25 and >389 ng mL$^{-1}$ and >757 U mL$^{-1}$) | 95.8 (78.9-99.9) | 81.8 (73.3-88.5) | 0.9511 | 93.4 | 94.7 |

Note:
Prevalence of EOC in the patient cohort was taken into account to determine positive predictable value (PPV) and negative predictive value (NPV) at 90% and 95% specificities.

To clarify the relationship between DPP4 activity and CXCL10 function in clinical samples, we measured DPP4 abundance and specific activity in the same set of benign and malignant ascites.

Receiver operating characteristic (ROC) curve of each marker (active ratio, DPP4, CA125) was first constructed based on the results of the patients' samples to obtain area under curve (AUC). To obtain the combined ROC, binary logistic regression was performed; the measurements of each marker as dependent variables for both benign and malignant groups were used to obtain the probability as the test variable which is subsequently used to construct combined ROC.

Figure 5A:
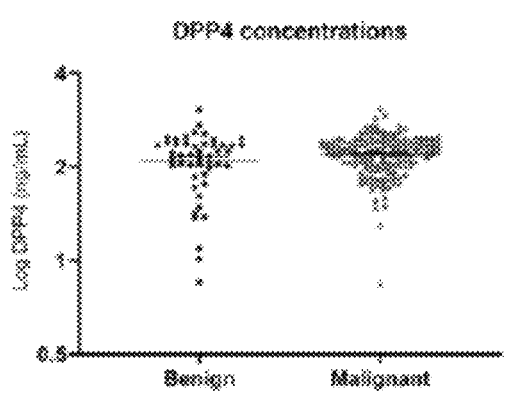
FIGS. 5A-5C show DPP4 and plasma CA125 in differentiating benign from malignant.
Figure 5B:
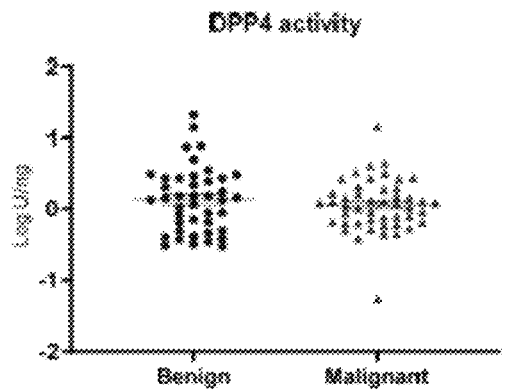
Figure 6B:
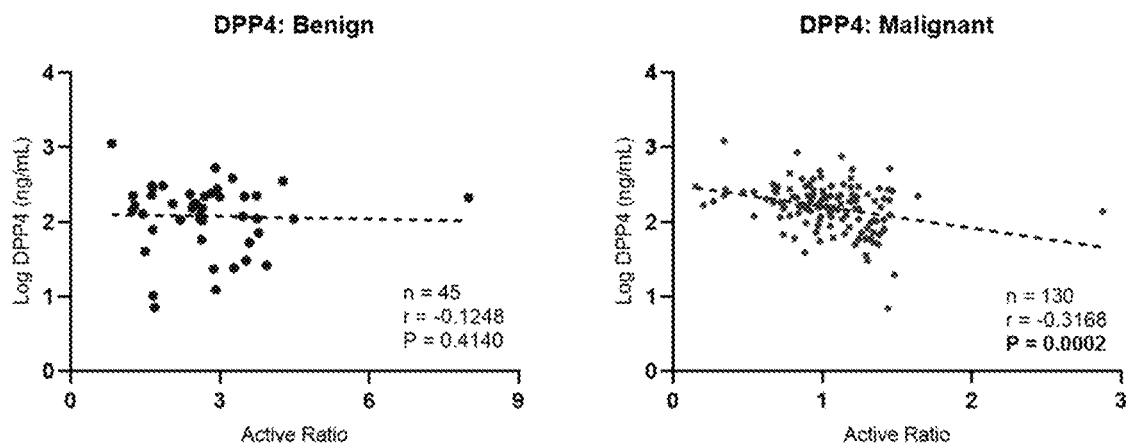
Figure 6C:
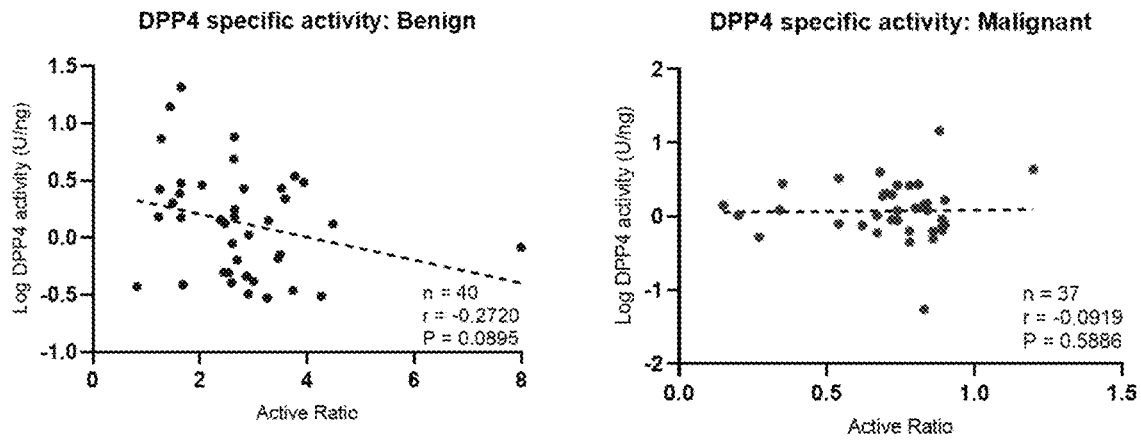

There was no significant difference in abundance or activity observed in either case (FIG. 5A and FIG. 5B). Whilst DPP4 abundance correlated (p=0.002) with the calculated active ratio in malignant samples, its specific activity did not; interestingly, benign samples displayed an inverse (non-significant) trend suggesting a correlation between specific activity and active ratio measurement (FIG. 6B and FIG. 6C). These data suggest that whilst DPP4 activity may be related to CXCL10 function in non-malignant disease, multiple CXCL10 variants are likely to be important in determining the overall functional status of CXCL10 in malignancy.

Figure 7A:
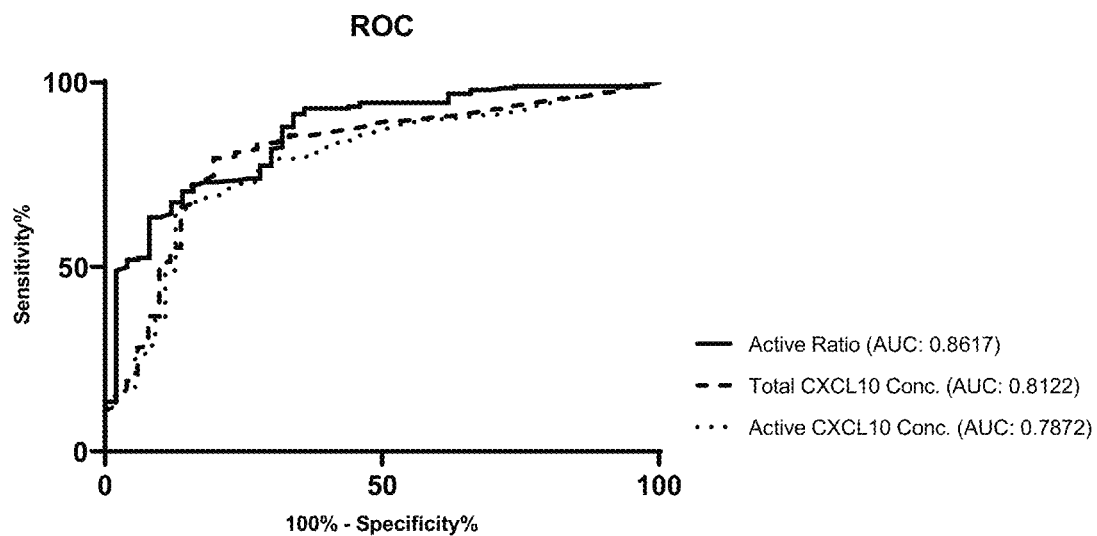
FIGS. 7A-7B show receiver operator curves (ROC) analysis demonstrating superior AUC for ART vs other markers in patient ascites samples.
Figure 7B:
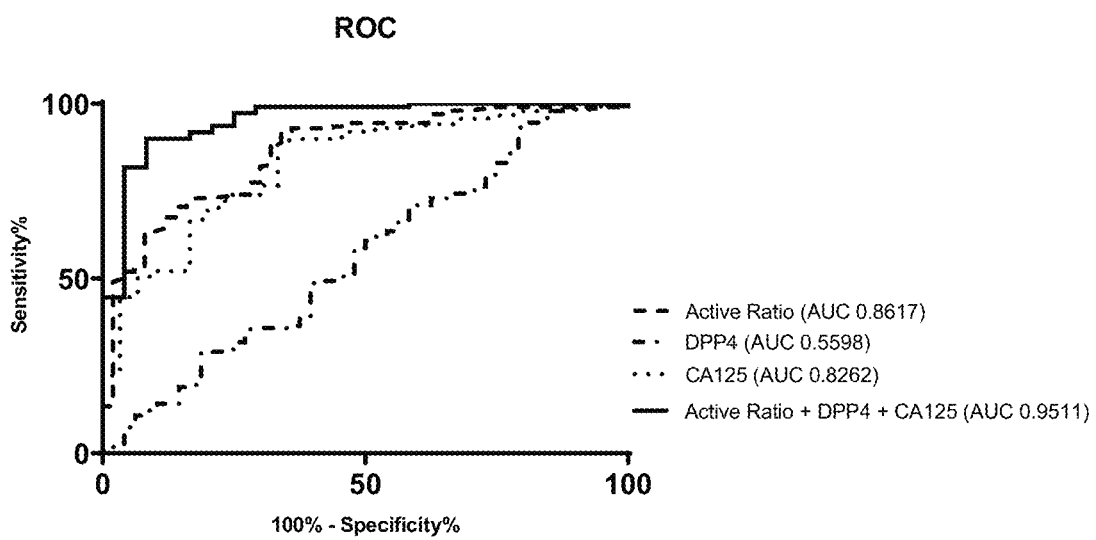

Example 6: Active Ratio Provides Prognostic Discrimination Between Benign and Malignant Disease To evaluate whether the active ratio could provide useful clinical information, we assessed its performance in ascites fluid using receiver operating characteristic (ROC) curves (FIGS. 7A-7B). Active ratio achieved higher AUC and a substantial improvement in sensitivity/specificity compared to measurement of either active or total CXCL10 alone (FIG. 7A; Table 3), highlighting its enhanced utility over these single measurements. Sensitivity, specificity and predictive values of active ratio were also higher than plasma CA125 (FIG. 7B; Table 3). Active ratio also achieved greater effect size (Cohen's d) than either DPP4, CA125 or CXCL10 (active or total) measurements alone (Table 4). Accordingly, the combination of active ratio, DPP4 and plasma CA125 measurement yielded an AUC >0.95 with good PPV (87-94%) and NPV (93-95%) for the discrimination between benign and malignant disease. Thus, the combination of ART with DPP4 and plasma CA125 provided useful in the discrimination between benign and malignant disease in patients presenting with ascites fluid.

TABLE 6

Effect sizes of biomarkers based on sample types. The values of AUC, Cohen's d, and CV % were obtained, independent of the cutoff points. P values are based on ROC analysis.

| Biomarker | Sample type | AUC | Cohen's d | CV % (malignant) | P value |
|---|---|---|---|---|---|
| Total CXCL10 (pg/mL) | Ascites | 0.8122 | 0.6976 | 191.7 | <0.0001 |
| Active CXCL10 (pg/mL) | Ascites | 0.7872 | 0.6062 | 134.1 | <0.0001 |
| Active Ratio | Ascites | 0.8617 | 0.8629 | 72.7 | <0.0001 |
| Active Ratio | CVS | 0.8036 | 1.0074 | 54.4 | <0.0001 |
| Active Ratio | Plasma | 0.7828 | 0.7905 | 52.0 | 0.0002 |
| DPP4 (ng/mL) | Ascites | 0.5598 | 0.1124 | 75.8 | 0.2139 |
| CA125 | Plasma | 0.8262 | 0.6171 | 200.9 | <0.0001 |

Example 7: ART as a Clinical Diagnostic

The inventors explored whether active ratio measurements could be performed using cervicovaginal swabs (CVS) representative of the reproductive tract.

Figure 8A:
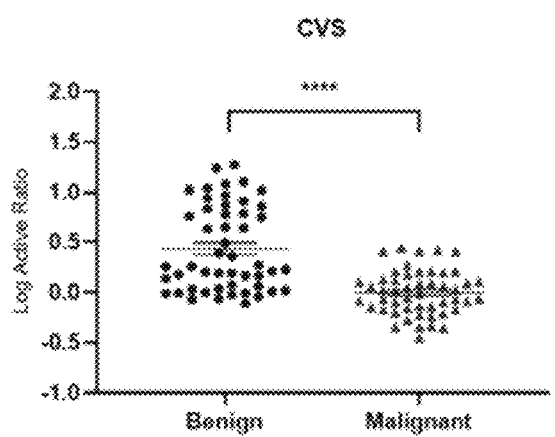
FIGS. 8A-8B show demonstration of cervicovaginal swabs (CVS) and plasma that are ideal for ART as biomarker-based testing.
Figure 8B:
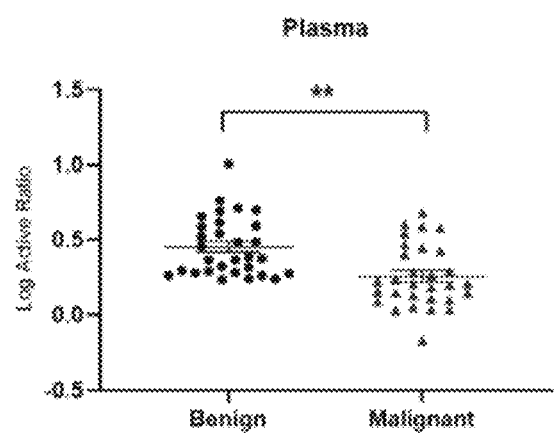

In parallel to our findings in ascetic fluid, active ratio measurement performed on CVS extracts (n=50/group) displayed good discrimination between benign and malignant disease samples with an AUC of 0.8 (p<0.0001) (FIG. 8A; Table 6). In matched plasma samples (n=30), ART was also able to discriminate between groups (AUC 0.8, p<0.001).

To explore diagnostic utility beyond ROC analyses, the inventors also examined effect size (Cohen's d) for each biomarker and sample type (Table 6). Measurement of plasma CA125 returned an AUC of 0.83, second only to ART measurement in ascites fluid (AUC 0.86); however, the effect size was "medium" (Cohen's d=0.62). By contrast, ART measurements achieved "large" effect sizes in ascites fluid and CVS (Cohen's d=0.86 and 1.0 respectively) suggesting greatly reduced deviation within the same population. Similarly, ART measurement performed in plasma returned a Cohen's d=0.79 (Table 6).

This result indicates that ART is the preferred biomarker to achieve statistically robust measurements, and that its analysis using CVS can provide a robust and clinically useful measurement to discriminate between malignant and non-malignant disease.

Example 8: ART Discriminates Cancer-Free Patients from Patients with Benign or Malignant Ovarian Tumours After establishing the application of ART to discriminate between patients with benign and malignant ovarian tumours through active ratio, ART was applied to test a new patient cohort (i.e. prophylactically collected cohort)—patients who underwent prophylactic, risk-reducing salpingoorphorectomy who are either confirmed BRCA1/2 mutation carriers, or have a strong familial history of breast and/or ovarian cancer. These patients thus represent an ideal no-disease control cohort for the validation of ART designed to detect the presence of early stage ovarian cancers.

Figure 9A:
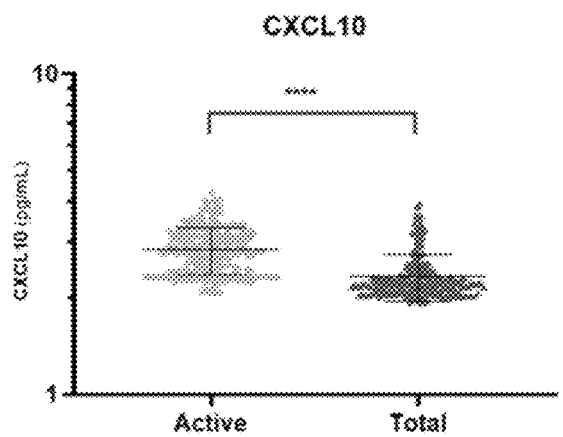
FIGS. 9A-9D show ART discriminates cancer-free patients from patients with benign conditions or malignant ovarian cancers.
Figure 9B:
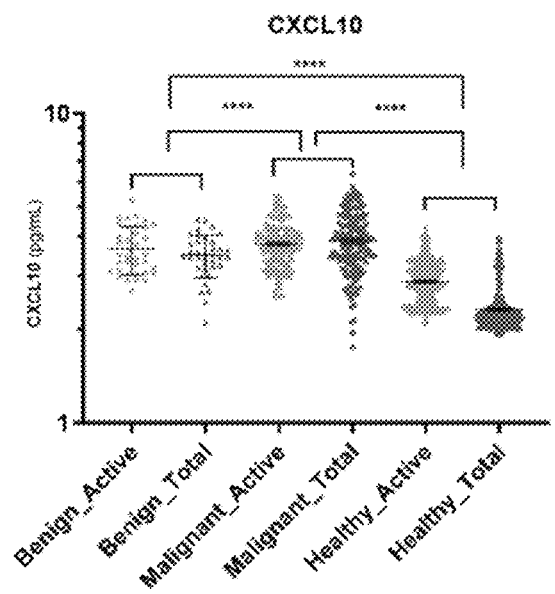
Figure 9C:
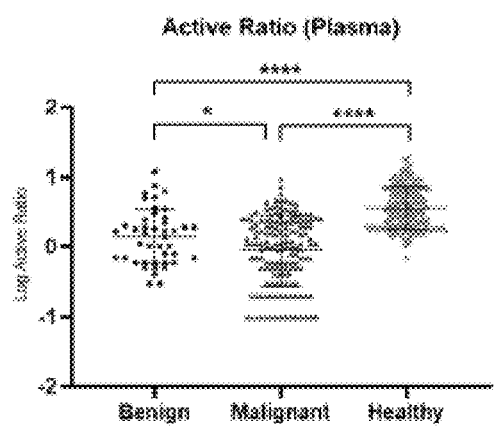
Figure 9D:
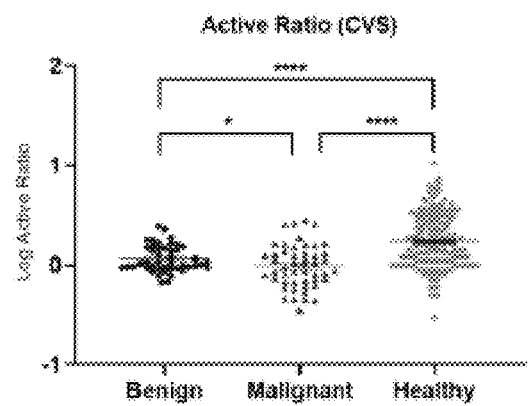

The concentration of active CXCL10 was significantly higher than total CXCL10 in the healthy women (FIG. 9A), suggesting that patients free of cancers may have higher level of active, functional CXCL10. When the overall active and total CXCL10 concentrations in healthy women in the prophylactically collected cohort were compared to the respective CXCL10 concentrations of benign and malignant, they were significantly lower than both the benign and malignant (FIG. 9B). As for active ratios, active ratios in the healthy women were significantly higher than benign and malignant groups in both plasma and CVS (FIGS. 9C and 9D).

Given that the level of active CXCL10 and active ratio of the healthy women are significantly higher than total CXCL10 and active ratios of benign and malignant patients, respectively, the data suggests that there may be lesser degree of DPP4-initiated cleavage of functional CXCL10 in the patients free of benign conditions or malignant ovarian tumours.

Example 9: DPP4 Abundance and Activity do not Correlate with Active Ratio

To establish the relationship between DPP4 and CXCL10 in the prophylactically collected cohort, DPP4 abundance and its specific activity in the plasma samples was measured and compared to the results of patients with benign or malignant ovarian cancers.

Figure 10A:
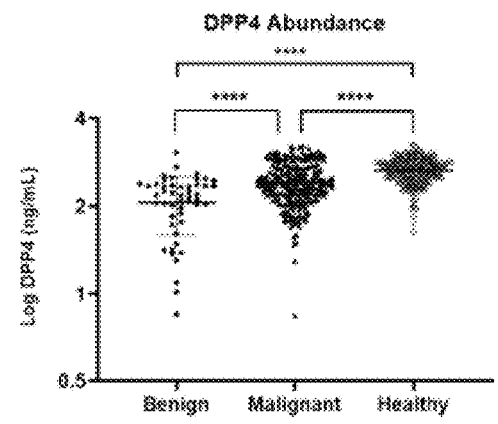
FIG. 10A shows DPP4 abundance in the prophylactically collected cohort.
Figure 10B:
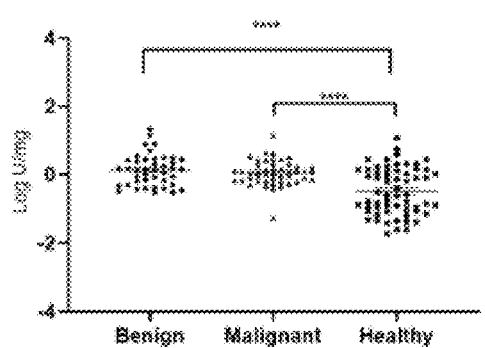
FIG. 10B shows DPP4 specific activity in the prophylactically collected cohort.
Figure 10C:
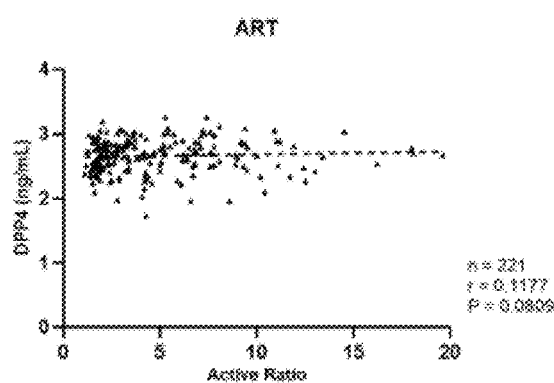
FIG. 10C shows DPP4 abundance correlations with active ratio.
Figure 10D:
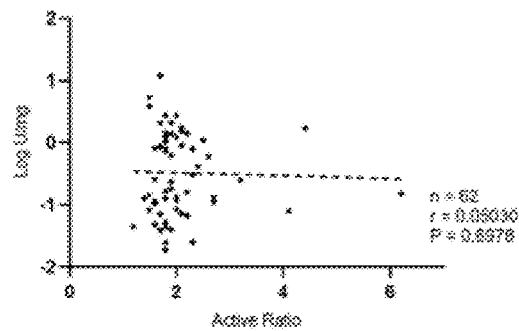
FIG. 10D shows DPP4 specific activity correlations with active ratio.

The level of DPP4 in the healthy patients' plasma samples was significantly higher than both the benign and malignant patient groups. However, DPP4 abundance did not correlate with the calculated active ratio in those healthy women's samples (FIG. 10A). Despite the level of DPP4 in the healthy women was significantly higher than the benign and malignant patient groups, its specific activity in the plasma of healthy women was significantly lower than both the benign and malignant (FIG. 10Bb). Specific activity did not correlate with the calculated active ratio either. These data suggest that the function of DPP4 in healthy women may be suppressed by an unknown factor.

Example 10: CVS Discriminates Healthy Women from Patients with Benign or Malignant Ovarian Tumours As CVS is a sample of choice for biomarker-based testing, the level of active and total CXCL10 concentrations in CVS of the prophylactically collected cohort were measured to obtain active ratios. Furthermore, comparison of active ratios was done between healthy patients in the prophylactically collected cohort and the patients with benign or malignant ovarian tumours.

Figure 11A:
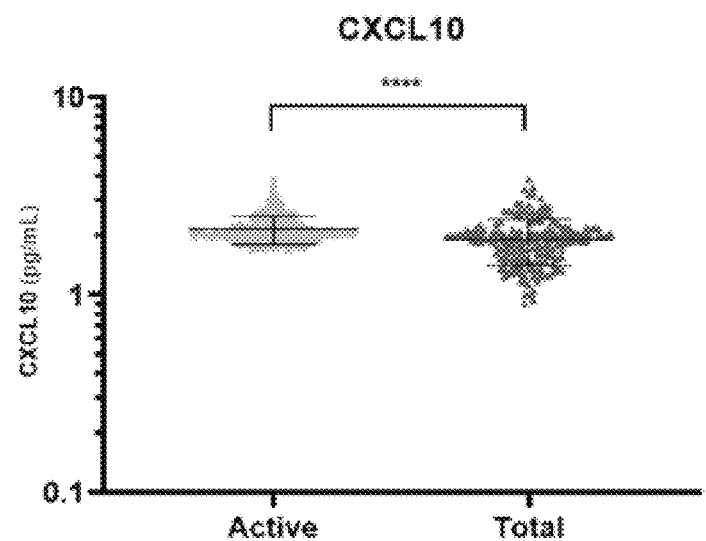
FIGS. 11A-11B show ART performed using CVS swabs discriminated between cancer-free and benign and malignant disease.
Figure 11B:
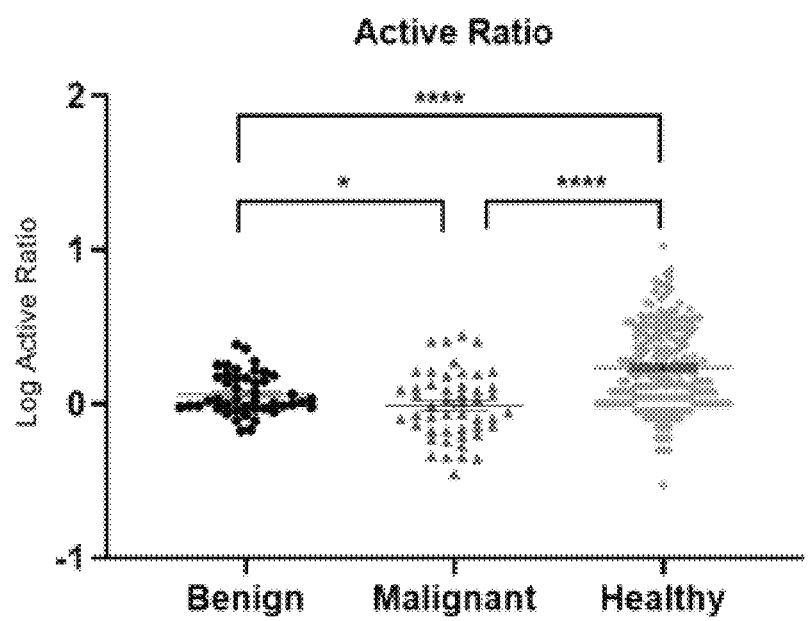

As for the healthy women, the overall level of active, functional CXCL10 was significantly higher than total CXCL10 (FIG. 11A). As opposed to patients with benign or malignant ovarian tumours, the calculated active ratio of healthy patients' CVS was in line with the plasma results; the overall active ratio of samples from healthy women was significantly higher than both benign and malignant patient groups (FIG. 11B).

Example 11: DPP4 Abundance of CVS and its Correlation with Active Ratio of CVS

Figure 12A:
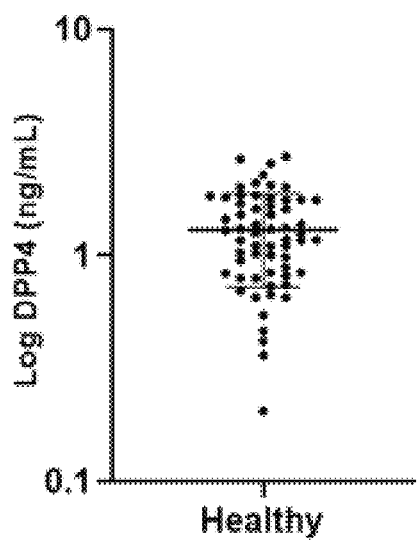
FIG. 12A shows DPP4 abundance on CVS, and FIG. 12B show DPP4 abundance correlation with calculated active ratio of CVS.
Figure 12B:
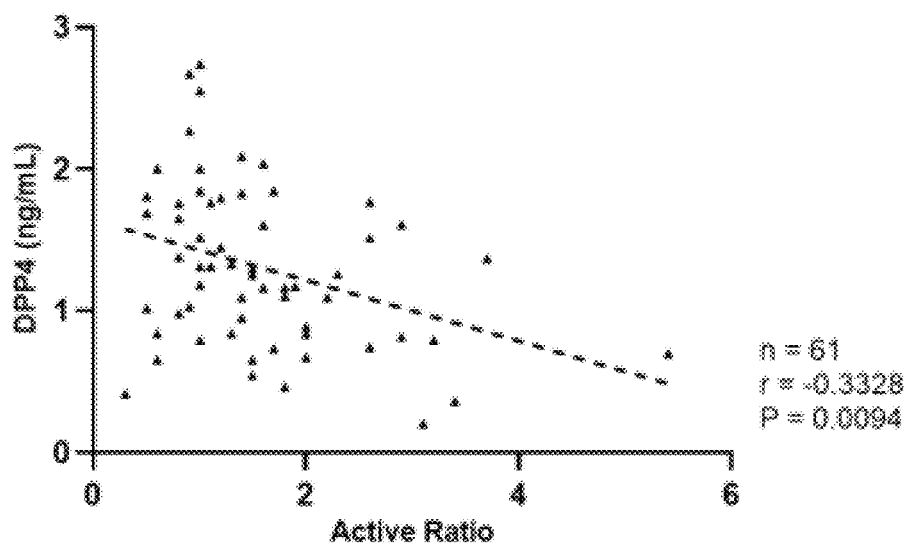

DPP4 abundance on CVS was not measured in the previous study involving Ovarian Cancer Biobank due to limited quantity of extracts from CVS. As it is desirable to measure both active ratio and DPP4 abundance from the same sample source and establish their correlations within the same sample type, preparation of CVS was optimised to measure both active ratio and DPP4 of CVS and thus correlate them. As shown in FIGS. 12A-12B, DPP4 of CVS could be quantitated and the calculated active ratio inversely correlated with DPP4 (p=0.0094). This data suggests the feasibility of correlating active ratio with DPP4 of CVS.

Example 12: Active Ratio and Plasma CA125

Figure 13A:
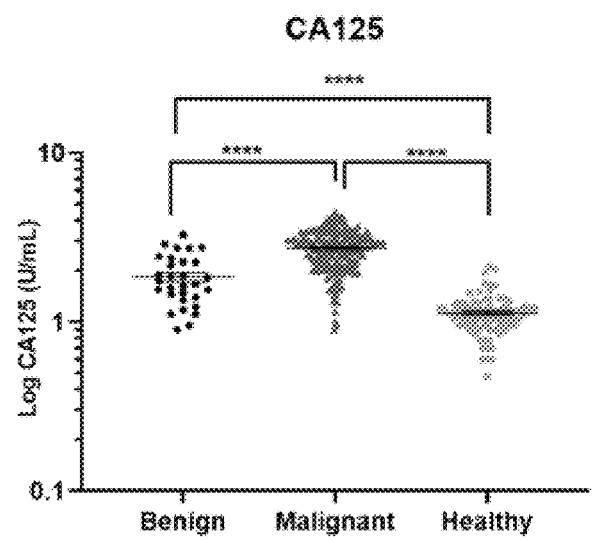
FIG. 13A shows Plasma CA125 in the prophylactically collected cohort against patients with either benign or malignant ovarian tumours.
Figure 13B:
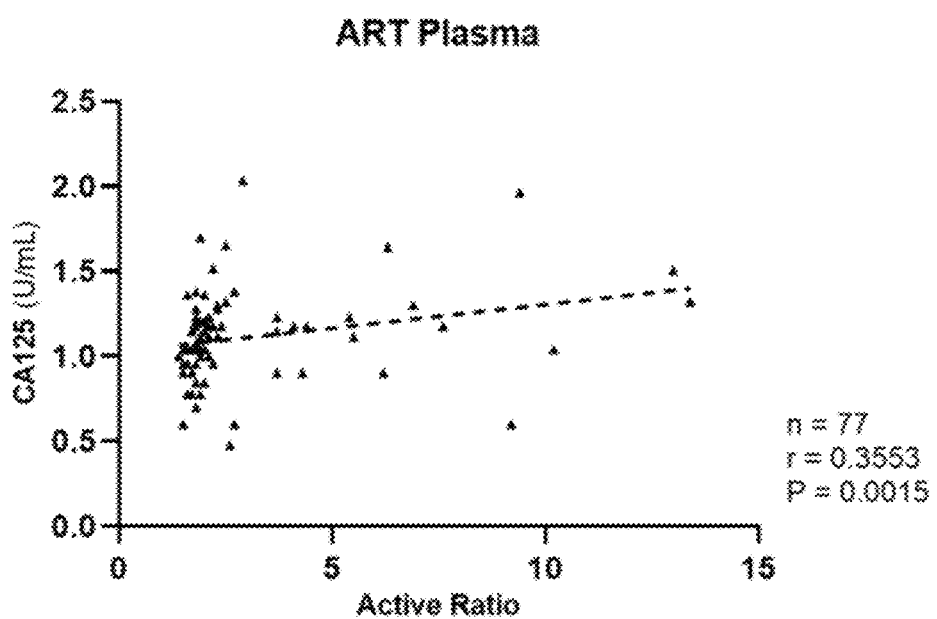
FIG. 13B shows correlation between CA125 and active ratio.

CA125 measurements of healthy women were significantly lower than both the benign and malignant groups. The data is in line with the fact that the level of CA125 is elevated in patients with malignant diseases (FIGS. 13A-13B). Calculated active ratio positively correlated with CA125 (p=0.0015).

Example 13: Active Ratio and Plasma CA125

To evaluate whether the active ratio could provide useful clinical information, its performance in plasma and CVS was assessed using receiver operating characteristic (ROC) curves. ROC curves were constructed based on the comparison between the healthy women in the prophylactically collected cohort vs the patients with malignant ovarian tumours.

Figure 14A:
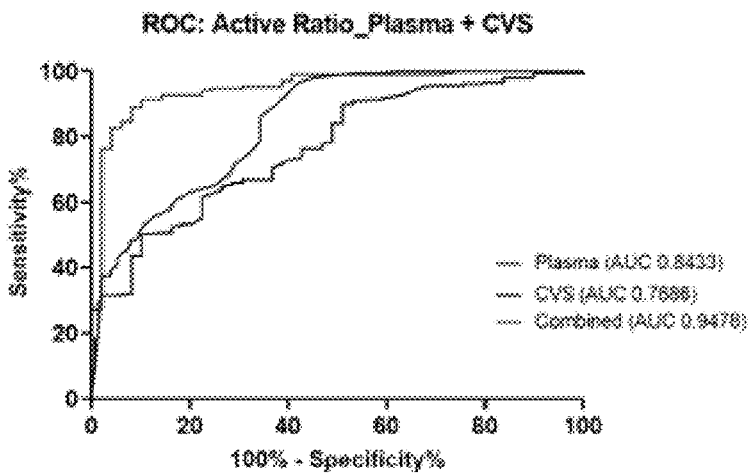
FIG. 14A shows combination of active ratio of plasma and CVS, where each discriminated between healthy women and patients with malignant ovarian tumours.
Figure 14B:
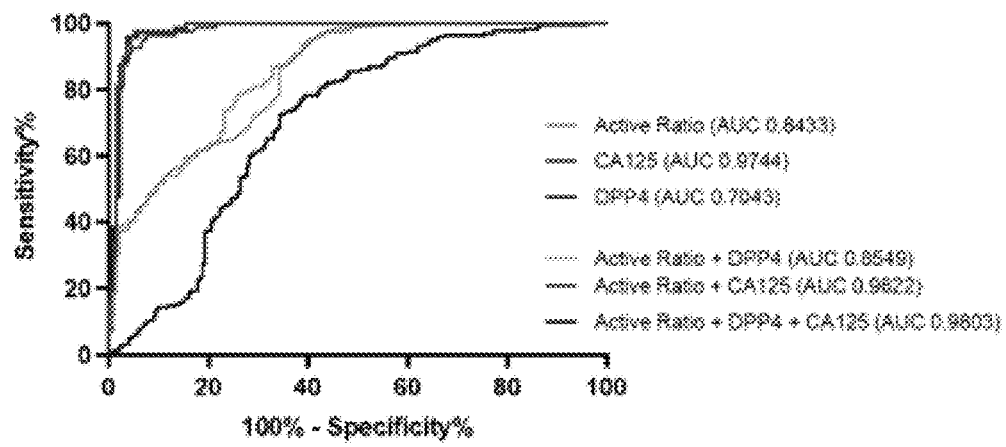
FIG. 14B shows combination of active ratio of plasma with DPP4 and CA125, where each discriminated between healthy women and patients with malignant ovarian tumours.
Figure 14C:
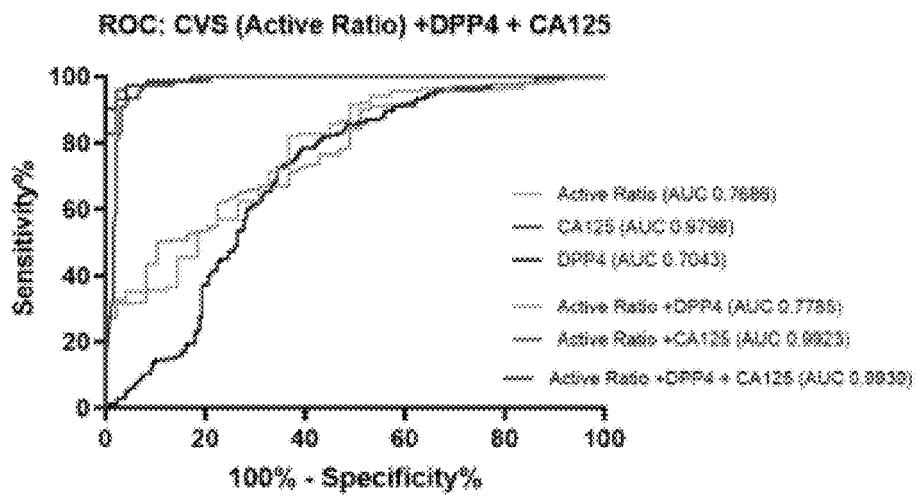
FIG. 14C shows combination of active ratio of CVS with DPP4 and CA125, where each discriminated between healthy women and patients with malignant ovarian tumours.

As active ratio had achieved a substantial improvement in sensitivity/specificity compared to quantitation of either active or total CXCL10 alone in the previous ascites study, combining active ratios of plasma and CVS also achieved a higher AUC (FIG. 14A). This validates the use of both sample types to increase the prognostic efficacy of ART. The combination of active ratio of plasma, DPP4, and plasma CA125 measurement yielded an AUC >0.98 (FIG. 14B) whilst the combination of active ratio of CVS, DPP4, and plasma CA125 yielded an AUC >0.99 for the discrimination between healthy women and malignant disease. These data suggest that combination of active ratio with DPP4 and plasma CA125 along with combining the two sample types prove to be useful in the discrimination between healthy women and malignant disease.

Figure 15A:
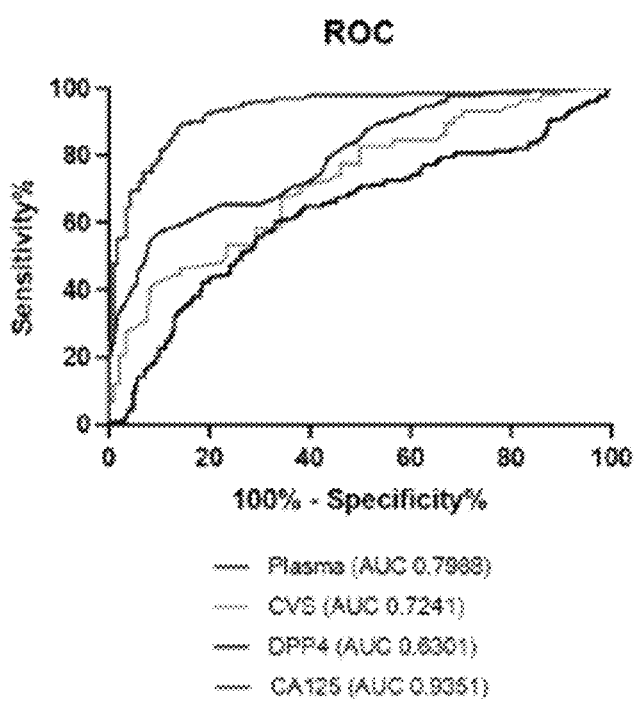
FIG. 15A shows ROC to evaluate the discriminatory power of individual markers in comparison to CA125.
Figure 15B:
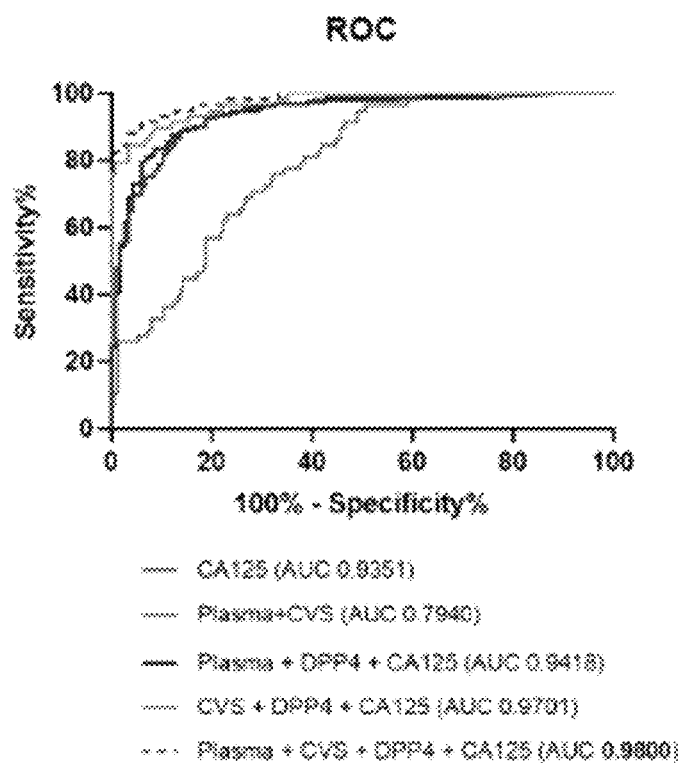
FIG. 15B shows ROC to evaluate the discriminatory power of combinations of markers (Constructed based on benign+ healthy vs malignant).

Example 14: ART Differentiates Patients with Malignancy Against a Complex Background To investigate the prognostic potential of ART to identify malignancy against a diverse background, women in the healthy and benign cohorts were combined and ROC analyses performed against the malignant group. ART alone returned an AUC of 0.79 when applied to plasma samples and an AUC of 0.72 when applied to CVS samples. By comparison, CA125 achieved an AUC of 0.93 (FIG. 15A). However, CA125 exhibited high variation within the cohort (CV 189.5%) and a small effect size (Cohen's d 0.097), suggesting it was not a robust measurement for differentiation of malignant samples from the combined healthy plus benign cohort (Table 7).

By contrast, active ratio measurements had large effect size in both CVFS (d=0.64) and plasma (d=1.01), suggesting greatly reduced deviation within the same population (Table 7). This result suggests that ART can achieve statistically robust measurements, and can out-perform the current CA125 gold standard for the differentiation of malignant ovarian cancer against a complex background of healthy women or patients with benign disease.

TABLE 7

Effect sizes of individual biomarkers for the differentiation of malignant disease against a complex background cohort.

| Biomarker | AUC | Cohen's d | CV % | P value |
|---|---|---|---|---|
| Active Ratio (Plasma) | 0.7988 | 1.0168 | 97.3 | <0.0001 |
| Active Ratio (CVS) | 0.7241 | 0.6383 | 73.9 | <0.0001 |
| DPP4 (ng mL − 1) | 0.6301 | 0.3078 | 91.2 | <0.0001 |
| CA125 | 0.9351 | 0.0996 | 189.5 | <0.0001 |

The combination of ART (CVS and/or plasma), DPP4, and CA125 was also examined as a mechanism to improve differentiation between groups. Compared to CA125 (AUC 0.94), the combination of ART measured using CVS with all other markers measured in plasma returned an AUC of 0.98 (Table 8).

The combination of all biomarkers (ART, DPP4 and CA125) achieved an AUC of 0.98 with a sensitivity of 93.1% for detection of malignancy within this cohort (Table 8). By contrast, CA125 alone exhibited an AUC of 0.94 but sensitivity of only 78.6% (Table 8).

TABLE 8

Prognostic performance of individual markers and combined markers to distinguish malignant disease from a patient cohort comprised of healthy women and women with benign gynaecological disease.

| Individual Biomarker (cutoff points) | AUC | Sensitivity % | Specificity % |
|---|---|---|---|
| Active Ratio (Plasma) (<1.25) | 0.7988 | 56.3 | 90.8 |
| Active Ratio (CVS) (<0.89) | 0.7241 | 41.4 | 91.6 |
| DPP4 (ng mL − 1) (<119.4) | 0.6301 | 20.1 | 90.0 |
| CA125 (>138.5) | 0.9351 | 78.6 | 90.6 |
| Combined Biomarkers | | | |
| Active Ratio (Plasma) + DPP4 + CA125 (<1.25 and <119.4 and >138.5) | 0.9418 | 83.4 | 90.6 |
| Active Ratio (CVS) + DPP4 + CA125 (<0.89 and <119.4 and >138.5) | 0.9701 | 89.7 | 90.6 |
| Active Ratio (Plasma + CVS) + DPP4 + CA125 (<1.25 and <0.89 and <119.4 and >138.5) | 0.9800 | 93.1 | 90.6 |

Thus, the combination of ART, DPP4 and CA125 differentiated malignancy against a complex background comprised of healthy women and women with benign disease; and significantly out-performed CA125 alone, the current clinical gold standard.

Example 15: ART Improves Identification of Early Stage (Stage I) Cancer Patients Cancer stage at diagnosis is strongly associated with clinical outcomes for ovarian cancer patients. In particular, patients diagnosed with FIGO stage I disease ("early stage") have substantially improved 5-year and overall survival rates (~95%) compared to those diagnosed at stage III-IV (<40%). Accordingly, it was assessed whether ART (singly or in combination) could successfully differentiate early stage cancer patients from either healthy women or women with benign disease.

CA125 gave the greatest single-marker differentiation between early stage cancer patients and those with benign disease or healthy women (Table 9). However, the combination of ART (plasma) with DPP4 and CA125 substantially improved differentiation between benign vs early stage malignancy (AUC 0.75 vs 0.63; Table 9).

Strikingly, patients with early stage malignancy could be differentiated from healthy women with high accuracy using the 3-marker combination (AUC=0.99; sensitivity 95.4%), compared to CA125 alone (AUC 0.88; sensitivity 81.8%).

ART can thus be used to improve diagnostic or prognostic evaluation of patients, and particularly for the detection disease-specific changes associated with early stage cancers, compared to the current CA125 gold standard.

TABLE 9

Prognostic performance of individual markers and combined markers to identify stage 1 cancers.

| Benign vs Stage I | AUC | Sensitivity % | Specificity % |
|---|---|---|---|
| Active Ratio (Plasma) (<0.55) | 0.5356 | 31.2 | 88.4 |
| DPP4 (ng mL − 1) (>335.3) | 0.5770 | 25.0 | 89.8 |
| CA125 (>532.5) | 0.6250 | 22.3 | 88.9 |
| Active Ratio (Plasma) + DPP4 + CA125 (<0.55 and >335.3 and >532.5) | 0.7463 | 50.0 | 90.7 |
| Healthy vs Stage I | | | |
| Active Ratio (Plasma) (<1.65) | 0.7661 | 50.0 | 90.0 |
| DPP4 (ng mL − 1) (>69.1) | 0.8794 | 75.0 | 90.0 |
| CA125 (>31.5) | 0.8830 | 81.8 | 90.1 |
| Active Ratio (Plasma) + DPP4 + CA125 (<1.65 and >69.1 and >31.5) | 0.9888 | 95.4 | 90.1 |

Example 16: A Combination of ART Panel and a Multiplex 5-Marker Panel Identifies Patients with Pre-Cancerous Lesions in a Prospectively Collected Cohort Whilst the etiology of ovarian cancers remains unclear, it is now evident that the formation of many ovarian tumours begins with the presence of a pre-cancerous "p53 signature" in the fallopian tube. Similar to other cancer types, detection of lesions at a very early—or pre-cancerous—stage would enable substantially improved outcomes.

The inventors previously identified several additional biomarkers (GM-CSF, IL-6, TNF-RII, HE4, IL8) relevant for diagnostic profiling of high grade epithelial ovarian cancers (PMID: https://doi.org/10.1038/s41598-020-59009-z). Accordingly, the combination of these with the existing panel of ART, DPP4 and CA125 was assessed for their potentially improved diagnostic performance.

For these studies, marker combinations were assessed in a prospectively collected cohort of women who underwent prophylactic risk-reducing surgery (typically bilateral-salpingo-oophorectomy) for known hereditary risk of ovarian cancer development. Histological evaluation was used to classify all patients as either "healthy" (i.e. confirmed absence of disease) or "cancer" (presence of a p53 lesion or early stage occult tumour).

Results are shown in Table 10 (only the best performing combinations are shown). The 5-marker panel returned a combined AUC of 0.87 for the detection of early stage/pre-cancerous lesions; whilst the established ART panel achieved an AUC of 0.97 (Table 10). These were substantially better than CA125, which returned an AUC of 0.77.

Strikingly however, when both panels were combined a perfect AUC of 1.0 was achieved demonstrating that this specific combination of markers has high potential for the diagnosis of early-stage and pre-cancerous lesions of the ovaries.

TABLE 10

Prognostic performance of individual markers and combined markers to identify patients with stage 1 cancers or p53 pre-cancerous lesions.

| Multiplex 5 marker panel | AUC | Sensitivity % | Specificity % |
|---|---|---|---|
| GM-CSF | 0.5564 | 22.2 | 92.6 |
| IL-6 | 0.7816 | 44.4 | 90.1 |
| TNF-RII | 0.5317 | 11.1 | 90.1 |
| HE4 | 0.8377 | 44.4 | 90.1 |
| IL-8 | 0.6495 | 33.3 | 90.1 |
| Combination of five* | 0.8645 | 77.8 | 90.1 |
| ART panel | | | |
| Active Ratio (Plasma) | 0.6846 | 36.4 | 90.0 |
| Active Ratio (CVS) | 0.5802 | 20.0 | 90.0 |
| DPP4 | 0.5906 | 25.0 | 90.1 |
| CA125 | 0.7677 | 54.6 | 90.1 |
| Combination of four* | 0.9676 | 87.5 | 90.1 |
| Multiplex added to: | | | |
| Active Ratio (plasma + CVS) | 0.9238 | 77.8 | 90.1 |
| Active Ratio (plasma + CVS) + DPP4 | 0.9329 | 75.0 | 90.0 |
| Active Ratio (plasma + CVS) + CA125 | 0.9833 | 88.9 | 90.0 |
| Active Ratio (Plasma + CVS) + DPP4 + CA125 | 1.0000 | | |

REFERENCES

Al-Lazikani et al. (1997) J Mol Biol, 273:927-948.
Armour et al. (1999) Eur J Immunol, 29:2613-2624.
Ausubel et al. Current Protocols in Molecular Biology, 1987, Wiley Interscience, ISBN 047 150338.
Ausubel et al. (ed.), Current Protocols in Molecular Biology, 1988, John Wiley and Sons, Inc.
Bork et al. (1994) J Mol Biol, 242:309-320.
Brady et al. (1987) Philosophical Transactions of the Royal Society, B316:143-160.
Brown (ed.), Essential Molecular Biology: A Practical Approach, 1991, IRL Press, Volumes 1 and 2.
Casrouge et al. (2011) The Journal of Clinical Investigation, 121:308-317.
Casrouge et al. (2012) Clin Exp Immunol, 167:137-48.
Chothia and Lesk (1987) J Mol Biol, 196:901-917.
Chothia et al. (1989) Nature, 342:877-883.
Coligan et al. (ed.), Current Protocols in Immunology, 1991, John Wiley & Sons.
Cuello, ASIN 0471900524, 1984, John Wiley and Sons.
Dall'Acqua et al. (2006) J Immunol, 177:1129-1138.
Dieffenbach et al. (ed.), PCR Primer: A Laboratory Manual, 1995, Cold Spring Harbor Laboratories.
Edelman et al. (1969) Proc Natl Acad Sci, 63:78-85.
Englebienne (1998) Analyst, 123:1599-1603.
Gisslen et al. (2016) EBioMedicine 3:135-140.
Giudicelli et al. (1997) Nucleic Acids Res, 25:206-211.
Glover et al. (ed.), DNA Cloning: A Practical Approach, 1995 and 1996, IRL Press, Volumes 1 to 4.
Harlow et al. (ed.), Antibodies: A Laboratory Manual, 1988, Cold Spring Harbour Laboratory.
Hezareh (2001) J Virol, 75:12161-12168.
Honnegher and Pliikthun, (2001) J Mol Biol, 309:657-670.
Jones et al. (2010) J Immunol Methods, 354:85-90.
Jostock et al. (2004) J Immunol Methods, 289:65-80.
Kabat et al. Sequences of Proteins of Immunological Interest Washington DC United States Department of Health and Human Services, 1987, 1991, 2001
Kopsidas et al. (2006) Immunol Lett, 107:163-168.
Kopsidas et al. (2007) BMC Biotechnol, 7:18-29.
Kuhle et al. (2016) Clin. Chem. Lab Med. 54:1655-166.
Kyte and Doolittle (1982) J Mol Biol, 157:105-132.
Largaespada et al. (1996) J Immunol Methods, 197:85-95.
Loos et al. (2008) Blood, 112:2648-56.
Mendoza et al. (1999) Biotechniques, 27:778-788.
Mortier et al. (2011) Exp Cell Res, 317:642-54.
Needleman and Wunsch (1970) J Mol Biol, 48:443-453.
Novotny et al. (1991) Proc Natl Acad Sci, 88:8646-8650.
Padlan et al. (1995) FASEB J, 9:133-139.
Perbal, A Practical Guide to Molecular Cloning, 1984, John Wiley and Sons.
Rainczuk et al. (2012) Reproduction, 144:303-17.
Rich and Myszka (2000) Curr Opin Biotechnol, 11:54-61.
Robins (1991) Adv Biosensors, 1:229-256.
Sambrook et al. Molecular Cloning: A Laboratory Manual, 1989, Cold Spring Harbor Laboratory Press.
Sambrook et al. Molecular Cloning: A Laboratory Manual, 2001 (Third Edition) Cold Spring Harbor Laboratory Press, New York.
Scholler et al. (2007) Biomarkers in Medicine 1:513-523.
Scopes, Protein Purification: Principles and Practice, 1994, Springer Verlag.
Shao et al. (2019) Future Oncology 15:1863-1871.
Shields et al. (2001) J Biol Chem, 276:6591-6604.
Sinnathurai et al. (2018) International Journal of Rheumatic Diseases, 21:1915-1923.
Stemmer (1994) Nature, 370: 389-91.
Thie et al. (2009) Method Mol Biol, 525:309-322.
Vuento et al. (1997) Gynecologic Oncology 64:141-146.
Windmuller et al. (2017) Oncogenesis, 6:e331.

The invention claimed is:

1. A C-X-C motif chemokine ligand 10 (CXCL10) binding protein, wherein the binding protein binds to full-length human CXCL10, N-terminally truncated CXCL10 and citrullinated CXCL10, wherein the binding protein is an antibody or antigen-binding fragment thereof comprising:
(i) a heavy chain variable region ($V_H$) comprising:
   a) a complementarity determining region (CDR) 1 comprising a sequence set forth in amino acids 25-34 of SEQ ID NO: 11; and
   b) a CDR2 comprising a sequence set forth in amino acids 49-65 of SEQ ID NO: 11; and
   c) a CDR3 comprising a sequence set forth in amino acids 98-108 of SEQ ID NO: 11; and
a light chain variable region ($V_L$) comprising:
   a) a CDR1 comprising a sequence set forth in amino acids 23-33 of SEQ ID NO: 12; and
   b) a CDR2 comprising a sequence set forth in amino acids 49-55 of SEQ ID NO: 12; and
   c) a CDR3 comprising a sequence set forth in amino acids 88-96 of SEQ ID NO: 12; or
(ii) a $V_H$ comprising:
   a) a CDR1 comprising a sequence set forth in SEQ ID NO: 13; and
   b) a CDR2 comprising a sequence set forth in SEQ ID NO: 14; and
   c) a CDR3 comprising a sequence set forth in SEQ ID NO: 15; and
a $V_L$ comprising:
   a) a CDR1 comprising a sequence set forth in SEQ ID NO: 16; and
   b) a CDR2 comprising a sequence of LAS; and
   c) a CDR3 comprising a sequence set forth in SEQ ID NO: 18.

2. The CXCL10 binding protein of claim 1 which binds the epitope NH2-LSRTVRCTCISISNQPVNPRSLE-COOH (SEQ ID NO: 26) of full-length human CXCL10, N-terminally truncated CXCL10 and citrullinated CXCL10; and/or wherein the binding protein:
  (i) binds to full-length human CXCL10 with a KD of 50 nM or less; and/or
  (ii) binds to N-terminally truncated human CXCL10 with a KD of 5 nM or less.

3. The CXCL10 binding protein according to claim 1, wherein the binding protein is an antibody or antigen binding fragment thereof comprising:
  $V_H$ comprising an amino acid sequence set forth in SEQ ID NO: 11 and a $V_L$ comprising an amino acid sequence set forth in SEQ ID NO: 12.

4. The CXCL10 binding protein according to claim 1, wherein the binding protein is conjugated to a detectable label selected from the group consisting of a radiolabel, an enzyme, a fluorescent label, a luminescent label, a bioluminescent label, a magnetic label, a prosthetic group, and a contrast agent.

5. A composition comprising the binding protein of claim 1 and a carrier.

\* \* \* \* \*

SEQUENCE LISTING

```
Sequence total quantity: 26
SEQ ID NO: 1             moltype = AA   length = 98
FEATURE                  Location/Qualifiers
source                   1..98
                         mol_type = protein
                         organism = Homo sapiens
SEQUENCE: 1
MNQTAILICC LIFLTLSGIQ GVPLSRTVRC TCISISNQPV NPRSLEKLEI IPASQFCPRV   60
EIIATMKKKG EKRCLNPESK AIKNLLKAVS KERSKRSP                          98

SEQ ID NO: 2             moltype = AA   length = 77
FEATURE                  Location/Qualifiers
source                   1..77
                         mol_type = protein
                         organism = Homo sapiens
SEQUENCE: 2
VPLSRTVRCT CISISNQPVN PRSLEKLEII PASQFCPRVE IIATMKKGE KRCLNPESKA    60
IKNLLKAVSK ERSKRSP                                                 77

SEQ ID NO: 3             moltype = AA   length = 115
FEATURE                  Location/Qualifiers
REGION                   1..115
                         note = heavy chain VH amino acid sequence of anti-CXCL10
                          antibody RA2
source                   1..115
                         mol_type = protein
                         organism = synthetic construct
SEQUENCE: 3
QVQLQQPGAE LVRPGASVKL SCKASGYTFT SHWMIWVKQR PGQGLEWIGM IDPSDSATHY   60
NQMFKDKATL TVDKSSSTAY MQLSSLTSED SAVYYCANTR HDESWGQGTL VTVSA       115

SEQ ID NO: 4             moltype = AA   length = 115
FEATURE                  Location/Qualifiers
REGION                   1..115
                         note = light chain VL amino acid sequence of anti-CXCL10
                          antibody RA2
source                   1..115
                         mol_type = protein
                         organism = synthetic construct
SEQUENCE: 4
DIQMTQSPSS LSASLGGRVT ITCKASQDIH KYIAWYQHKP GKGPRLLIYD TSTLQPGIPS   60
RFTGSGSGRD YSFSISNLEP EDIATYYCLQ YDDLYTFGGG TKLEIKRADA APTVS       115

SEQ ID NO: 5             moltype = AA   length = 8
FEATURE                  Location/Qualifiers
REGION                   1..8
                         note = heavy chain VH CDR1 amino acid sequence of
                          anti-CXCL10 antibody RA2
source                   1..8
                         mol_type = protein
                         organism = synthetic construct
SEQUENCE: 5
GYTFTSHW                                                           8

SEQ ID NO: 6             moltype = AA   length = 8
FEATURE                  Location/Qualifiers
REGION                   1..8
                         note = heavy chain VH CDR2 amino acid sequence of
                          anti-CXCL10 antibody RA2
source                   1..8
                         mol_type = protein
                         organism = synthetic construct
SEQUENCE: 6
IDPSDSAT                                                           8

SEQ ID NO: 7             moltype = AA   length = 8
FEATURE                  Location/Qualifiers
REGION                   1..8
                         note = heavy chain VH CDR3 amino acid sequence of
                          anti-CXCL10 antibody RA2
source                   1..8
                         mol_type = protein
                         organism = synthetic construct
SEQUENCE: 7
ANTRHDES                                                           8

SEQ ID NO: 8             moltype = AA   length = 6
FEATURE                  Location/Qualifiers
```

```
REGION                  1..6
                        note = light chain VL CDR1 amino acid sequence of
                         anti-CXCL10 antibody RA2
source                  1..6
                        mol_type = protein
                        organism = synthetic construct
SEQUENCE: 8
QDIHKY                                                                   6

SEQ ID NO: 9            moltype =   length =
SEQUENCE: 9
000

SEQ ID NO: 10           moltype = AA   length = 8
FEATURE                 Location/Qualifiers
REGION                  1..8
                        note = light chain VL CDR3 amino acid sequence of
                         anti-CXCL10 antibody RA2
source                  1..8
                        mol_type = protein
                        organism = synthetic construct
SEQUENCE: 10
LQYDDLYT                                                                 8

SEQ ID NO: 11           moltype = AA   length = 129
FEATURE                 Location/Qualifiers
REGION                  1..129
                        note = heavy chain VH amino acid sequence of anti-CXCL10
                         antibody RG2
source                  1..129
                        mol_type = protein
                        organism = synthetic construct
SEQUENCE: 11
QIQLVQSGPD LKKPGETVKI SCKASGYTFT NYGMNWVKQA PGKGLKWMAW INTNSGEPTY        60
AEEFKGRFAL SLDTSASTAY LQINNLKNED TATYFCARYT GEFFYNGSSY VSYWYFDVWG       120
AGATVTVSS                                                              129

SEQ ID NO: 12           moltype = AA   length = 120
FEATURE                 Location/Qualifiers
REGION                  1..120
                        note = light chain VL amino acid sequence of anti-CXCL10
                         antibody RG2
source                  1..120
                        mol_type = protein
                        organism = synthetic construct
SEQUENCE: 12
DIVLTQSPAS LAVSLGQRAT ISCRASKSVS SSGYSYMHWY QQKPGQPPKL LIYLASNLES        60
GVPARFSGSG SGSDFTLNIH PVEEEDAATY YCQHSRDLPW TFGGGTKLEI KRADAAPTVS       120

SEQ ID NO: 13           moltype = AA   length = 8
FEATURE                 Location/Qualifiers
REGION                  1..8
                        note = heavy chain VH CDR1 amino acid sequence of
                         anti-CXCL10 antibody RG2
source                  1..8
                        mol_type = protein
                        organism = synthetic construct
SEQUENCE: 13
GYTFTNYG                                                                 8

SEQ ID NO: 14           moltype = AA   length = 8
FEATURE                 Location/Qualifiers
REGION                  1..8
                        note = heavy chain VH CDR2 amino acid sequence of
                         anti-CXCL10 antibody RG2
source                  1..8
                        mol_type = protein
                        organism = synthetic construct
SEQUENCE: 14
INTNSGEP                                                                 8

SEQ ID NO: 15           moltype = AA   length = 22
FEATURE                 Location/Qualifiers
REGION                  1..22
                        note = heavy chain VH CDR3 amino acid sequence of
                         anti-CXCL10 antibody RG2
source                  1..22
                        mol_type = protein
                        organism = synthetic construct
```

```
SEQUENCE: 15
ARYTGEFFYN GSSYVSYWYF DV                                                      22

SEQ ID NO: 16           moltype = AA  length = 10
FEATURE                 Location/Qualifiers
REGION                  1..10
                        note = light chain VL CDR1 amino acid sequence of
                        anti-CXCL10 antibody RG2
source                  1..10
                        mol_type = protein
                        organism = synthetic construct
SEQUENCE: 16
KSVSSSGYSY                                                                    10

SEQ ID NO: 17           moltype =   length =
SEQUENCE: 17
000

SEQ ID NO: 18           moltype = AA  length = 9
FEATURE                 Location/Qualifiers
REGION                  1..9
                        note = light chain VL CDR3 amino acid sequence of
                        anti-CXCL10 antibody RG2
source                  1..9
                        mol_type = protein
                        organism = synthetic construct
SEQUENCE: 18
QHSRDLPWT                                                                     9

SEQ ID NO: 19           moltype = DNA  length = 345
FEATURE                 Location/Qualifiers
misc_feature            1..345
                        note = heavy chain VH nucleotide sequence of anti-CXCL10
                        antibody RA2
source                  1..345
                        mol_type = other DNA
                        organism = synthetic construct
SEQUENCE: 19
caggtccaac tgcagcagcc tggggctgag ctggtgaggc ctggggcttc agtgaagctg      60
tcctgcaagg cttctggcta caccttcacc agtcactgga tgatctgggt gaagcagagg     120
cctggacaag gccttgaatg gattggtatg attgatcctt cagacagtgc aactcactac     180
aatcaaaagt tcaaggacaa ggccacattg actgtagaca atcctccag cacagcctac      240
atgcagctca gcagcctgac atctgaggac tctgcggtct attactgtgc aaatactagg     300
cacgacgagt cctggggcca agggactctg gtcactgtct ctgca                    345

SEQ ID NO: 20           moltype = DNA  length = 345
FEATURE                 Location/Qualifiers
misc_feature            1..345
                        note = light chain VL nucleotide acid sequence of
                        anti-CXCL10 antibody RA2
source                  1..345
                        mol_type = other DNA
                        organism = synthetic construct
SEQUENCE: 20
gacatccaga tgacacagtc tccatcctca ctgtctgcat ctctgggagg cagagtcacc      60
atcacttgca aggcaagcca agacattcac aagtatatag cttggtacca acacaagcct     120
ggaaaaggtc ctagactgct catatatgac acatctacat acagccagg catcccatca      180
aggttcactg gaagtgggtc tgggagagat tattccttca gcatcagcaa cctggagcct     240
gaagatattg caacttatta ttgtctacag tatgatgatc tgtacacgtt cggagggggg     300
accaagctgg aaataaaacg ggctgatgct gcaccaactg tatcc                    345

SEQ ID NO: 21           moltype = DNA  length = 387
FEATURE                 Location/Qualifiers
misc_feature            1..387
                        note = heavy chain VH nucleotide sequence of anti-CXCL10
                        antibody RG2
source                  1..387
                        mol_type = other DNA
                        organism = synthetic construct
SEQUENCE: 21
cagatccagt tggtgcagtc tggacctgac ctgaagaagc ctggagagac agtcaagatc      60
tcctgcaagg cttctgggta taccttcaca aactatggaa tgaactgggt gaagcaggct     120
ccaggaaagg gtttaaagtg gatggcctgg ataaacacca actctggaga gccaacatat     180
gctgaagagt tcaagggacg atttgccttt tctttggata cctctgccag cactgcctat     240
ttgcagatca caacctcaa aaatgaggac acggctacat atttctgtgc aagatacacg      300
gggaattttt ttacaatgg tagtagttac gtaagttact ggtacttcga tgtctgggcc     360
gcaggggcca cggtcaccgt ctcctca                                        387

SEQ ID NO: 22           moltype = DNA  length = 360
```

```
FEATURE                 Location/Qualifiers
misc_feature            1..360
                        note = light chain VL nucleotide acid sequence of
                            anti-CXCL10 antibody RG2
source                  1..360
                        mol_type = other DNA
                        organism = synthetic construct
SEQUENCE: 22
gacattgtgc tcacacagtc tcctgcttcc ttagctgtat ctctggggca gagggccacc    60
atctcatgca gggccagcaa aagtgtcagt tcatctggct atagttatat gcactggtac   120
caacagaaac caggacagcc acccaaactc ctcatctatc ttgcatccaa cctagaatct   180
ggggtccctg ccaggttcag tggcagtggg tctgggtcag acttcaccct caacatccat   240
cctgtggagg aggaggatgc tgcaacctat tactgtcagc acagtaggga tcttccgtgg   300
acgttcggtg gaggcaccaa actggaaatc aaacgggctc atgctgcacc aactgtatcc   360

SEQ ID NO: 23           moltype = AA  length = 25
FEATURE                 Location/Qualifiers
REGION                  1..25
                        note = peptide sequence comprising the intact N-terminus of
                            human CXCL10
source                  1..25
                        mol_type = protein
                        organism = synthetic construct
SEQUENCE: 23
VPLSRTVRCT CISISNQPVN PRSLE                                          25

SEQ ID NO: 24           moltype = AA  length = 23
FEATURE                 Location/Qualifiers
REGION                  1..23
                        note = peptide sequence comprising the truncated N-terminus
                            of human CXCL10
source                  1..23
                        mol_type = protein
                        organism = synthetic construct
SEQUENCE: 24
LSRTVRCTCI SISNQPVNPR SLE                                            23

SEQ ID NO: 25           moltype = AA  length = 25
FEATURE                 Location/Qualifiers
REGION                  1..25
                        note = Human CXCL10 epitope
source                  1..25
                        mol_type = protein
                        organism = synthetic construct
SEQUENCE: 25
VPLSRTVRCT CISISNQPVN PRSLE                                          25

SEQ ID NO: 26           moltype = AA  length = 23
FEATURE                 Location/Qualifiers
REGION                  1..23
                        note = Human CXCL10 epitope
source                  1..23
                        mol_type = protein
                        organism = synthetic construct
SEQUENCE: 26
LSRTVRCTCI SISNQPVNPR SLE                                            23
```